United States Patent
Bos et al.

(10) Patent No.: US 9,259,461 B2
(45) Date of Patent: Feb. 16, 2016

(54) **VACCINE COMPRISING PROTEIN NMB0964 FROM *NEISSERIA MENINGITIDIS***

(75) Inventors: Martine Petronella Bos, Utrecht (NL); Jan Poolman, Rixensart (BE); Michiel Stork, Utrecht (NL); Johannes Petrus Maria Tommassen, Utrecht (NL); Vincent Weynants, Rixensart (BE)

(73) Assignee: GlaxoSmithKline Biologicals, S.A., Rixensart (BE)

( * ) Notice: Subject to any disclaimer, the term of this patent is extended or adjusted under 35 U.S.C. 154(b) by 426 days.

(21) Appl. No.: 13/062,319

(22) PCT Filed: Mar. 6, 2009

(86) PCT No.: PCT/EP2009/052689
§ 371 (c)(1),
(2), (4) Date: Mar. 4, 2011

(87) PCT Pub. No.: WO2010/025964
PCT Pub. Date: Mar. 11, 2010

(65) Prior Publication Data
US 2011/0189215 A1    Aug. 4, 2011

(30) Foreign Application Priority Data
Sep. 8, 2008 (GB) .................................. 0816447.7

(51) Int. Cl.
*A61K 39/00* (2006.01)
*A61K 39/095* (2006.01)
*A61P 31/04* (2006.01)
*C12P 21/00* (2006.01)
*C07K 14/22* (2006.01)

(52) U.S. Cl.
CPC ............... *A61K 39/095* (2013.01); *C07K 14/22* (2013.01); *C12P 21/00* (2013.01)

(58) Field of Classification Search
None
See application file for complete search history.

(56) References Cited

U.S. PATENT DOCUMENTS

2007/0031449 A1*   2/2007   Bos et al. .................. 424/203.1

FOREIGN PATENT DOCUMENTS

| WO | WO 00/55327 A2 * | 9/2000 |
| WO | WO 01/85772 | 11/2001 |
| WO | WO 2005/032583 | 4/2005 |

OTHER PUBLICATIONS

Dove et al. Microbiology 149: 1859-1869, 2003.*
Turner, et al., "Neisserial TonB-dependent outer-membrane proteins: detection, regulation and distribution of three putative candidates identified from the genome sequences," Microbiology, vol. 147, No. 5, pp. 1277-1290 (2001).
Database Geneseq [Online], "Neisserial meningitidis virulence protein #101," XP002542293 retrieved from EBI accession No. GSP:AAU73011 (2002).
O'Dwyer, et al. "Expression of heterologous antigens in commensal Neisseria spp.: Preservation of conformational epitopes with vaccine potential," Infection and Immunity, vol. 72, No. 11, pp. 6511-6518 (2004).
Vaughan, et al., "Proteomic analysis of Neisseria lactamica and Neisseria meningitidis outer membrane vesicle vaccine antigens," Vaccine, vol. 24, No. 25, pp. 5277-5293 (2006).
Pawlik, et al., The Zinc-Responsive Regulon of Neisseria meningitidis Comprises 17 Genes under Control of a Zur Element, J Bacteriol 194(23): 6594-6603 (2012).

* cited by examiner

*Primary Examiner* — S. Devi
(74) *Attorney, Agent, or Firm* — Eric J. Kron

(57) ABSTRACT

The present invention relates to immunogenic compositions comprising neisserial blebs with upregulated levels of the NMB0964 antigens such that bacterial antibodies are generated against said antigen. Methods are also provided to upregulate expression through removal of the zinc repression mechanism of the cell or promoter or through removal of zinc from the culture medium.

6 Claims, 11 Drawing Sheets

Fig. 3
A
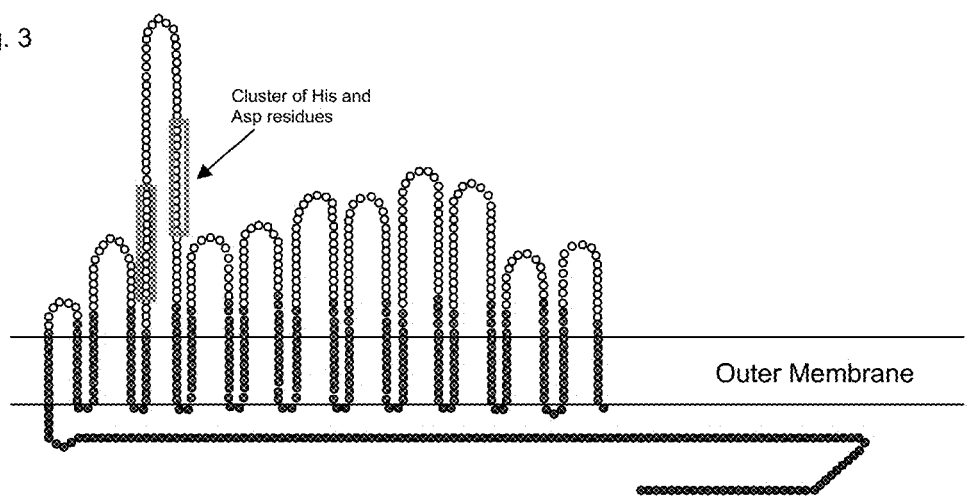
Cluster of His and Asp residues
Outer Membrane
Loop  RDQYGLPAHSHEYDDCHADIIWQKSLINKRYLQLYPHLLTEEDIDYDNPGLSCGFHDDDNAHAHTHS
(SEQ ID NO: 18)
B
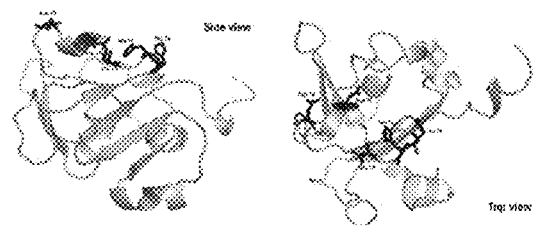

Expression of TdfI in 32 different *Neisseria meningitidis* strains

```
           <    Signal sequence    >    <Tb > <    plug domain
MC58     1 MAQTTLKPIVLSILLINTPLLAQAHETEQSVDLETVSVVGKSRPPATSGLLHTSTASDKI 60
O53322     .........................G....T............................
Z2491      ....................S...G.....G............................
FAM18      ............................................................
α14        ............................................................
α153       ..........................DR................................
α275       ............................................................

Plug domain
MC58    61 ISGDTLRQKAVNLGDALDGVPGIHASQYGGGASAPVIRGQTGRRIKVLNHHGETGDMADF 120
O53422     ............................................................
Z2491      ............................................................
FAM18      L...........................................................
α14        ............................................................
α153       ............................................................
α275       ............................................................

plug domain                      >< Tm1    >
MC58   121 SPDHAIMVDTALSQQVEILRGPVTLLYSSGNVAGLVDVADGKIPEKMPENGVSGELGLRL 180
O53422     ............................................................
Z2491      .........S..................................................
FAM18      ............................................................
α14        ............................................................
α153       ............................................................
α275       .........S..................................................

<loop1>< Tm2     > <     Tm3  ><     loop2    ><      Tm4
MC58   181 SSGNLEKLTSGGINIGLGKNFVLHTEGLYRKSGDYAVPRYRNLKRLPDSHADSQTGSIGL 240
O53422     ...........................................................K......
Z2491      ............................................................
FAM18      ............................................................
α14        ............................................................
α153       ............................................................
α275       ............................................................

>  < Tm5    ><              loop3
MC58   241 SWVGEKGFIGVAYSDRRDQYGLPAHSHEYDDCHADIIWQKSLINKRYLQLYPHLLTEEDI 300
O53422     ..........A................................................V
Z2491      ..........A.................................................
FAM18      ............................................................
α14        ...........................................................V
α153       ..........A.................................................
α275       ..........A.................................................

>< Tm6      >  <   Tm7       >
MC58   301 DYDNPGLSCGFHDDDNAHAHTHSGRPWIDLRNKRYELRAEWKQPFPGFEALRVHLNRNDY 360
O53422     ........................N.K..................L.............
Z2491      ................D....A.N.K..................................
FAM18      ................D............................................
α14        ................D....A.N.K..................................
α153       ................D....A.N.K..................................
α275       ................D....A.N.K..................................
```

Figure 8B

```
              <   loop4      ><    Tm8    > <   Tm9    ><    loop5
MC58    361 RHDEKAGDAVENFFNNQTQNARIELRHQPIGRLKGSWGVQYLQQKSSALSAISEAVKQPM 420
O53422      ..H...............K.........................................
Z2491       ..............................................G........T........
FAM18       .................................................................
α14         .........................................................T........
α153        .................................................................
α275        ..H...........................................G........T........

><   Tm10    >  <   Tm11   ><    loop6
MC58    421 LLDNKVQHYSFFGVEQANWDNFTLEGGVRVEKQKASIQYDKALIDRENYYNHPLPDLGAH 480
O53422      .............E........................................KQ........
Z2491       ...........................................R....................
FAM18       ...........................................R....................
α14         ...........................................R....................
α153        ...........................................R....................
α275        ...........................................R....................

><    Tm12   >  <   Tm13   ><    loop7                  >
MC58    481 RQTARSFALSGNWYFTPQHKLSLTASHQERLPSTQELYAHGKHVATNTFEVGNKHLNKER 540
O53422      ............................................................
Z2491       ............................................................
FAM18       ............................................................
α14         ............................................................
α153        ............................................................
α275        ............................................................

<    Tm14   >  <   Tm15   ><             loop 8
MC58    541 SNNIELALGYEGDRWQYNLALYRNRFGNYIYAQTLNDGRGPKSIEDDSEMKLVRYNQSGA 600
O53422      ............................................................
Z2491       ............................................................
FAM18       ............................................................
α14         ............................................................
α153        ............................................................
α275        ............................................................

><    Tm16   >  <   Tm17   ><            loop9
MC58    601 DFYGAEGEIYFKPTPRYRIGVSGDYVRGRLKNLPSLPGREDAYGNRPFIAQDDQNAPRVP 660
O53422      ............................................................
Z2491       ...............................................L...A........
FAM18       ............................................................
α14         ............................................................
α153        ............................................................
α275        ............................................................

><    Tm18   >  <   Tm19   ><   loop10  ><    Tm20    > <
MC58    661 AARLGFHLKASLTDRIDANLDYYRVFAQNKLARYETRTPGHHMLNLGANYRRNTRYGEWN 720
O53422      .....V......................................................
Z2491       .....V......................................................
FAM18       .....V......................................................
α14         .....V......................................................
α153        .....V......................................................
α275        .....V......................................................

Tm21   ><    loop 11   ><   Tm22    >
MC58    721 WYVKADNLLNQSVYAHSSFLSDTPQMGRSFTGGVNVKF 758  (SEQ NO:19)
O53422      .....................................       (SEQ NO:20)
Z2491       .....................................       (SEQ NO:21)
FAM18       .....................................       (SEQ NO:22)
α14         .....................................       (SEQ NO:23)
α153        .....................................       (SEQ NO:24)
α275        .....................................       (SEQ NO:25)
```

Figure 9A

```
CLUSTAL FORMAT for T-COFFEE Version_6.07 [http://www.tcoffee.org]

A. baumannii         MLNKSK-------------------LFLAL-ITLGASK-ILL--AA---EGPVTTLNTI
A. pleuropneumoniae  MFNKKL-------------------LAVL-ISAQFSP-LVW--AN---NNDVAVLDEV
H. parasuis          MINNRTTE---------------QQNNRTTA-FSLAFSL-LLCCLGI---NAEQLELDEI
B. pertussis         MICYIVSFNENGTSFYREGNMRFERHPLSAAL-ALALAWQGAHAQASADGTSEAATLAPI
M. catarrhalis       MKVTMI-----------------KKPLACAI-LATFSM-PMLAEANLKD-KPTVILDGV
M. haemolytica       ML---------------------KKNYLTVSI-LLAISG-VGYA--------NEISLETI
P. multocida         MPLLTLKINM----F----F-MRKISYLSLCVISALYSQ-LAVAQSPLKNTSEHIELEPI
N. meningitidis      MAQTTL-------------------KPIVLSI-LLINT--PLLAQAHE--TEQSVDLETV
                       *                       :            *  :

A. baumannii         VLTAQSDELGSELLGKSLNVSNQFIDTSK-LKQRSTTLGDALGTELGIHSNQYGGGASAP
A. pleuropneumoniae  SVVGSTPSISQGSEVTLLKVSDKIIAGKE-FKKRSATLGNALAAELGVHSNPFGGGASKP
H. parasuis          SVMGKVPE---GNSISFLKVSDAIIDGEK-FKNRSATLGNALSSELGVHSTPFGGGASAP
B. pertussis         TVSA--SPL-AG-DLDSMTAPAAVLEGDQLLLRRQGTLGDTLDGLPGVHADTFGGGASRP
M. catarrhalis       SITSLADQNTEFGVNHSKTVSGITVSKEQ-LQQRATTLGDALAGELGVHSNHFGGGASAP
M. haemolytica       TVDGNTPSTKGKLLGGELNSNESVVDEKN-LKQGSITLGNALSGELGIHSSQFGGGASTP
P. multocida         FVNTLIESREGAPLGGRLMASEKIIPAYS-LKQRGSNLGDALSSELGIHASQFGGGASAP
N. meningitidis      SVVGKSRPRATSGLLHTSTASDKIISGDT-LRQKAVNLGDALDGVPGIHASQYGGGASAP
                                :            :  .  .**::*    *:*: :***** *

A. baumannii         IIRGQEGKRIKVLQNNADVLDMSNMSPDHAVTVEPSLAKSIEIIRGASTLLYSSNSAAGV
A. pleuropneumoniae  IIRGQEGARIRILQNGSDVIDMSNLSPDHAVVADSLLAKQVEILRGSSTLLYASSSPAGI
H. parasuis          IIRGQEGVRVKILQNNADVVDMSNISPDHAITADTLLANQVEILRGASTLLYASSSPAGI
B. pertussis         VIRGQTAPRVKVLSDGSELMDASAISPDHAVTTEPLLADKIEVLRGPATLLYGGGAIGGV
M. catarrhalis       IIRGQEGKRLKILQNGSEVVDMSGLSPDHAIAVDTTLAKQVEIVRGSGALLYASGNSAGV
M. haemolytica       IIRGQESKRAKILQNNGENLDMNGSPDHAVTVDALLAKRIEILRGPTTLLYSAGNTAGV
P. multocida         VIRGQEGKRIKVLSSGNETLDMSAMSPDHAVAVDSLLAKKVEILRGANTLLYSSGNAAGV
N. meningitidis      VIRGQTGRRIKVLNHHGETGDMADFSPDHAIMVDTALSQQVEILRGPVTLLYSSGNVAGL
                     :****  *  ::*.      * :  :*****:  ..  *:..  *::**.  :***...  .*:

A. baumannii         VNVIDYKIPTQMPQDGLEGNTTLRFNTGSNEKLTTAGVTVGLSPRVALRAEGLYRNAGNY
A. pleuropneumoniae  VNVVDKRIPTEIPEKGYEVELNSRFDTAAKEKVGALGATFGIGKHIAVRAEGLTRHSDNY
H. parasuis          VNIVDQRIPNKMPKKGYEVTLSSRFDTASKEKVYALGTTIGIGKHLALRLEGLDRQSQNY
B. pertussis         VNVLDRKIPTAVPQQGIEAEAELRGATGTKERAGAIGITAGSG-NFAVRVEGLKRRSSDY
M. catarrhalis       VNVVDDKIPSKLPSK-LQGDVTVRLSSANREKLITASAEAPLGEHVAVRVAGLSKQAADY
M. haemolytica       INVVDNKIPTAIPEKGYEGQFGVRFGSASKERLTYAGSTFALGNHLALRVQGMYNKASEY
P. multocida         VNVVDNKIPTAE-VVGVEGEVGLRTGSADNERLVNVALDVGLSKHFALHLEGLHKKAGDY
N. meningitidis      VDVADGKIPEKMPENGVSGELGLRLSSGNLEKLTSGGINIGLGKNFVLHTEGLYRKSGDY
                     ::: *  :**       .    *  :.  *:         .  ...::   *:..:  :*

A. baumannii         KTPHYQSSSYNSLEDLEN---QNIVYKNLKYLPESWAESRLGTLGLSWIDDNTYLGVSYT
A. pleuropneumoniae  RVPGINL------------------GERLNYVPDTYNKSKVGTLGLSFVGBQGYIGASYS
H. parasuis          KVPQIKL------------------GETLNYVPDTYHQSKVGTIGLSFIGEKGYLGASYN
B. pertussis         RVPDWPD------------------GKLAGSYSESGQGTVGMSWITPRGYVGVAFT
M. catarrhalis       KTPRFDRHVFNKKHEDDNTQPEFIYKDTLKHLPDSHAKSNAGTLGVSWVGNQGFLGASVS
M. haemolytica       YAPHFTI-----------------EGKPYHRVPDSDVQSQTGTVSLSWIGERGHLGIAYT
P. multocida         RTPSYQY-----------------QGSTHHKLANSFVDNRSGSVGLSWVGDKGYLGVAYS
N. meningitidis      AVPRYR--------------------NLKRLPDSHADSQTGSIGLSWVGEKGFIGVAYS
                      .*                        :.  :  .  *::.:*::   ..:* :.

A. baumannii         HRHDEYGLPA▓▓▓▓▓▓▓▓▓▓▓AISINTRISGLKNYLLYYPQLMEEQDINYVNPRPDC▓--
A. pleuropneumoniae  KRRDNYGLPG▓▓▓▓▓▓▓▓▓▓▓IYGN---KQGKYAYTYLYPHLIGEENIG-SNPHFHCGT▓
H. parasuis          QRKDRYGLPG▓▓▓▓▓▓▓▓▓▓▓IYDM--RLQGKHSYTNLYPHLMSDEMVT-ENPHFHCGT▓
B. pertussis         HLESKYGLPG▓▓▓▓▓▓▓▓▓▓▓G--------------------------SHLHCGG▓
M. catarrhalis       LRRDKYGLPN▓▓▓▓▓▓▓▓▓▓▓GISQ--SALQYKPYLRLYPFLMENDDLEFDNAGLECHT▓
M. haemolytica       DRRDKYGLIG▓▓▓▓▓▓▓▓▓▓▓IIRQ--AVMFAKGYLRFYPHLAEEGDIDYNNPGIRLL--
P. multocida         QRKDKYGLPA▓▓▓▓▓▓▓▓▓▓▓VLLS--DAHWRKPYLKHYPFLMEETDIDYNNPGIDCIKK
N. meningitidis      DRRDQYGLPA▓▓▓▓▓▓▓▓▓▓▓IIWQ--KSLINKRYLQLYPHLLTEEDIDYDNPGLSCGF-
                       ...***  *.*  ::

A. baumannii         --------------Q▓ ▓▓▓▓▓▓ ▓▓▓▓---NAPYIDLNTRRYDMRGEFTQPFTGIDK
A. pleuropneumoniae  ------▓▓▓▓▓▓▓▓▓ ▓▓▓▓▓▓ ▓▓▓▓---PGPWVDLESKRFDVKAELRQPFKGIDK
H. parasuis          ------YDLDPSHSHDN ▓▓▓▓▓▓ ▓▓▓▓---IGPWVDLHSKRIDIKGEIKQPLPMLDK
B. pertussis         ▓▓▓▓▓ ▓▓▓▓▓▓▓▓▓▓▓ ▓▓▓▓▓▓▓ ▓▓▓▓GAGDVPYVKLRSNRTDLRAEYTDPFAGFEK
M. catarrhalis       ▓▓▓▓ ▓▓▓▓▓▓▓▓▓▓ ▓▓▓▓▓▓ ▓▓▓▓---GKPWIDLKMKRYDVQGQINAPFAGIDK
M. haemolytica       ----▓▓▓▓▓▓▓▓ ▓▓▓▓▓▓ ▓▓-QDTHRK---GKPWIDMHSKRYDIDGSLQNPLPGFEE
P. multocida         EW▓▓▓▓▓▓▓▓▓▓▓▓▓▓ ▓▓▓▓▓▓▓▓▓▓---ADPHIALNTQRWDLRGEWKNPVKGLDK
N. meningitidis      ------H▓         ▓▓ DNAHA ▓▓▓▓S--GRPWIDLRNKRYELRAEWKQPFPGFEA
                      . *        * : :.  .* ::  ..   *.  ::
```

Figure 9B

```
A. baumannii        IRTSLSYIDYFHNELEGDKI------------------TNFFKNTGKVGRIELSHQ----
A. pleuropneumoniae IKVSYADADYYHDEKDAGVLATRYH-KQLKKDQDYGKPVNIFKNRGKNARLEIYHA----
H. parasuis         IQLSYAQTDYYHDEKDAGKSGDTINPNRVDKSKDFGKPVNIFKNQGKNARLEFFHT----
B. pertussis        IRFRGGLTDYRHDEIEGGQL--------------GTRFQNRGYDARLELTHR----
M. catarrhalis      IRASMGKVDYHHDEIDGGEK------------------TSFFDNQANVWRLEASHTPIHT
M. haemolytica      AKISANYVDYYHDEKDGKRV------------------ENYFKNKGKNLRFELVHK----
P. multocida        VRFSIAKVGYRHDEKSGAIS------------------DNSFKNKGYSARVEFLHQ----
N. meningitidis     LRVHLNRNDYRHDEKAGDAV------------------ENFFNNQTQNARIELRHQ----
                              .* *:*  .                             .  *.*      *.*    *

A. baumannii        PLGELTGILGLQYLEQDNSALSPVHSQEGHTTYLDTQQLLNRNVTKNFSVFGLEKYNW-N
A. pleuropneumoniae PLGGLTGVWGVQYQTQKSSMHAPKD--------REVKFPLVENTNKQMSLFGIEQYMW-D
H. parasuis         PIGGLTGMFGVQYQTLQSSANTPNN--------REVQWPLVDNRNKQISLFALEQYAW-D
B. pertussis        PLYGWHGVVGVQTSYSDFRA-------------TGEEAPLPRSKTRAHGLFLLEEYRW-A
M. catarrhalis      PMGKFSGVFGVGYLTSKNSGLVPPRYEDG--NKQDTQNILHNNKTKTGSVFWFEEYKPND
M. haemolytica      EWKGLKGAIGVQYTNQSTSALALEASRAA--KVFNKQPLLNNPKTKLWSLFAIERLNL-G
P. multocida        PIAGVSGLIGLSHVYQDSYALDNHTL------EYRKQNLLSDHTTAQQSLFLMEHVEL-G
N. meningitidis     PIGRLKGSWGVQYLQQKSSALSAIS-------EAVKQPMLLDNKVQHYSFFGVEQANW-D
                                *  *:        .                       :  *        ..*..*.

A. baumannii        DFTFELGARIEKQKVSMDYDIEKIKDSMKPWPNKYNSPYVEKNNKIRAQNLK-SILEAVQ
A. pleuropneumoniae NFALEFAGRVEKQKIEIEYDRNEIKRLQDHYRIS---------------GGK-QVEPDLS
H. parasuis         NFAIELGLRTEKQNIHIDYDLAKIQKQQKFNERT---------------YGK-QVDPDLS
B. pertussis        DWRFELGARQDWQRVSPQ--------------------------------------SGAP
M. catarrhalis      KLTVDAAARIEKQTITMDYDKDAIYQSLNLGLATAHEPDI--------RFKRLLDSGTLN
M. haemolytica      DFTFELSGRAERQKIAMDYDVKLIDRWLGFNT--------------------PMPNLD
P. multocida        KWQFDIGGRVEKQRIAMKYHFNVPKDEQP---------------------PEELTR
N. meningitidis     NFTLEGGVRVEKQKASIQYDKALIDRENYYNH----------------------PLPDLG
                       .   . :  *   :   *

A. baumannii        PNKETAFSYAGTVHWRFAPNYILSLTGTHQERLPNAQEMYTHGMHLATNSFEIGNRFLRK
A. pleuropneumoniae PYNQNAYAYSSTLNWFFHPDYQLSFTASHNERFPTPMELYYHGQHIATNSFEYGNKDLKK
H. parasuis         DYDEKAISYTGAFNWFFHPDYQLSFTASHNERLPTPMELYYHGQHLATNSFEYGNKDLKK
B. pertussis        ASRTAGTSLSAAAIWDFAPQYSLALSVSRSQRLPSAQELYADGVHLATNTYEIGDPGLDR
M. catarrhalis      PKKQTARSYAVGTHLQLTPKHKLSLNLPNAQELYAHGMHLATNSFEIGNRFLNK
M. haemolytica      PHKDKGYSYSFATHWYFAPNHKLTLNAAHQERLPNAQELYAHGKHIALNAFEAGNKNLKK
P. multocida        PHKSKAYSYALSANYQLNEQHQFNMIVSHQERLPNAQELYAHGKHLATNSFEAGNKNLTK
N. meningitidis     AHRQTARSFALSGNWYFTPQHKLSLTASHQERLPSTQELYAHGKHVATNTFEVGNKHLNK
                                  .  :          :  .:  :  :     ::.:*;*.. *;*  .* *;* *;;* *;    *  :

A. baumannii        EKSNNLEISLAYKDDLLDYQISTYYYDFDNYIYLQTLNEVL---------GTTKVRDQHT
A. pleuropneumoniae EQSNNVELGLGYQTERVGYKVTVYNHFKNYIYNENLFR----------------ENQ
H. parasuis         EISNNFELGLGYHTEKLDYKLSTYYNNFDNYIYNETLYR-----------------SNN
B. pertussis        ETSRNVDLTLRKHSGDTTFSVSAFHNRVKNYIYANTLDR-----------------YED
M. catarrhalis      EKSNNIDLGLTFQGDKWDYRLGGYHYDFDNYVFLQTLSQYK--------QGLRGMRHDKD
M. haemolytica      ERSNQIELSLAYVGDKNVDYKLNLYHTRYGNYIYPLTLNDNR---------GPKSFTDEYN
P. multocida        ERSNNVELGWGYTGEKLGIKLSGYYQQFSNYIYAAILNNKTSCPWRPNSRCLRSLSDDYP
N. meningitidis     ERSNNIELALGYEGDRWQYNLALYRNRFGNYIYAQTLNDGR---------GPKSIEDDSE
                    *  *..:..:                :     :         **::       *

A. baumannii        LRINHYSQSAANFYGLEGNIGYQFNSVYHGSLFGDYVKGRLTNLPDAVIAYDIWNRE---
A. pleuropneumoniae LFMRRYNQAKARFYGIEAEASYRFNDKYQATIPGDMVRGWLTNLPPLTVNSDYSVPK---
H. parasuis         LFMRRYNQAKATFYGLEGIINYRFTPDYQFSVFGDMVKGKLKQLPDIKGLNDVYGEPILN
B. pertussis        FRLIEYTQRDAEFTGVEGEVRHRFGKVFSAAVFGDYVRGRLTG---------------
M. catarrhalis      LKTARYEQAAAKFYGFDVNIGYQINDVYHVALFGDYIRGKLTNLPDKKGRTDAYGN----
M. haemolytica      LKVNRYYQGEARFSGAEGEIGYLFTPNYRLAVFGDYVRGKLVNLPNIAMSYNIWTGE---
P. multocida        LRLYRYNQAKAKIYGLEAEVSYQISSTHSVSIFGDYVRGKLKDLPSLPIGYKYIYNE---
N. meningitidis     MKLVRYNQSGADFYGAEGEIYFKPTPRYRIGVSGDYVRGRLKNLPSLPGREDAYGN----
                    :      . *   *  *  :         :  **  :* *

A. baumannii        ------------------PTLAPQKDRYTPRLPPARLGTRLKADFDESLKGEIEYYRV
A. pleuropneumoniae -DYLPKDAKPG--------EDYLIYRADQNTPRTPPVRLGFRFNAEFTPNWSGDLELIRT
H. parasuis         PDYDPEYDEPEDQYYRPYLGKEMIKQADRVSPRLPPIRLGARFNAQLTENLSGSVEWMKV
B. pertussis        ------------------------GGGNLPRIPAARLGVRADAQWQ-NWAGGVEYFHV
M. catarrhalis      ---------RP-----------LIKQPDSHTPRLPPKRLGMKLTANVNANWSGFLEYRHT
M. haemolytica      ----------V------DKWASQPDISAPRIPPLRLGARFNADPNLNWSGMLEYYRV
P. multocida        -NYDMVGVQP----------TGWEKQPDGNAPRMSPMRLGIKWNAYFDNGISFNTQLYRV
N. meningitidis     --------RP-----------FIAQDDQNAPRVPAARLGFHLKASLTDRIDANLDYYRV
                                                 .  **  .. ***  :  *           :  :.
```

Figure 9C

```
A. baumannii        FKQDNISKFEQVTSGYNMLNMTLAYKNKLSHT--EYDLFFKANNLLDQKVYAHETFLPYI
A. pleuropneumoniae FTQRRTSQLEYITEGNTMLNIGVAYSNKWKDL--DYKISLNGTNLLNQPVYIHTSYHQFV
H. parasuis         FTQNKVSKLESSTKGYQLLNASLNYRRQIKGV--EYTVSLTGNNLLNQAVYIHNSYHPYV
B. pertussis        YRQDDIAAYESSTPGYDMVNATIRYRGKLDRT--AYEIYLRGNNLLNKLAFNHASFISTV
M. catarrhalis      FKQDKLANFERPTPAHNLVNLGLNYQHKPSHQAGSVQVFFNANNLLNDKVFAHETFFPDM
M. haemolytica      FAQKKVSKYEQVTPGHHQVNLGVTYSNHFNQT--EYQVFLKVDNLLNQKMYQHASYLPHI
P. multocida        FAQNKVARLETPTKGHTMLNLGMSYDGKMGNN--EYTLFANVNNVLNSRVYNHTSFLSYI
N. meningitidis     FAQNKLARYETRTPGHHMLNLGANYRRNTRYG--EWNWYVKADNLLNQSVYAHSSFLSDT
                    : *   :  * *  .   :*    *  :              *:*:.   : *  ::

A. baumannii        -PQIGRNFSLGLNLNF   (SEQ NO:26)
A. pleuropneumoniae -PQTGRNFILVVNVKF   (SEQ NO:27)
H. parasuis         -PQMGRNFILGLDLSF   (SEQ NO:28)
B. pertussis        APLPGRSVLLGVRLTY   (SEQ NO:29)
M. catarrhalis      -PQMGRNFMLGANFKF   (SEQ NO:30)
M. haemolytica      -PQMGRNAMLGMNISF   (SEQ NO:31)
P. multocida        -PQSGLGLNVGMNFKF   (SEQ NO:32)
N. meningitidis     -PQMGRSFTGGVNVKF   (SEQ NO:33)
                      * *  .       ..:
```

SEQUENCE LISTING

<160> NUMBER OF SEQ ID NOS: 33

<210> SEQ ID NO 1
<211> LENGTH: 23
<212> TYPE: DNA
<213> ORGANISM: Escherichia coli
<220> FEATURE:
<221> NAME/KEY: misc_feature
<222> LOCATION: (1)...(23)
<223> OTHER INFORMATION: n = A,T,C or G

<400> SEQUENCE: 1
gaaatgttat antataacat ttc                                           23

<210> SEQ ID NO 2
<211> LENGTH: 23
<212> TYPE: DNA
<213> ORGANISM: Neisseria meningitidis

```
<400> SEQUENCE: 2
gtaatgttat ataataacaa act                                            23

<210> SEQ ID NO 3
<211> LENGTH: 23
<212> TYPE: DNA
<213> ORGANISM: Neisseria meningitidis

<400> SEQUENCE: 3
caaacgttat acagtatcat atc                                            23

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
gatcatatgc atgaaactga gcaatcggtg                                     30

<210> SEQ ID NO 5
<211> LENGTH: 33
<212> TYPE: DNA
<213> ORGANISM: Artificial Sequence
<220> FEATURE:
<223> OTHER INFORMATION: Primer

<400> SEQUENCE: 5
gatggatcct taaatcttca cgttcacgcc gcc                                 33

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
tgacgcgtct cgacgctgag gtctgc                                         26

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
tgtgtacagt cgacttcaga cggccacg                                       28

<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
gcatcatatg gcacaaacta cactcaaacc c                                   31

<210> SEQ ID NO 9
<211> LENGTH: 32
<212> TYPE: DNA
<213> ORGANISM: Artificial Sequence
```

```
<220> FEATURE:
<223> OTHER INFORMATION: Primer

<400> SEQUENCE: 9
atgacgtctt aaaacttcac gttcacgccg cc                                     32

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gtacgatgat tgtgccgacc                                                   20

<210> SEQ ID NO 11
<211> LENGTH: 40
<212> TYPE: DNA
<213> ORGANISM: Artificial Sequence
<220> FEATURE:
<223> OTHER INFORMATION: Primer

<400> SEQUENCE: 11
actttaaact ccgtcgacgc aagtcgactg cggggttaa                              40

<210> SEQ ID NO 12
<211> LENGTH: 40
<212> TYPE: DNA
<213> ORGANISM: Artificial Sequence
<220> FEATURE:
<223> OTHER INFORMATION: Primer

<400> SEQUENCE: 12 ttaaccccg cagtcgactt gcgtcgacgg agtttaaagt                              40

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
gccatactgt tgcggatttg a                                                 21

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ttcgccgatg gcggaataca                                                   20

<210> SEQ ID NO 15
<211> LENGTH: 40
<212> TYPE: DNA
<213> ORGANISM: Artificial Sequence
<220> FEATURE:
<223> OTHER INFORMATION: Primer

<400> SEQUENCE: 15
ctttcagcgc aaagtcgact ccgtcgacgc gtgcctgttc                             40
```

```
<210> SEQ ID NO 16
<211> LENGTH: 40
<212> TYPE: DNA
<213> ORGANISM: Artificial Sequence
<220> FEATURE:
<223> OTHER INFORMATION: Primer

<400> SEQUENCE: 16
gaacaggcac gcgtcgacgg agtcgacttt gcgctgaaag                         40

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
tcctattgcg caatacccccc                                              20

<210> SEQ ID NO 18
<211> LENGTH: 67
<212> TYPE: PRT
<213> ORGANISM: Neisseria meningitidis

<400> SEQUENCE: 18
```

Arg Asp Gln Tyr Gly Leu Pro Ala His Ser His Glu Tyr Asp Asp Cys
 1               5                  10                  15

His Ala Asp Ile Ile Trp Gln Lys Ser Leu Ile Asn Lys Arg Tyr Leu
            20                  25                  30

Gln Leu Tyr Pro His Leu Leu Thr Glu Glu Asp Ile Asp Tyr Asp Asn
        35                  40                  45

Pro Gly Leu Ser Cys Gly Phe His Asp Asp Asp Asn Ala His Ala His
    50                  55                  60

Thr His Ser
65

```
<210> SEQ ID NO 19
<211> LENGTH: 758
<212> TYPE: PRT
<213> ORGANISM: Neisseria meningitidis

<400> S

```
Asp Thr Ala Leu Ser Gln Gln Val Glu Ile Leu Arg Gly Pro Val Thr
    130                 135                 140

Leu Leu Tyr Ser Ser Gly Asn Val Ala Gly Leu Val Asp Val Ala Asp
145                 150                 155                 160

Gly Lys Ile Pro Glu Lys Met Pro Glu Asn Gly Val Ser Gly Glu Leu
                165                 170                 175

Gly Leu Arg Leu Ser Ser Gly Asn Leu Glu Lys Leu Thr Ser Gly Gly
            180                 185                 190

Ile Asn Ile Gly Leu Gly Lys Asn Phe Val Leu His Thr Glu Gly Leu
        195                 200                 205

Tyr Arg Lys Ser Gly Asp Tyr Ala Val Pro Arg Tyr Arg Asn Leu Lys
    210                 215                 220

Arg Leu Pro Asp Ser His Ala Asp Ser Gln Thr Gly Ser Ile Gly Leu
225                 230                 235                 240

Ser Trp Val Gly Glu Lys Gly Phe Ile Gly Val Ala Tyr Ser Asp Arg
                245                 250                 255

Arg Asp Gln Tyr Gly Leu Pro Ala His Ser His Glu Tyr Asp Asp Cys
            260                 265                 270

His Ala Asp Ile Ile Trp Gln Lys Ser Leu Ile Asn Lys Arg Tyr Leu
        275                 280                 285

Gln Leu Tyr Pro His Leu Leu Thr Glu Glu Asp Ile Asp Tyr Asp Asn
    290                 295                 300

Pro Gly Leu Ser Cys Gly Phe His Asp Asp Asp Asn Ala His Ala His
305                 310                 315                 320

Thr His Ser Gly Arg Pro Trp Ile Asp Leu Arg Asn Lys Arg Tyr Glu
                325                 330                 335

Leu Arg Ala Glu Trp Lys Gln Pro Phe Pro Gly Phe Glu Ala Leu Arg
            340                 345                 350

Val His Leu Asn Arg Asn Asp Tyr Arg His Asp Glu Lys Ala Gly Asp
        355                 360                 365

Ala Val Glu Asn Phe Phe Asn Asn Gln Thr Gln Asn Ala Arg Ile Glu
    370                 375                 380

Leu Arg His Gln Pro Ile Gly Arg Leu Lys Gly Ser Trp Gly Val Gln
385                 390                 395                 400

Tyr Leu Gln Gln Lys Ser Ser Ala Leu Ser Ala Ile Ser Glu Ala Val
                405                 410                 415

Lys Gln Pro Met Leu Leu Asp Asn Lys Val Gln His Tyr Ser Phe Phe
            420                 425                 430

Gly Val Glu Gln Ala Asn Trp Asp Asn Phe Thr Leu Glu Gly Gly Val
        435                 440                 445

Arg Val Glu Lys Gln Lys Ala Ser Ile Gln Tyr Asp Lys Ala Leu Ile
    450                 455                 460

Asp Arg Glu Asn Tyr Tyr Asn His Pro Leu Pro Asp Leu Gly Ala His
465                 470                 475                 480

Arg Gln Thr Ala Arg Ser Phe Ala Leu Ser Gly Asn Trp Tyr Phe Thr
                485                 490                 495

Pro Gln His Lys Leu Ser Leu Thr Ala Ser His Gln Glu Arg Leu Pro
            500                 505                 510

Ser Thr Gln Glu Leu Tyr Ala His Gly Lys His Val Ala Thr Asn Thr
        515                 520                 525

Phe Glu Val Gly Asn Lys His Leu Asn Lys Glu Arg Ser Asn Asn Ile
    530                 535                 540

Glu Leu Ala Leu Gly Tyr Glu Gly Asp Arg Trp Gln Tyr Asn Leu Ala
```

```
                545                 550                 555                 560
Leu Tyr Arg Asn Arg Phe Gly Asn Tyr Ile Tyr Ala Gln Thr Leu Asn
                    565                 570                 575

Asp Gly Arg Gly Pro Lys Ser Ile Glu Asp Ser Glu Met Lys Leu
                580                 585                 590

Val Arg Tyr Asn Gln Ser Gly Ala Asp Phe Tyr Gly Ala Glu Gly Glu
                    595                 600                 605

Ile Tyr Phe Lys Pro Thr Pro Arg Tyr Arg Ile Gly Val Ser Gly Asp
            610                 615                 620

Tyr Val Arg Gly Arg Leu Lys Asn Leu Pro Ser Leu Pro Gly Arg Glu
625                 630                 635                 640

Asp Ala Tyr Gly Asn Arg Pro Phe Ile Ala Gln Asp Gln Asn Ala
                    645                 650                 655

Pro Arg Val Pro Ala Ala Arg Leu Gly Phe His Leu Lys Ala Ser Leu
                660                 665                 670

Thr Asp Arg Ile Asp Ala Asn Leu Asp Tyr Tyr Arg Val Phe Ala Gln
                    675                 680                 685

Asn Lys Leu Ala Arg Tyr Glu Thr Arg Thr Pro Gly His His Met Leu
            690                 695                 700

Asn Leu Gly Ala Asn Tyr Arg Arg Asn Thr Arg Tyr Gly Glu Trp Asn
705                 710                 715                 720

Trp Tyr Val Lys Ala Asp Asn Leu Leu Asn Gln Ser Val Tyr Ala His
                    725                 730                 735

Ser Ser Phe Leu Ser Asp Thr Pro Gln Met Gly Arg Ser Phe Thr Gly
                740                 745                 750

Gly Val Asn Val Lys Phe
                755

<210> SEQ ID NO 20
<211> LENGTH: 758
<212> TYPE: PRT
<213> ORGANISM: Neisseria meningitidis

<400> SEQUENCE: 20

Met Ala Gln Thr Thr Leu Lys Pro Ile Val Leu Ser Ile Leu Leu Ile
1               5                   10                  15

Asn Thr Pro Leu Leu Ala Gln Ala His Glu Thr Glu Gln Ser Val Gly
                20                  25                  30

Leu Glu Thr Val Thr Val Val Gly Lys Ser Arg Pro Arg Ala Thr Ser
            35                  40                  45

Gly Leu Leu His Thr Ser Thr Ala Ser Asp Lys Ile Ile Ser Gly Asp
        50                  55                  60

Thr Leu Arg Gln Lys Ala Val Asn Leu Gly Asp Ala Leu Asp Gly Val
65                  70                  75                  80

Pro Gly Ile His Ala Ser Gln Tyr Gly Gly Gly Ala Ser Ala Pro Val
                85                  90                  95

Ile Arg Gly Gln Thr Gly Arg Arg Ile Lys Val Leu Asn His His Gly
                100                 105                 110

Glu Thr Gly Asp Met Ala Asp Phe Ser Pro Asp His Ala Ile Met Val
            115                 120                 125

Asp Thr Ala Leu Ser Gln Gln Val Glu Ile Leu Arg Gly Pro Val Thr
        130                 135                 140

Leu Leu Tyr Ser Ser Gly Asn Val Ala Gly Leu Val Asp Val Ala Asp
145                 150                 155                 160
```

```
Gly Lys Ile Pro Glu Lys Met Pro Glu Asn Gly Val Ser Gly Glu Leu
            165                 170                 175
Gly Leu Arg Leu Ser Ser Gly Asn Leu Glu Lys Leu Thr Ser Gly Gly
        180                 185                 190
Ile Asn Ile Gly Leu Gly Lys Asn Phe Val Leu His Thr Glu Gly Leu
        195                 200                 205
Tyr Arg Lys Ser Gly Asp Tyr Ala Val Pro Arg Tyr Arg Asn Leu Lys
    210                 215                 220
Arg Leu Pro Asp Ser His Ala Asp Ser Lys Thr Gly Ser Ile Gly Leu
225                 230                 235                 240
Ser Trp Val Gly Glu Lys Gly Phe Ile Gly Ala Ala Tyr Ser Asp Arg
                245                 250                 255
Arg Asp Gln Tyr Gly Leu Pro Ala His Ser His Glu Tyr Asp Asp Cys
            260                 265                 270
His Ala Asp Ile Ile Trp Gln Lys Ser Leu Ile Asn Lys Arg Tyr Leu
        275                 280                 285
Gln Leu Tyr Pro His Leu Leu Thr Glu Glu Asp Val Asp Tyr Asp Asn
    290                 295                 300
Pro Gly Leu Ser Cys Gly Phe His Asp Asp Asn Ala His Ala His
305                 310                 315                 320
Thr His Asn Gly Lys Pro Trp Ile Asp Leu Arg Asn Lys Arg Tyr Glu
                325                 330                 335
Leu Arg Ala Glu Trp Lys Gln Pro Leu Pro Gly Phe Glu Ala Leu Arg
            340                 345                 350
Val His Leu Asn Arg Asn Asp Tyr His His Asp Glu Lys Ala Gly Asp
        355                 360                 365
Ala Val Glu Asn Phe Phe Asn Asn Lys Thr Gln Asn Ala Arg Ile Glu
    370                 375                 380
Leu Arg His Gln Pro Ile Gly Arg Leu Lys Gly Ser Trp Gly Val Gln
385                 390                 395                 400
Tyr Leu Gln Gln Lys Ser Ser Ala Leu Ser Ala Ile Ser Glu Ala Val
                405                 410                 415
Lys Gln Pro Met Leu Leu Asp Asn Lys Val Gln His Tyr Ser Phe Phe
            420                 425                 430
Gly Val Glu Gln Ala Glu Trp Asp Asn Phe Thr Leu Glu Gly Gly Val
        435                 440                 445
Arg Val Glu Lys Gln Lys Ala Ser Ile Gln Tyr Asp Lys Ala Leu Ile
    450                 455                 460
Asp Arg Glu Asn Tyr Tyr Lys Gln Pro Leu Pro Asp Leu Gly Ala His
465                 470                 475                 480
Arg Gln Thr Ala Arg Ser Phe Ala Leu Ser Gly Asn Trp Tyr Phe Thr
                485                 490                 495
Pro Gln His Lys Leu Ser Leu Thr Ala Ser His Gln Glu Arg Leu Pro
            500                 505                 510
Ser Thr Gln Glu Leu Tyr Ala His Gly Lys His Val Ala Thr Asn Thr
        515                 520                 525
Phe Glu Val Gly Asn Lys His Leu Asn Lys Glu Arg Ser Asn Asn Ile
    530                 535                 540
Glu Leu Ala Leu Gly Tyr Glu Gly Asp Arg Trp Gln Tyr Asn Leu Ala
545                 550                 555                 560
Leu Tyr Arg Asn Arg Phe Gly Asn Tyr Ile Tyr Ala Gln Thr Leu Asn
                565                 570                 575
Asp Gly Arg Gly Pro Lys Ser Ile Glu Asp Asp Ser Glu Met Lys Leu
```

```
                      580                 585                 590
Val Arg Tyr Asn Gln Ser Gly Ala Asp Phe Tyr Gly Ala Glu Gly Glu
                595                 600                 605

Ile Tyr Phe Lys Pro Thr Pro Arg Tyr Arg Ile Gly Val Ser Gly Asp
            610                 615                 620

Tyr Val Arg Gly Arg Leu Lys Asn Leu Pro Ser Leu Pro Gly Arg Glu
625                 630                 635                 640

Asp Ala Tyr Gly Asn Arg Pro Phe Ile Ala Gln Asp Gln Asn Ala
                645                 650                 655

Pro Arg Val Pro Ala Ala Arg Leu Gly Val His Leu Lys Ala Ser Leu
            660                 665                 670

Thr Asp Arg Ile Asp Ala Asn Leu Asp Tyr Tyr Arg Val Phe Ala Gln
        675                 680                 685

Asn Lys Leu Ala Arg Tyr Glu Thr Arg Thr Pro Gly His His Met Leu
            690                 695                 700

Asn Leu Gly Ala Asn Tyr Arg Arg Asn Thr Arg Tyr Gly Glu Trp Asn
705                 710                 715                 720

Trp Tyr Val Lys Ala Asp Asn Leu Leu Asn Gln Ser Val Tyr Ala His
                725                 730                 735

Ser Ser Phe Leu Ser Asp Thr Pro Gln Met Gly Arg Ser Phe Thr Gly
            740                 745                 750

Gly Val Asn Val Lys Phe
            755

<210> SEQ ID NO 21
<211> LENGTH: 758
<212> TYPE: PRT
<213> ORGANISM: Neisseria meningitidis

<400> SEQUENCE: 21

Met Ala Gln Thr Thr Leu Lys Pro Ile Val Leu Ser Ile Leu Leu Ile
1               5                   10                  15

Asn Thr Pro Leu Leu Ser Gln Ala His Gly Thr Glu Gln Ser Val Gly
            20                  25                  30

Leu Glu Thr Val Ser Val Val Gly Lys Ser Arg Pro Arg Ala Thr Ser
        35                  40                  45

Gly Leu Leu His Thr Ser Thr Ala Ser Asp Lys Ile Ile Ser Gly Asp
    50                  55                  60

Thr Leu Arg Gln Lys Ala Val Asn Leu Gly Asp Ala Leu Asp Gly Val
65                  70                  75                  80

Pro Gly Ile His Ala Ser Gln Tyr Gly Gly Ala Ser Ala Pro Val
                85                  90                  95

Ile Arg Gly Gln Thr Gly Arg Arg Ile Lys Val Leu Asn His His Gly
            100                 105                 110

Glu Thr Gly Asp Met Ala Asp Phe Ser Pro Asp His Ala Ile Met Val
        115                 120                 125

Asp Ser Ala Leu Ser Gln Gln Val Glu Ile Leu Arg Gly Pro Val Thr
    130                 135                 140

Leu Leu Tyr Ser Ser Gly Asn Val Ala Gly Leu Val Asp Val Ala Asp
145                 150                 155                 160

Gly Lys Ile Pro Glu Lys Met Pro Glu Asn Gly Val Ser Gly Glu Leu
                165                 170                 175

Gly Leu Arg Leu Ser Ser Gly Asn Leu Glu Lys Leu Thr Ser Gly Gly
            180                 185                 190
```

```
Ile Asn Ile Gly Leu Gly Lys Asn Phe Val Leu His Thr Glu Gly Leu
            195                 200                 205

Tyr Arg Lys Ser Gly Asp Tyr Ala Val Pro Arg Tyr Arg Asn Leu Lys
    210                 215                 220

Arg Leu Pro Asp Ser His Ala Asp Ser Gln Thr Gly Ser Ile Gly Leu
225                 230                 235                 240

Ser Trp Val Gly Glu Lys Gly Phe Ile Gly Ala Ala Tyr Ser Asp Arg
                245                 250                 255

Arg Asp Gln Tyr Gly Leu Pro Ala Ser His Glu Tyr Asp Asp Cys
                260                 265                 270

His Ala Asp Ile Ile Trp Gln Lys Ser Leu Ile Asn Lys Arg Tyr Leu
            275                 280                 285

Gln Leu Tyr Pro His Leu Leu Thr Glu Glu Asp Ile Asp Tyr Asp Asn
        290                 295                 300

Pro Gly Leu Ser Cys Gly Phe His Asp Asp Asp Ala His Ala His
305                 310                 315                 320

Ala His Asn Gly Lys Pro Trp Ile Asp Leu Arg Asn Lys Arg Tyr Glu
                325                 330                 335

Leu Arg Ala Glu Trp Lys Gln Pro Phe Pro Gly Phe Glu Ala Leu Arg
            340                 345                 350

Val His Leu Asn Arg Asn Asp Tyr Arg His Asp Glu Lys Ala Gly Asp
        355                 360                 365

Ala Val Glu Asn Phe Phe Asn Asn Gln Thr Gln Asn Ala Arg Ile Glu
    370                 375                 380

Leu Arg His Gln Pro Ile Gly Arg Leu Lys Gly Ser Trp Gly Val Gln
385                 390                 395                 400

Tyr Leu Gly Gln Lys Ser Ser Ala Leu Ser Ala Thr Ser Glu Ala Val
                405                 410                 415

Lys Gln Pro Met Leu Leu Asp Asn Lys Val Gln His Tyr Ser Phe Phe
            420                 425                 430

Gly Val Glu Gln Ala Asn Trp Asp Asn Phe Thr Leu Glu Gly Gly Val
        435                 440                 445

Arg Val Glu Lys Gln Lys Ala Ser Ile Arg Tyr Asp Lys Ala Leu Ile
    450                 455                 460

Asp Arg Glu Asn Tyr Tyr Asn His Pro Leu Pro Asp Leu Gly Ala His
465                 470                 475                 480

Arg Gln Thr Ala Arg Ser Phe Ala Leu Ser Gly Asn Trp Tyr Phe Thr
                485                 490                 495

Pro Gln His Lys Leu Ser Leu Thr Ala Ser His Gln Glu Arg Leu Pro
            500                 505                 510

Ser Thr Gln Glu Leu Tyr Ala His Gly Lys His Val Ala Thr Asn Thr
        515                 520                 525

Phe Glu Val Gly Asn Lys His Leu Asn Lys Glu Arg Ser Asn Asn Ile
    530                 535                 540

Glu Leu Ala Leu Gly Tyr Glu Gly Asp Arg Trp Gln Tyr Asn Leu Ala
545                 550                 555                 560

Leu Tyr Arg Asn Arg Phe Gly Asn Tyr Ile Tyr Ala Gln Thr Leu Asn
                565                 570                 575

Asp Gly Arg Gly Pro Lys Ser Ile Glu Asp Ser Glu Met Lys Leu
            580                 585                 590

Val Arg Tyr Asn Gln Ser Gly Ala Asp Phe Tyr Gly Ala Glu Gly Glu
        595                 600                 605

Ile Tyr Phe Lys Pro Thr Pro Arg Tyr Arg Ile Gly Val Ser Gly Asp
```

```
                610                 615                 620
Tyr Val Arg Gly Arg Leu Lys Asn Leu Pro Ser Leu Pro Gly Arg Glu
625                 630                 635                 640

Asp Ala Tyr Gly Asn Arg Pro Leu Ile Ala Gln Ala Asp Gln Asn Ala
            645                 650                 655

Pro Arg Val Pro Ala Ala Arg Leu Gly Val His Leu Lys Ala Ser Leu
        660                 665                 670

Thr Asp Arg Ile Asp Ala Asn Leu Asp Tyr Tyr Arg Val Phe Ala Gln
            675                 680                 685

Asn Lys Leu Ala Arg Tyr Glu Thr Arg Thr Pro Gly His His Met Leu
690                 695                 700

Asn Leu Gly Ala Asn Tyr Arg Arg Asn Thr Arg Tyr Gly Glu Trp Asn
705                 710                 715                 720

Trp Tyr Val Lys Ala Asp Asn Leu Leu Asn Gln Ser Val Tyr Ala His
                725                 730                 735

Ser Ser Phe Leu Ser Asp Thr Pro Gln Met Gly Arg Ser Phe Thr Gly
            740                 745                 750

Gly Val Asn Val Lys Phe
            755

<210> SEQ ID NO 22
<211> LENGTH: 758
<212> TYPE: PRT
<213> ORGANISM: Neisseria meningitidis

<400> SEQUENCE: 22

Met Ala Gln Thr Thr Leu Lys Pro Ile Val Leu Ser Ile Leu Leu Ile
1               5                   10                  15

Asn Thr Pro Leu Leu Ala Gln Ala His Glu Thr Glu Gln Ser Val Asp
            20                  25                  30

Leu Glu Thr Val Ser Val Val Gly Lys Ser Arg Pro Arg Ala Thr Ser
        35                  40                  45

Gly Leu Leu His Thr Ser Thr Ala Ser Asp Lys Ile Leu Ser Gly Asp
    50                  55                  60

Thr Leu Arg Gln Lys Ala Val Asn Leu Gly Asp Ala Leu Asp Gly Val
65                  70                  75                  80

Pro Gly Ile His Ala Ser Gln Tyr Gly Gly Gly Ala Ser Ala Pro Val
                85                  90                  95

Ile Arg Gly Gln Thr Gly Arg Arg Ile Lys Val Leu Asn His His Gly
            100                 105                 110

Glu Thr Gly Asp Met Ala Asp Phe Ser Pro Asp His Ala Ile Met Val
        115                 120                 125

Asp Thr Ala Leu Ser Gln Gln Val Glu Ile Leu Arg Gly Pro Val Thr
    130                 135                 140

Leu Leu Tyr Ser Ser Gly Asn Val Ala Gly Leu Val Asp Val Ala Asp
145                 150                 155                 160

Gly Lys Ile Pro Glu Lys Met Pro Glu Asn Gly Val Ser Gly Glu Leu
                165                 170                 175

Gly Leu Arg Leu Ser Ser Gly Asn Leu Glu Lys Leu Thr Ser Gly Gly
            180                 185                 190

Ile Asn Ile Gly Leu Gly Lys Asn Phe Val Leu His Thr Glu Gly Leu
        195                 200                 205

Tyr Arg Lys Ser Gly Asp Tyr Ala Val Pro Arg Tyr Arg Asn Leu Lys
    210                 215                 220
```

```
Arg Leu Pro Asp Ser His Ala Asp Ser Gln Thr Gly Ser Ile Gly Leu
225                 230                 235                 240

Ser Trp Val Gly Glu Lys Gly Phe Ile Gly Val Ala Tyr Ser Asp Arg
            245                 250                 255

Arg Asp Gln Tyr Gly Leu Pro Ala His Ser His Glu Tyr Asp Asp Cys
        260                 265                 270

His Ala Asp Ile Ile Trp Gln Lys Ser Leu Ile Asn Lys Arg Tyr Leu
    275                 280                 285

Gln Leu Tyr Pro His Leu Leu Thr Glu Glu Asp Ile Asp Tyr Asp Asn
290                 295                 300

Pro Gly Leu Ser Cys Gly Phe His Asp Asp Asp Ala His Ala His
305                 310                 315                 320

Thr His Ser Gly Arg Pro Trp Ile Asp Leu Arg Asn Lys Arg Tyr Glu
            325                 330                 335

Leu Arg Ala Glu Trp Lys Gln Pro Phe Pro Gly Phe Glu Ala Leu Arg
        340                 345                 350

Val His Leu Asn Arg Asn Asp Tyr Arg His Asp Glu Lys Ala Gly Asp
    355                 360                 365

Ala Val Glu Asn Phe Phe Asn Asn Gln Thr Gln Asn Ala Arg Ile Glu
370                 375                 380

Leu Arg His Gln Pro Ile Gly Arg Leu Lys Gly Ser Trp Gly Val Gln
385                 390                 395                 400

Tyr Leu Gln Gln Lys Ser Ser Ala Leu Ser Ala Ile Ser Glu Ala Val
            405                 410                 415

Lys Gln Pro Met Leu Leu Asp Asn Lys Val Gln His Tyr Ser Phe Phe
        420                 425                 430

Gly Val Glu Gln Ala Asn Trp Asp Asn Phe Thr Leu Glu Gly Gly Val
    435                 440                 445

Arg Val Glu Lys Gln Lys Ala Ser Ile Arg Tyr Asp Lys Ala Leu Ile
450                 455                 460

Asp Arg Glu Asn Tyr Tyr Asn His Pro Leu Pro Asp Leu Gly Ala His
465                 470                 475                 480

Arg Gln Thr Ala Arg Ser Phe Ala Leu Ser Gly Asn Trp Tyr Phe Thr
            485                 490                 495

Pro Gln His Lys Leu Ser Leu Thr Ala Ser His Gln Glu Arg Leu Pro
        500                 505                 510

Ser Thr Gln Glu Leu Tyr Ala His Gly Lys His Val Ala Thr Asn Thr
    515                 520                 525

Phe Glu Val Gly Asn Lys His Leu Asn Lys Arg Ser Asn Asn Ile
530                 535                 540

Glu Leu Ala Leu Gly Tyr Glu Gly Asp Arg Trp Gln Tyr Asn Leu Ala
545                 550                 555                 560

Leu Tyr Arg Asn Arg Phe Gly Asn Tyr Ile Tyr Ala Gln Thr Leu Asn
            565                 570                 575

Asp Gly Arg Gly Pro Lys Ser Ile Glu Asp Ser Glu Met Lys Leu
        580                 585                 590

Val Arg Tyr Asn Gln Ser Gly Ala Asp Phe Tyr Gly Ala Glu Gly Glu
    595                 600                 605

Ile Tyr Phe Lys Pro Thr Pro Arg Tyr Arg Ile Gly Val Ser Gly Asp
610                 615                 620

Tyr Val Arg Gly Arg Leu Lys Asn Leu Pro Ser Leu Pro Gly Arg Glu
625                 630                 635                 640

Asp Ala Tyr Gly Asn Arg Pro Phe Ile Ala Gln Asp Asp Gln Asn Ala
```

```
                   645                 650                 655
Pro Arg Val Pro Ala Arg Leu Gly Val His Leu Lys Ala Ser Leu
            660                 665                 670

Thr Asp Arg Ile Asp Ala Asn Leu Asp Tyr Tyr Arg Val Phe Ala Gln
            675                 680                 685

Asn Lys Leu Ala Arg Tyr Glu Thr Arg Thr Pro Gly His His Met Leu
690                 695                 700

Asn Leu Gly Ala Asn Tyr Arg Arg Asn Thr Arg Tyr Gly Glu Trp Asn
705                 710                 715                 720

Trp Tyr Val Lys Ala Asp Asn Leu Leu Asn Gln Ser Val Tyr Ala His
                725                 730                 735

Ser Ser Phe Leu Ser Asp Thr Pro Gln Met Gly Arg Ser Phe Thr Gly
            740                 745                 750

Gly Val Asn Val Lys Phe
            755

<210> SEQ ID NO 23
<211> LENGTH: 758
<212> TYPE: PRT
<213> ORGANISM: Neisseria meningitidis

<400> SEQUENCE: 23

Met Ala Gln Thr Thr Leu Lys Pro Ile Val Leu Ser Ile Leu Leu Ile
1               5                   10                  15

Asn Thr Pro Leu Leu Ala Gln Ala His Glu Thr Glu Gln Ser Val Asp
            20                  25                  30

Leu Glu Thr Val Ser Val Val Gly Lys Ser Arg Pro Arg Ala Thr Ser
        35                  40                  45

Gly Leu Leu His Thr Ser Thr Ala Ser Asp Lys Ile Ile Ser Gly Asp
    50                  55                  60

Thr Leu Arg Gln Lys Ala Val Asn Leu Gly Asp Ala Leu Asp Gly Val
65                  70                  75                  80

Pro Gly Ile His Ala Ser Gln Tyr Gly Gly Ala Ser Ala Pro Val
                85                  90                  95

Ile Arg Gly Gln Thr Gly Arg Arg Ile Lys Val Leu Asn His His Gly
            100                 105                 110

Glu Thr Gly Asp Met Ala Asp Phe Ser Pro Asp His Ala Ile Met Val
        115                 120                 125

Asp Thr Ala Leu Ser Gln Gln Val Glu Ile Leu Arg Gly Pro Val Thr
130                 135                 140

Leu Leu Tyr Ser Ser Gly Asn Val Ala Gly Leu Val Asp Val Ala Asp
145                 150                 155                 160

Gly Lys Ile Pro Glu Lys Met Pro Glu Asn Gly Val Ser Gly Glu Leu
                165                 170                 175

Gly Leu Arg Leu Ser Ser Gly Asn Leu Glu Lys Leu Thr Ser Gly Gly
            180                 185                 190

Ile Asn Ile Gly Leu Gly Lys Asn Phe Val Leu His Thr Glu Gly Leu
        195                 200                 205

Tyr Arg Lys Ser Gly Asp Tyr Ala Val Pro Arg Tyr Arg Asn Leu Lys
210                 215                 220

Arg Leu Pro Asp Ser His Ala Asp Ser Gln Thr Gly Ser Ile Gly Leu
225                 230                 235                 240

Ser Trp Val Gly Glu Lys Gly Phe Ile Gly Val Ala Tyr Ser Asp Arg
                245                 250                 255
```

```
Arg Asp Gln Tyr Gly Leu Pro Ala His Ser His Glu Tyr Asp Asp Cys
            260                 265                 270
His Ala Asp Ile Ile Trp Gln Lys Ser Leu Ile Asn Lys Arg Tyr Leu
        275                 280                 285
Gln Leu Tyr Pro His Leu Leu Thr Glu Glu Asp Val Asp Tyr Asp Asn
    290                 295                 300
Pro Gly Leu Ser Cys Gly Phe His Asp Asp Asp Ala His Ala His
305                 310                 315                 320
Ala His Asn Gly Lys Pro Trp Ile Asp Leu Arg Asn Lys Arg Tyr Glu
                325                 330                 335
Leu Arg Ala Glu Trp Lys Gln Pro Phe Pro Gly Phe Glu Ala Leu Arg
            340                 345                 350
Val His Leu Asn Arg Asn Asp Tyr Arg His Asp Glu Lys Ala Gly Asp
        355                 360                 365
Ala Val Glu Asn Phe Phe Asn Asn Gln Thr Gln Asn Ala Arg Ile Glu
    370                 375                 380
Leu Arg His Gln Pro Ile Gly Arg Leu Lys Gly Ser Trp Gly Val Gln
385                 390                 395                 400
Tyr Leu Gln Gln Lys Ser Ser Ala Leu Ser Ala Thr Ser Glu Ala Val
                405                 410                 415
Lys Gln Pro Met Leu Leu Asp Asn Lys Val Gln His Tyr Ser Phe Phe
            420                 425                 430
Gly Val Glu Gln Ala Asn Trp Asp Asn Phe Thr Leu Glu Gly Gly Val
        435                 440                 445
Arg Val Glu Lys Gln Lys Ala Ser Ile Arg Tyr Asp Lys Ala Leu Ile
    450                 455                 460
Asp Arg Glu Asn Tyr Tyr Asn His Pro Leu Pro Asp Leu Gly Ala His
465                 470                 475                 480
Arg Gln Thr Ala Arg Ser Phe Ala Leu Ser Gly Asn Trp Tyr Phe Thr
                485                 490                 495
Pro Gln His Lys Leu Ser Leu Thr Ala Ser His Gln Glu Arg Leu Pro
            500                 505                 510
Ser Thr Gln Glu Leu Tyr Ala His Gly Lys His Val Ala Thr Asn Thr
        515                 520                 525
Phe Glu Val Gly Asn Lys His Leu Asn Lys Glu Arg Ser Asn Asn Ile
    530                 535                 540
Glu Leu Ala Leu Gly Tyr Glu Gly Asp Arg Trp Gln Tyr Asn Leu Ala
545                 550                 555                 560
Leu Tyr Arg Asn Arg Phe Gly Asn Tyr Ile Tyr Ala Gln Thr Leu Asn
                565                 570                 575
Asp Gly Arg Gly Pro Lys Ser Ile Glu Asp Asp Ser Glu Met Lys Leu
            580                 585                 590
Val Arg Tyr Asn Gln Ser Gly Ala Asp Phe Tyr Gly Ala Glu Gly Glu
        595                 600                 605
Ile Tyr Phe Lys Pro Thr Pro Arg Tyr Arg Ile Gly Val Ser Gly Asp
    610                 615                 620
Tyr Val Arg Gly Arg Leu Lys Asn Leu Pro Ser Leu Pro Gly Arg Glu
625                 630                 635                 640
Asp Ala Tyr Gly Asn Arg Pro Phe Ile Ala Gln Asp Gln Asn Ala
                645                 650                 655
Pro Arg Val Pro Ala Ala Arg Leu Gly Val His Leu Lys Ala Ser Leu
            660                 665                 670
Thr Asp Arg Ile Asp Ala Asn Leu Asp Tyr Tyr Arg Val Phe Ala Gln
```

```
                   675                 680                 685
Asn Lys Leu Ala Arg Tyr Glu Thr Arg Thr Pro Gly His His Met Leu
    690                 695                 700

Asn Leu Gly Ala Asn Tyr Arg Arg Asn Thr Arg Tyr Gly Glu Trp Asn
705                 710                 715                 720

Trp Tyr Val Lys Ala Asp Asn Leu Leu Asn Gln Ser Val Tyr Ala His
                725                 730                 735

Ser Ser Phe Leu Ser Asp Thr Pro Gln Met Gly Arg Ser Phe Thr Gly
                740                 745                 750

Gly Val Asn Val Lys Phe
            755

<210> SEQ ID NO 24
<211> LENGTH: 758
<212> TYPE: PRT
<213> ORGANISM: Neisseria meningitidis

<400> SEQUENCE: 24

Met Ala Gln Thr Thr Leu Lys Pro Ile Val Leu Ser Ile Leu Leu Ile
1               5                   10                  15

Asn Thr Pro Leu Leu Ala Gln Ala His Glu Thr Asp Arg Ser Val Asp
            20                  25                  30

Leu Glu Thr Val Ser Val Val Gly Lys Ser Arg Pro Arg Ala Thr Ser
        35                  40                  45

Gly Leu Leu His Thr Ser Thr Ala Ser Asp Lys Ile Ile Ser Gly Asp
    50                  55                  60

Thr Leu Arg Gln Lys Ala Val Asn Leu Gly Asp Ala Leu Asp Gly Val
65                  70                  75                  80

Pro Gly Ile His Ala Ser Gln Tyr Gly Gly Gly Ala Ser Ala Pro Val
                85                  90                  95

Ile Arg Gly Gln Thr Gly Arg Arg Ile Lys Val Leu Asn His His Gly
            100                 105                 110

Glu Thr Gly Asp Met Ala Asp Phe Ser Pro Asp His Ala Ile Met Val
        115                 120                 125

Asp Thr Ala Leu Ser Gln Gln Val Glu Ile Leu Arg Gly Pro Val Thr
    130                 135                 140

Leu Leu Tyr Ser Ser Gly Asn Val Ala Gly Leu Val Asp Val Ala Asp
145                 150                 155                 160

Gly Lys Ile Pro Glu Lys Met Pro Glu Asn Gly Val Ser Gly Glu Leu
                165                 170                 175

Gly Leu Arg Leu Ser Ser Gly Asn Leu Glu Lys Leu Thr Ser Gly Gly
            180                 185                 190

Ile Asn Ile Gly Leu Gly Lys Asn Phe Val Leu His Thr Glu Gly Leu
        195                 200                 205

Tyr Arg Lys Ser Gly Asp Tyr Ala Val Pro Arg Tyr Arg Asn Leu Lys
    210                 215                 220

Arg Leu Pro Asp Ser His Ala Asp Ser Gln Thr Gly Ser Ile Gly Leu
225                 230                 235                 240

Ser Trp Val Gly Glu Lys Gly Phe Ile Gly Ala Ala Tyr Ser Asp Arg
                245                 250                 255

Arg Asp Gln Tyr Gly Leu Pro Ala His Ser His Glu Tyr Asp Asp Cys
            260                 265                 270

His Ala Asp Ile Ile Trp Gln Lys Ser Leu Ile Asn Lys Arg Tyr Leu
        275                 280                 285
```

-continued

```
Gln Leu Tyr Pro His Leu Leu Thr Glu Glu Asp Ile Asp Tyr Asp Asn
    290                 295                 300
Pro Gly Leu Ser Cys Gly Phe His Asp Asp Asp Ala His Ala His
305                 310                 315                 320
Ala His Asn Gly Lys Pro Trp Ile Asp Leu Arg Asn Lys Arg Tyr Glu
                325                 330                 335
Leu Arg Ala Glu Trp Lys Gln Pro Phe Pro Gly Phe Glu Ala Leu Arg
            340                 345                 350
Val His Leu Asn Arg Asn Asp Tyr Arg His Asp Glu Lys Ala Gly Asp
        355                 360                 365
Ala Val Glu Asn Phe Phe Asn Asn Gln Thr Gln Asn Ala Arg Ile Glu
370                 375                 380
Leu Arg His Gln Pro Ile Gly Arg Leu Lys Gly Ser Trp Gly Val Gln
385                 390                 395                 400
Tyr Leu Gln Gln Lys Ser Ser Ala Leu Ser Ala Thr Ser Glu Ala Val
                405                 410                 415
Lys Gln Pro Met Leu Leu Asp Asn Lys Val Gln His Tyr Ser Phe Phe
            420                 425                 430
Gly Val Glu Gln Ala Asn Trp Asp Asn Phe Thr Leu Glu Gly Gly Val
        435                 440                 445
Arg Val Glu Lys Gln Lys Ala Ser Ile Arg Tyr Asp Lys Ala Leu Ile
450                 455                 460
Asp Arg Glu Asn Tyr Tyr Asn His Pro Leu Pro Asp Leu Gly Ala His
465                 470                 475                 480
Arg Gln Thr Ala Arg Ser Phe Ala Leu Ser Gly Asn Trp Tyr Phe Thr
                485                 490                 495
Pro Gln His Lys Leu Ser Leu Thr Ala Ser His Gln Glu Arg Leu Pro
            500                 505                 510
Ser Thr Gln Glu Leu Tyr Ala His Gly Lys His Val Ala Thr Asn Thr
        515                 520                 525
Phe Glu Val Gly Asn Lys His Leu Asn Lys Glu Arg Ser Asn Asn Ile
530                 535                 540
Glu Leu Ala Leu Gly Tyr Glu Gly Asp Arg Trp Gln Tyr Asn Leu Ala
545                 550                 555                 560
Leu Tyr Arg Asn Arg Phe Gly Asn Tyr Ile Tyr Ala Gln Thr Leu Asn
                565                 570                 575
Asp Gly Arg Gly Pro Lys Ser Ile Glu Asp Asp Ser Glu Met Lys Leu
            580                 585                 590
Val Arg Tyr Asn Gln Ser Gly Ala Asp Phe Tyr Gly Ala Glu Gly Glu
        595                 600                 605
Ile Tyr Phe Lys Pro Thr Pro Arg Tyr Arg Ile Gly Val Ser Gly Asp
610                 615                 620
Tyr Val Arg Gly Arg Leu Lys Asn Leu Pro Ser Leu Pro Gly Arg Glu
625                 630                 635                 640
Asp Ala Tyr Gly Asn Arg Pro Phe Ile Ala Gln Asp Gln Asn Ala
                645                 650                 655
Pro Arg Val Pro Ala Ala Arg Leu Gly Val His Leu Lys Ala Ser Leu
            660                 665                 670
Thr Asp Arg Ile Asp Ala Asn Leu Asp Tyr Tyr Arg Val Phe Ala Gln
        675                 680                 685
Asn Lys Leu Ala Arg Tyr Glu Thr Arg Thr Pro Gly His His Met Leu
690                 695                 700
Asn Leu Gly Ala Asn Tyr Arg Arg Asn Thr Arg Tyr Gly Glu Trp Asn
```

```
                705                 710                 715                 720
Trp Tyr Val Lys Ala Asp Asn Leu Leu Asn Gln Ser Val Tyr Ala His
                    725                 730                 735

Ser Ser Phe Leu Ser Asp Thr Pro Gln Met Gly Arg Ser Phe Thr Gly
                    740                 745                 750

Gly Val Asn Val Lys Phe
            755

<210> SEQ ID NO 25
<211> LENGTH: 728
<212> TYPE: PRT
<213> ORGANISM: Neisseria meningitidis

<400> SEQUENCE: 25

Val Asp Leu Glu Thr Val Ser Val Val Gly Lys Ser Arg Pro Arg Ala
1               5                   10                  15

Thr Ser Gly Leu Leu His Thr Ser Thr Ala Ser Asp Lys Ile Ile Ser
                20                  25                  30

Gly Asp Thr Leu Arg Gln Lys Ala Val Asn Leu Gly Asp Ala Leu Asp
            35                  40                  45

Gly Val Pro Gly Ile His Ala Ser Gln Tyr Gly Gly Ala Ser Ala
        50                  55                  60

Pro Val Ile Arg Gly Gln Thr Gly Arg Arg Ile Lys Val Leu Asn His
65                  70                  75                  80

His Gly Glu Thr Gly Asp Met Ala Asp Phe Ser Pro Asp His Ala Ile
                85                  90                  95

Met Val Asp Ser Ala Leu Ser Gln Gln Val Glu Ile Leu Arg Gly Pro
            100                 105                 110

Val Thr Leu Leu Tyr Ser Ser Gly Asn Val Ala Gly Leu Val Asp Val
        115                 120                 125

Ala Asp Gly Lys Ile Pro Glu Lys Met Pro Glu Asn Gly Val Ser Gly
    130                 135                 140

Glu Leu Gly Leu Arg Leu Ser Ser Gly Asn Leu Glu Lys Leu Thr Ser
145                 150                 155                 160

Gly Gly Ile Asn Ile Gly Leu Gly Lys Asn Phe Val Leu His Thr Glu
                165                 170                 175

Gly Leu Tyr Arg Lys Ser Gly Asp Tyr Ala Val Pro Arg Tyr Arg Asn
            180                 185                 190

Leu Lys Arg Leu Pro Asp Ser His Ala Asp Ser Gln Thr Gly Ser Ile
        195                 200                 205

Gly Leu Ser Trp Val Gly Glu Lys Gly Phe Ile Gly Ala Ala Tyr Ser
    210                 215                 220

Asp Arg Arg Asp Gln Tyr Gly Leu Pro Ala His Ser His Glu Tyr Asp
225                 230                 235                 240

Asp Cys His Ala Asp Ile Ile Trp Gln Lys Ser Leu Ile Asn Lys Arg
                245                 250                 255

Tyr Leu Gln Leu Tyr Pro His Leu Leu Thr Glu Glu Asp Ile Asp Tyr
            260                 265                 270

Asp Asn Pro Gly Leu Ser Cys Gly Phe His Asp Asp Asp Ala His
        275                 280                 285

Ala His Ala His Asn Gly Lys Pro Trp Ile Asp Leu Arg Asn Lys Arg
    290                 295                 300

Tyr Glu Leu Arg Ala Glu Trp Lys Gln Pro Phe Pro Gly Phe Glu Ala
305                 310                 315                 320
```

```
Leu Arg Val His Leu Asn Arg Asn Asp Tyr His His Asp Glu Lys Ala
            325                 330                 335

Gly Asp Ala Val Glu Asn Phe Phe Asn Asn Gln Thr Gln Asn Ala Arg
            340                 345                 350

Ile Glu Leu Arg His Gln Pro Ile Gly Arg Leu Lys Gly Ser Trp Gly
            355                 360                 365

Val Gln Tyr Leu Gly Gln Lys Ser Ser Ala Leu Ser Ala Thr Ser Glu
            370                 375                 380

Ala Val Lys Gln Pro Met Leu Leu Asp Asn Lys Val Gln His Tyr Ser
385                 390                 395                 400

Phe Phe Gly Val Glu Gln Ala Asn Trp Asp Asn Phe Thr Leu Glu Gly
                405                 410                 415

Gly Val Arg Val Glu Lys Gln Lys Ala Ser Ile Arg Tyr Asp Lys Ala
            420                 425                 430

Leu Ile Asp Arg Glu Asn Tyr Tyr Asn His Pro Leu Pro Asp Leu Gly
            435                 440                 445

Ala His Arg Gln Thr Ala Arg Ser Phe Ala Leu Ser Gly Asn Trp Tyr
            450                 455                 460

Phe Thr Pro Gln His Lys Leu Ser Leu Thr Ala Ser His Gln Glu Arg
465                 470                 475                 480

Leu Pro Ser Thr Gln Glu Leu Tyr Ala His Gly Lys His Val Ala Thr
                485                 490                 495

Asn Thr Phe Glu Val Gly Asn Lys His Leu Asn Lys Glu Arg Ser Asn
            500                 505                 510

Asn Ile Glu Leu Ala Leu Gly Tyr Glu Gly Asp Arg Trp Gln Tyr Asn
            515                 520                 525

Leu Ala Leu Tyr Arg Asn Arg Phe Gly Asn Tyr Ile Tyr Ala Gln Thr
            530                 535                 540

Leu Asn Asp Gly Arg Gly Pro Lys Ser Ile Glu Asp Asp Ser Glu Met
545                 550                 555                 560

Lys Leu Val Arg Tyr Asn Gln Ser Gly Ala Asp Phe Tyr Gly Ala Glu
                565                 570                 575

Gly Glu Ile Tyr Phe Lys Pro Thr Pro Arg Tyr Arg Ile Gly Val Ser
            580                 585                 590

Gly Asp Tyr Val Arg Gly Arg Leu Lys Asn Leu Pro Ser Leu Pro Gly
            595                 600                 605

Arg Glu Asp Ala Tyr Gly Asn Arg Pro Phe Ile Ala Gln Asp Asp Gln
            610                 615                 620

Asn Ala Pro Arg Val Pro Ala Arg Leu Gly Val His Leu Lys Ala
625                 630                 635                 640

Ser Leu Thr Asp Arg Ile Asp Ala Asn Leu Asp Tyr Tyr Arg Val Phe
                645                 650                 655

Ala Gln Asn Lys Leu Ala Arg Tyr Glu Thr Arg Thr Pro Gly His His
            660                 665                 670

Met Leu Asn Leu Gly Ala Asn Tyr Arg Arg Asn Thr Arg Tyr Gly Glu
            675                 680                 685

Trp Asn Trp Tyr Val Lys Ala Asp Asn Leu Leu Asn Gln Ser Val Tyr
            690                 695                 700

Ala His Ser Ser Phe Leu Ser Asp Thr Pro Gln Met Gly Arg Ser Phe
705                 710                 715                 720

Thr Gly Gly Val Asn Val Lys Phe
            725
```

<210> SEQ ID NO 26
<211> LENGTH: 803
<212> TYPE: PRT
<213> ORGANISM: Acinetobacter baumannii

<400> SEQUENCE: 26

```
Met Leu Asn Lys Ser Lys Leu Phe Leu Ala Leu Ile Thr Leu Gly Ala
 1               5                  10                  15

Ser Lys Ile Leu Leu Ala Ala Glu Gly Pro Val Thr Thr Leu Asn Thr
            20                  25                  30

Ile Val Leu Thr Ala Gln Ser Asp Glu Leu Gly Ser Glu Leu Leu Gly
        35                  40                  45

Lys Ser Leu Asn Val Ser Asn Gln Phe Ile Asp Thr Ser Lys Leu Lys
 50                  55                  60

Gln Arg Ser Thr Thr Leu Gly Asp Ala Leu Gly Thr Glu Leu Gly Ile
 65                  70                  75                  80

His Ser Asn Gln Tyr Gly Gly Ala Ser Ala Pro Ile Ile Arg Gly
                 85                  90                  95

Gln Glu Gly Lys Arg Ile Lys Val Leu Gln Asn Asn Ala Asp Val Leu
                100                 105                 110

Asp Met Ser Asn Met Ser Pro Asp His Ala Val Thr Val Glu Pro Ser
            115                 120                 125

Leu Ala Lys Ser Ile Glu Ile Ile Arg Gly Ala Ser Thr Leu Leu Tyr
        130                 135                 140

Ser Ser Asn Ser Ala Ala Gly Val Val Asn Val Ile Asp Tyr Lys Ile
145                 150                 155                 160

Pro Thr Gln Met Pro Gln Asp Gly Leu Glu Gly Asn Thr Thr Leu Arg
                165                 170                 175

Phe Asn Thr Gly Ser Asn Glu Lys Leu Thr Thr Ala Gly Val Thr Val
            180                 185                 190

Gly Leu Ser Pro Arg Val Ala Leu Arg Ala Glu Gly Leu Tyr Arg Asn
        195                 200                 205

Ala Gly Asn Tyr Lys Thr Pro His Tyr Gln Ser Ser Ser Tyr Asn Ser
    210                 215                 220

Leu Glu Asp Leu Glu Asn Gln Asn Ile Val Tyr Lys Asn Leu Lys Tyr
225                 230                 235                 240

Leu Pro Glu Ser Trp Ala Glu Ser Arg Leu Gly Thr Leu Gly Leu Ser
                245                 250                 255

Trp Ile Asp Asp Asn Thr Tyr Leu Gly Val Ser Tyr Thr His Arg His
            260                 265                 270

Asp Glu Tyr Gly Leu Pro Ala His Ser His Leu Tyr Glu Gly Cys Gly
        275                 280                 285

Ala Ser Ala Ile Ser Ile Asn Thr Arg Ile Ser Gly Leu Lys Asn Tyr
    290                 295                 300

Leu Leu Tyr Tyr Pro Gln Leu Met Glu Glu Gln Asp Ile Asn Tyr Val
305                 310                 315                 320

Asn Pro Arg Pro Asp Cys His Gln His Asn His Ile His Glu Thr Thr
                325                 330                 335

Phe Ser His Asn Ala Pro Tyr Ile Asp Leu Asn Thr Arg Arg Tyr Asp
            340                 345                 350

Met Arg Gly Glu Phe Thr Gln Pro Phe Thr Gly Ile Asp Lys Ile Arg
        355                 360                 365

Thr Ser Leu Ser Tyr Ile Asp Tyr Phe His Asn Glu Leu Glu Gly Asp
    370                 375                 380
```

```
Lys Ile Thr Asn Phe Phe Lys Asn Thr Gly Lys Val Gly Arg Ile Glu
385                 390                 395                 400

Leu Ser His Gln Pro Leu Gly Glu Leu Thr Gly Ile Leu Gly Leu Gln
            405                 410                 415

Tyr Leu Glu Gln Asp Asn Ser Ala Leu Ser Pro Val His Ser Gln Glu
        420                 425                 430

Gly His Thr Thr Tyr Leu Asp Thr Gln Gln Leu Leu Asn Arg Asn Val
    435                 440                 445

Thr Lys Asn Phe Ser Val Phe Gly Leu Glu Lys Tyr Asn Trp Asn Asp
450                 455                 460

Phe Thr Phe Glu Leu Gly Ala Arg Ile Glu Lys Gln Lys Val Ser Met
465                 470                 475                 480

Asp Tyr Asp Ile Glu Lys Ile Lys Asp Ser Met Lys Pro Trp Pro Asn
            485                 490                 495

Lys Tyr Asn Ser Pro Tyr Val Glu Lys Asn Asn Lys Ile Arg Ala Gln
        500                 505                 510

Asn Leu Lys Ser Ile Leu Glu Ala Val Gln Pro Asn Lys Glu Thr Ala
    515                 520                 525

Phe Ser Tyr Ala Gly Thr Val His Trp Arg Phe Ala Pro Asn Tyr Ile
530                 535                 540

Leu Ser Leu Thr Gly Thr His Gln Glu Arg Leu Pro Asn Ala Gln Glu
545                 550                 555                 560

Met Tyr Thr His Gly Met His Leu Ala Thr Asn Ser Phe Glu Ile Gly
            565                 570                 575

Asn Arg Phe Leu Arg Lys Glu Lys Ser Asn Asn Leu Glu Ile Ser Leu
        580                 585                 590

Ala Tyr Lys Asp Asp Leu Leu Asp Tyr Gln Ile Ser Thr Tyr Tyr Tyr
    595                 600                 605

Asp Phe Asp Asn Tyr Ile Tyr Leu Gln Thr Leu Asn Glu Val Leu Gly
610                 615                 620

Thr Thr Lys Val Arg Asp Gln His Thr Leu Arg Ile Asn His Tyr Ser
625                 630                 635                 640

Gln Ser Ala Ala Asn Phe Tyr Gly Leu Glu Gly Asn Ile Gly Tyr Gln
            645                 650                 655

Phe Asn Ser Val Tyr His Gly Ser Leu Phe Gly Asp Tyr Val Lys Gly
        660                 665                 670

Arg Leu Thr Asn Leu Pro Asp Ala Val Ile Ala Tyr Asp Ile Trp Asn
    675                 680                 685

Arg Glu Pro Thr Leu Ala Pro Gln Lys Asp Arg Tyr Thr Pro Arg Leu
690                 695                 700

Pro Pro Ala Arg Leu Gly Thr Arg Leu Lys Ala Asp Phe Asp Glu Ser
705                 710                 715                 720

Leu Lys Gly Glu Ile Glu Tyr Tyr Arg Val Phe Lys Gln Asp Asn Ile
            725                 730                 735

Ser Lys Phe Glu Gln Val Thr Ser Gly Tyr Asn Met Leu Asn Met Thr
        740                 745                 750

Leu Ala Tyr Lys Asn Lys Leu Ser His Thr Glu Tyr Asp Leu Phe Phe
    755                 760                 765

Lys Ala Asn Asn Leu Leu Asp Gln Lys Val Tyr Ala His Glu Thr Phe
770                 775                 780

Leu Pro Tyr Ile Pro Gln Ile Gly Arg Asn Phe Ser Leu Gly Leu Asn
785                 790                 795                 800

Leu Asn Phe
```

<210> SEQ ID NO 27
<211> LENGTH: 790
<212> TYPE: PRT
<213> ORGANISM: Actinobacillus pleuropneumoniae

<400> SEQUENCE: 27

```
Met Phe Asn Lys Lys Leu Leu Ala Val Leu Ile Ser Ala Gln Phe Ser
 1               5                  10                  15

Pro Leu Val Trp Ala Asn Asn Asp Val Ala Val Leu Asp Glu Val
                20                  25                  30

Ser Val Val Gly Ser Thr Pro Ser Ile Ser Gln Gly Ser Glu Val Thr
            35                  40                  45

Leu Leu Lys Val Ser Asp Lys Ile Ile Ala Gly Lys Glu Phe Lys Lys
        50                  55                  60

Arg Ser Ala Thr Leu Gly Asn Ala Leu Ala Ala Glu Leu Gly Val His
 65                  70                  75                  80

Ser Asn Pro Phe Gly Gly Ala Ser Lys Pro Ile Ile Arg Gly Gln
                85                  90                  95

Glu Gly Ala Arg Ile Arg Ile Leu Gln Asn Gly Ser Asp Val Ile Asp
            100                 105                 110

Met Ser Asn Leu Ser Pro Asp His Ala Val Val Ala Asp Ser Leu Leu
        115                 120                 125

Ala Lys Gln Val Glu Ile Leu Arg Gly Ser Ser Thr Leu Leu Tyr Ala
    130                 135                 140

Ser Ser Ser Pro Ala Gly Ile Val Asn Val Val Asp Lys Arg Ile Pro
145                 150                 155                 160

Thr Glu Ile Pro Glu Lys Gly Tyr Glu Val Glu Leu Asn Ser Arg Phe
                165                 170                 175

Asp Thr Ala Ala Lys Glu Lys Val Gly Ala Leu Gly Ala Thr Phe Gly
            180                 185                 190

Ile Gly Lys His Ile Ala Val Arg Ala Glu Gly Leu Thr Arg His Ser
        195                 200                 205

Asp Asn Tyr Arg Val Pro Gly Ile Asn Leu Gly Glu Arg Leu Asn Tyr
    210                 215                 220

Val Pro Asp Thr Tyr Asn Lys Ser Lys Val Gly Thr Leu Gly Leu Ser
225                 230                 235                 240

Phe Val Gly Glu Gln Gly Tyr Ile Gly Ala Ser Tyr Ser Lys Arg Arg
                245                 250                 255

Asp Asn Tyr Gly Leu Pro Gly His Asn His Lys Phe Asp Phe Cys Ile
            260                 265                 270

Gly His Ile Tyr Gly Asn Lys Gln Gly Lys Tyr Ala Tyr Thr Tyr Leu
        275                 280                 285

Tyr Pro His Leu Ile Gly Glu Glu Asn Ile Gly Ser Asn Pro His Phe
    290                 295                 300

His Cys Gly Thr Asp His Ala Glu Asp Gly Thr His Ser His Asp Asn
305                 310                 315                 320

Pro Phe Gly His Asp His Asp His Thr His Pro Gly Pro Trp Val Asp
                325                 330                 335

Leu Glu Ser Lys Arg Phe Asp Val Lys Ala Glu Leu Arg Gln Pro Phe
            340                 345                 350

Lys Gly Ile Asp Lys Ile Lys Val Ser Tyr Ala Asp Ala Asp Tyr Tyr
        355                 360                 365

His Asp Glu Lys Asp Ala Gly Val Leu Ala Thr Arg Tyr His Lys Gln
```

```
              370                 375                 380
Leu Lys Lys Asp Gln Asp Tyr Gly Lys Pro Val Asn Ile Phe Lys Asn
385                 390                 395                 400

Arg Gly Lys Asn Ala Arg Leu Glu Ile Tyr His Ala Pro Leu Gly Gly
                405                 410                 415

Leu Thr Gly Val Trp Gly Val Gln Tyr Gln Thr Gln Lys Ser Ser Met
            420                 425                 430

His Ala Pro Lys Asp Arg Glu Val Lys Phe Pro Leu Val Glu Asn Thr
            435                 440                 445

Asn Lys Gln Met Ser Leu Phe Gly Ile Glu Gln Tyr Met Trp Asp Asn
450                 455                 460

Phe Ala Leu Glu Phe Ala Gly Arg Val Glu Lys Gln Lys Ile Glu Ile
465                 470                 475                 480

Glu Tyr Asp Arg Asn Glu Ile Lys Arg Leu Gln Asp His Tyr Arg Ile
                485                 490                 495

Ser Gly Gly Lys Gln Val Glu Pro Asp Leu Ser Pro Tyr Asn Gln Asn
            500                 505                 510

Ala Tyr Ala Tyr Ser Ser Thr Leu Asn Trp Phe Phe His Pro Asp Tyr
            515                 520                 525

Gln Leu Ser Phe Thr Ala Ser His Asn Glu Arg Phe Pro Thr Pro Met
530                 535                 540

Glu Leu Tyr Tyr His Gly Gln His Ile Ala Thr Asn Ser Phe Glu Tyr
545                 550                 555                 560

Gly Asn Lys Asp Leu Lys Lys Glu Gln Ser Asn Asn Val Glu Leu Gly
                565                 570                 575

Leu Gly Tyr Gln Thr Glu Arg Val Gly Tyr Lys Val Asn Val Tyr Tyr
            580                 585                 590

Asn His Phe Lys Asn Tyr Ile Tyr Asn Glu Asn Leu Phe Arg Glu Asn
            595                 600                 605

Gln Leu Phe Met Arg Arg Tyr Asn Gln Ala Lys Ala Arg Phe Tyr Gly
        610                 615                 620

Ile Glu Ala Glu Ala Ser Tyr Arg Phe Asn Asp Lys Tyr Gln Ala Thr
625                 630                 635                 640

Ile Phe Gly Asp Met Val Arg Gly Trp Leu Thr Asn Leu Pro Pro Leu
                645                 650                 655

Thr Val Asn Ser Asp Tyr Ser Val Phe Lys Tyr Leu Pro Lys Asp
            660                 665                 670

Ala Lys Pro Gly Glu Asp Tyr Leu Ile Tyr Arg Ala Asp Gln Asn Thr
            675                 680                 685

Pro Arg Thr Pro Pro Val Arg Leu Gly Phe Arg Phe Asn Ala Glu Phe
        690                 695                 700

Thr Pro Asn Trp Ser Gly Asp Leu Glu Leu Ile Arg Thr Phe Thr Gln
705                 710                 715                 720

Arg Arg Thr Ser Gln Leu Glu Tyr Ile Thr Glu Gly Asn Thr Met Leu
                725                 730                 735

Asn Ile Gly Val Ala Tyr Ser Asn Lys Trp Lys Asp Leu Asp Tyr Lys
            740                 745                 750

Ile Ser Leu Asn Gly Thr Asn Leu Leu Asn Gln Pro Val Tyr Ile His
        755                 760                 765

Thr Ser Tyr His Gln Phe Val Pro Gln Thr Gly Arg Asn Phe Ile Leu
    770                 775                 780

Val Val Asn Val Lys Phe
785                 790
```

<210> SEQ ID NO 28
<211> LENGTH: 809
<212> TYPE: PRT
<213> ORGANISM: Haemophilus parasuis

<400> SEQUENCE: 28

| Met | Ile | Asn | Asn | Arg | Thr | Thr | Glu | Gln | Gln | Asn | Asn | Arg | Thr | Thr | Ala |
| 1 | | | | 5 | | | | | 10 | | | | | 15 | |

| Phe | Ser | Leu | Ala | Phe | Ser | Leu | Leu | Cys | Cys | Leu | Gly | Ile | Asn | Ala |
| | | | 20 | | | | | 25 | | | | | 30 | |

| Glu | Gln | Leu | Glu | Leu | Asp | Glu | Ile | Ser | Val | Met | Gly | Lys | Val | Pro | Glu |
| | | 35 | | | | | 40 | | | | | 45 | | | |

| Gly | Asn | Ser | Ile | Ser | Phe | Leu | Lys | Val | Ser | Asp | Ala | Ile | Ile | Asp | Gly |
| | 50 | | | | | 55 | | | | | 60 | | | | |

| Glu | Lys | Phe | Lys | Asn | Arg | Ser | Ala | Thr | Leu | Gly | Asn | Ala | Leu | Ser | Ser |
| 65 | | | | | 70 | | | | | 75 | | | | | 80 |

| Glu | Leu | Gly | Val | His | Ser | Thr | Pro | Phe | Gly | Gly | Gly | Ala | Ser | Ala | Pro |
| | | | | 85 | | | | | 90 | | | | | 95 | |

| Ile | Ile | Arg | Gly | Gln | Glu | Gly | Val | Arg | Val | Lys | Ile | Leu | Gln | Asn | Asn |
| | | | 100 | | | | | 105 | | | | | 110 | | |

| Ala | Asp | Val | Val | Asp | Met | Ser | Asn | Ile | Ser | Pro | Asp | His | Ala | Ile | Thr |
| | | | 115 | | | | | 120 | | | | | 125 | | |

| Ala | Asp | Thr | Leu | Leu | Ala | Asn | Gln | Val | Glu | Ile | Leu | Arg | Gly | Ala | Ser |
| | 130 | | | | | 135 | | | | | 140 | | | | |

| Thr | Leu | Leu | Tyr | Ala | Ser | Ser | Pro | Ala | Gly | Ile | Val | Asn | Ile | Val |
| 145 | | | | | 150 | | | | | 155 | | | | | 160 |

| Asp | Gln | Arg | Ile | Pro | Asn | Lys | Met | Pro | Lys | Lys | Gly | Tyr | Glu | Val | Thr |
| | | | | 165 | | | | | 170 | | | | | 175 | |

| Leu | Ser | Ser | Arg | Phe | Asp | Thr | Ala | Ser | Lys | Glu | Lys | Val | Tyr | Ala | Leu |
| | | | 180 | | | | | 185 | | | | | 190 | | |

| Gly | Thr | Thr | Ile | Gly | Ile | Gly | Lys | His | Leu | Ala | Leu | Arg | Leu | Glu | Gly |
| | | | 195 | | | | | 200 | | | | | 205 | | |

| Leu | Asp | Arg | Gln | Ser | Gln | Asn | Tyr | Lys | Val | Pro | Gln | Ile | Lys | Leu | Gly |
| | 210 | | | | | 215 | | | | | 220 | | | | |

| Glu | Thr | Leu | Asn | Tyr | Val | Pro | Asp | Thr | Tyr | His | Gln | Ser | Lys | Val | Gly |
| 225 | | | | | 230 | | | | | 235 | | | | | 240 |

| Thr | Ile | Gly | Leu | Ser | Phe | Ile | Gly | Glu | Lys | Gly | Tyr | Leu | Gly | Ala | Ser |
| | | | | 245 | | | | | 250 | | | | | 255 | |

| Tyr | Asn | Gln | Arg | Lys | Asp | Arg | Tyr | Gly | Leu | Pro | Gly | His | Asn | His | Lys |
| | | | 260 | | | | | 265 | | | | | 270 | | |

| Phe | Asp | Thr | Cys | Ile | Ala | His | Ile | Tyr | Asp | Met | Arg | Leu | Gln | Gly | Lys |
| | | 275 | | | | | 280 | | | | | 285 | | | |

| His | Ser | Tyr | Thr | Asn | Leu | Tyr | Pro | His | Leu | Met | Ser | Asp | Glu | Met | Val |
| | 290 | | | | | 295 | | | | | 300 | | | | |

| Thr | Glu | Asn | Pro | His | Phe | His | Cys | Gly | Thr | Asp | Tyr | Asp | Leu | Asp | Pro |
| 305 | | | | | 310 | | | | | 315 | | | | | 320 |

| Ser | His | Ser | His | Asp | His | Pro | Tyr | Gly | His | Asp | His | Asp | His | Thr | His |
| | | | | 325 | | | | | 330 | | | | | 335 | |

| Ile | Gly | Pro | Trp | Val | Asp | Leu | His | Ser | Lys | Arg | Ile | Asp | Ile | Lys | Gly |
| | | | 340 | | | | | 345 | | | | | 350 | | |

| Glu | Ile | Lys | Gln | Pro | Leu | Pro | Met | Leu | Asp | Lys | Ile | Gln | Leu | Ser | Tyr |
| | | 355 | | | | | 360 | | | | | 365 | | | |

| Ala | Gln | Thr | Asp | Tyr | Tyr | His | Asp | Glu | Lys | Asp | Ala | Gly | Lys | Ser | Gly |

```
              370                 375                 380
Asp Thr Ile Asn Pro Asn Arg Val Asp Lys Ser Lys Asp Phe Gly Lys
385                 390                 395                 400

Pro Val Asn Ile Phe Lys Asn Gln Gly Lys Asn Ala Arg Leu Glu Phe
                405                 410                 415

Phe His Thr Pro Ile Gly Gly Leu Thr Gly Met Phe Gly Val Gln Tyr
                420                 425                 430

Gln Thr Leu Gln Ser Ser Ala Asn Thr Pro Asn Asn Arg Glu Val Gln
                435                 440                 445

Trp Pro Leu Val Asp Asn Arg Asn Lys Gln Ile Ser Leu Phe Ala Leu
        450                 455                 460

Glu Gln Tyr Ala Trp Asp Asn Phe Ala Ile Glu Leu Gly Leu Arg Thr
465                 470                 475                 480

Glu Lys Gln Asn Ile His Ile Asp Tyr Asp Leu Ala Lys Ile Gln Lys
                485                 490                 495

Gln Gln Lys Phe Asn Glu Arg Thr Tyr Gly Lys Gln Val Asp Pro Asp
                500                 505                 510

Leu Ser Asp Tyr Asp Glu Lys Ala Ile Ser Tyr Thr Gly Ala Phe Asn
        515                 520                 525

Trp Phe Phe His Pro Asp Tyr Gln Leu Ser Phe Thr Ala Ser His Asn
530                 535                 540

Glu Arg Leu Pro Thr Pro Met Glu Leu Tyr Tyr His Gly Gln His Leu
545                 550                 555                 560

Ala Thr Asn Ser Phe Glu Tyr Gly Asn Lys Asp Leu Lys Lys Glu Ile
                565                 570                 575

Ser Asn Asn Phe Glu Leu Gly Leu Gly Tyr His Thr Glu Lys Leu Asp
                580                 585                 590

Tyr Lys Leu Ser Thr Tyr Tyr Asn Asn Phe Asp Asn Tyr Ile Tyr Asn
        595                 600                 605

Glu Thr Leu Tyr Arg Ser Asn Asn Leu Phe Met Arg Arg Tyr Asn Gln
610                 615                 620

Ala Lys Ala Thr Phe Tyr Gly Leu Glu Gly Ile Ile Asn Tyr Arg Phe
625                 630                 635                 640

Thr Pro Asp Tyr Gln Phe Ser Val Phe Gly Asp Met Val Lys Gly Lys
                645                 650                 655

Leu Lys Gln Leu Pro Asp Ile Lys Gly Leu Asn Asp Val Tyr Gly Glu
                660                 665                 670

Pro Ile Leu Asn Pro Asp Tyr Asp Pro Glu Tyr Asp Glu Pro Glu Asp
        675                 680                 685

Gln Tyr Tyr Arg Pro Tyr Leu Gly Lys Glu Met Ile Lys Gln Ala Asp
690                 695                 700

Arg Val Ser Pro Arg Leu Pro Pro Ile Arg Leu Gly Ala Arg Phe Asn
705                 710                 715                 720

Ala Gln Leu Thr Glu Asn Leu Ser Gly Ser Val Glu Trp Met Lys Val
                725                 730                 735

Phe Thr Gln Asn Lys Val Ser Lys Leu Glu Ser Ser Thr Lys Gly Tyr
                740                 745                 750

Gln Leu Leu Asn Ala Ser Leu Asn Tyr Arg Arg Gln Ile Lys Gly Val
        755                 760                 765

Glu Tyr Thr Val Ser Leu Thr Gly Asn Asn Leu Leu Asn Gln Ala Val
770                 775                 780

Tyr Ile His Asn Ser Tyr His Pro Tyr Val Pro Gln Met Gly Arg Asn
785                 790                 795                 800
```

-continued

```
Phe Ile Leu Gly Leu Asp Leu Ser Phe
                805

<210> SEQ ID NO 29
<211> LENGTH: 713
<212> TYPE: PRT
<213> ORGANISM: Bordetella pertussis

<400> SEQUENCE: 29

Met Ile Cys Tyr Ile Val Ser Phe Asn Glu Asn Gly Thr Ser Phe Tyr
 1               5                  10                  15

Arg Glu Gly Asn Met Arg Phe Glu Arg His Pro Leu Ser Ala Ala Leu
                20                  25                  30

Ala Leu Ala Leu Ala Trp Gln Gly Ala His Ala Gln Ala Ser Ala Asp
            35                  40                  45

Gly Thr Ser Glu Ala Ala Thr Leu Ala Pro Ile Thr Val Ser Ala Ser
        50                  55                  60

Pro Leu Ala Gly Asp Leu Asp Ser Met Thr Ala Pro Ala Ala Val Leu
 65                  70                  75                  80

Glu Gly Asp Gln Leu Leu Leu Arg Arg Gln Gly Thr Leu Gly Asp Thr
                85                  90                  95

Leu Asp Gly Leu Pro Gly Val His Ala Asp Thr Phe Gly Gly Gly Ala
            100                 105                 110

Ser Arg Pro Val Ile Arg Gly Gln Thr Ala Pro Arg Val Lys Val Leu
        115                 120                 125

Ser Asp Gly Ser Glu Leu Met Asp Ala Ser Ala Ile Ser Pro Asp His
130                 135                 140

Ala Val Thr Thr Glu Pro Leu Leu Ala Asp Lys Ile Glu Val Leu Arg
145                 150                 155                 160

Gly Pro Ala Thr Leu Leu Tyr Gly Gly Ala Ile Gly Gly Val Val
                165                 170                 175

Asn Val Leu Asp Arg Lys Ile Pro Thr Ala Val Pro Gln Gln Gly Ile
            180                 185                 190

Glu Ala Glu Ala Glu Leu Arg Gly Ala Thr Gly Thr Lys Glu Arg Ala
        195                 200                 205

Gly Ala Ile Gly Ile Thr Ala Gly Ser Gly Asn Phe Ala Val Arg Val
    210                 215                 220

Glu Gly Leu Lys Arg Arg Ser Ser Asp Tyr Arg Val Pro Asp Trp Pro
225                 230                 235                 240

Asp Gly Lys Leu Ala Gly Ser Tyr Ser Glu Ser Gly Gln Gly Thr Val
                245                 250                 255

Gly Met Ser Trp Ile Thr Pro Arg Gly Tyr Val Gly Val Ala Phe Thr
            260                 265                 270

His Leu Glu Ser Lys Tyr Gly Leu Pro Gly His Asn His Glu Tyr Glu
        275                 280                 285

Gly Cys His Pro His Gly Ser His Leu His Cys Gly Gly His Asp Asp
    290                 295                 300

His Gly His Gly His Asp Glu His Glu Gly Glu Ala Glu His Asp
305                 310                 315                 320

His Gly His Glu His Gly Ala Gly Asp Val Pro Tyr Val Lys Leu Arg
                325                 330                 335

Ser Asn Arg Thr Asp Leu Arg Ala Glu Tyr Thr Asp Pro Phe Ala Gly
            340                 345                 350

Phe Glu Lys Ile Arg Phe Arg Gly Gly Leu Thr Asp Tyr Arg His Asp
```

```
                355                 360                 365
Glu Ile Glu Gly Gly Gln Leu Gly Thr Arg Phe Gln Asn Arg Gly Tyr
370                 375                 380

Asp Ala Arg Leu Glu Leu Thr His Arg Pro Leu Tyr Gly Trp His Gly
385                 390                 395                 400

Val Val Gly Val Gln Thr Ser Tyr Ser Asp Phe Arg Ala Thr Gly Glu
                405                 410                 415

Glu Ala Phe Leu Pro Arg Ser Lys Thr Arg Ala His Gly Leu Phe Leu
            420                 425                 430

Leu Glu Glu Tyr Arg Trp Ala Asp Trp Arg Phe Glu Leu Gly Ala Arg
        435                 440                 445

Gln Asp Trp Gln Arg Val Ser Pro Gln Ser Gly Ala Pro Ala Ser Arg
    450                 455                 460

Thr Ala Gly Thr Ser Leu Ser Ala Ala Ile Trp Asp Phe Ala Pro
465                 470                 475                 480

Gln Tyr Ser Leu Ala Leu Ser Val Ser Arg Ser Gln Arg Leu Pro Ser
                485                 490                 495

Ala Gln Glu Leu Tyr Ala Asp Gly Val His Leu Ala Thr Asn Thr Tyr
            500                 505                 510

Glu Ile Gly Asp Pro Gly Leu Asp Arg Glu Thr Ser Arg Asn Val Asp
        515                 520                 525

Leu Thr Leu Arg Lys His Ser Gly Asp Thr Thr Phe Ser Val Ser Ala
    530                 535                 540

Phe His Asn Arg Val Lys Asn Tyr Ile Tyr Ala Asn Thr Leu Asp Arg
545                 550                 555                 560

Tyr Glu Asp Phe Arg Leu Ile Glu Tyr Thr Gln Arg Asp Ala Glu Phe
                565                 570                 575

Thr Gly Val Glu Gly Glu Val Arg His Arg Phe Gly Lys Val Phe Ser
            580                 585                 590

Ala Ala Val Phe Gly Asp Tyr Val Arg Gly Arg Leu Thr Gly Gly Gly
        595                 600                 605

Gly Asn Leu Pro Arg Ile Pro Ala Ala Arg Leu Gly Val Arg Ala Asp
    610                 615                 620

Ala Gln Trp Gln Asn Trp Ala Gly Gly Val Glu Tyr Phe His Val Tyr
625                 630                 635                 640

Arg Gln Asp Asp Ile Ala Ala Tyr Glu Ser Ser Thr Pro Gly Tyr Asp
                645                 650                 655

Met Val Asn Ala Thr Ile Arg Tyr Arg Gly Lys Leu Asp Arg Thr Ala
            660                 665                 670

Tyr Glu Ile Tyr Leu Arg Gly Asn Asn Leu Leu Asn Lys Leu Ala Phe
        675                 680                 685

Asn His Ala Ser Phe Ile Ser Thr Val Ala Pro Leu Pro Gly Arg Ser
    690                 695                 700

Val Leu Leu Gly Val Arg Leu Thr Tyr
705                 710

<210> SEQ ID NO 30
<211> LENGTH: 818
<212> TYPE: PRT
<213> ORGANISM: Moraxella catarrhalis

<400> SEQUENCE: 30

Met Lys Val Thr Met Ile Lys Lys Pro Leu Ala Cys Ala Ile Leu Ala
1               5                   10                  15
```

```
Thr Phe Ser Met Pro Met Leu Ala Glu Ala Asn Leu Lys Asp Lys Pro
            20                  25                  30

Thr Val Ile Leu Asp Gly Val Ser Ile Thr Ser Leu Ala Asp Gln Asn
        35                  40                  45

Thr Glu Phe Gly Val Asn His Ser Lys Thr Val Ser Gly Ile Thr Val
    50                  55                  60

Ser Lys Glu Gln Leu Gln Gln Arg Ala Thr Thr Leu Gly Asp Ala Leu
65                  70                  75                  80

Ala Gly Glu Leu Gly Val His Ser Asn His Phe Gly Gly Gly Ala Ser
                85                  90                  95

Ala Pro Ile Ile Arg Gly Gln Glu Gly Lys Arg Leu Lys Ile Leu Gln
            100                 105                 110

Asn Gly Ser Glu Val Val Asp Met Ser Gly Leu Ser Pro Asp His Ala
        115                 120                 125

Ile Ala Val Asp Thr Thr Leu Ala Lys Gln Val Glu Ile Val Arg Gly
    130                 135                 140

Ser Gly Ala Leu Leu Tyr Ala Ser Gly Asn Ser Ala Gly Val Val Asn
145                 150                 155                 160

Val Val Asp Asp Lys Ile Pro Ser Lys Leu Pro Ser Lys Leu Gln Gly
                165                 170                 175

Asp Val Thr Val Arg Leu Ser Ser Ala Asn Arg Glu Lys Leu Ile Thr
            180                 185                 190

Ala Ser Ala Glu Ala Pro Leu Gly Glu His Val Ala Val Arg Val Ala
        195                 200                 205

Gly Leu Ser Lys Gln Ala Ala Asp Tyr Lys Thr Pro Arg Phe Asp Arg
210                 215                 220

His Val Phe Asn Lys Lys His Glu Asp Asp Asn Thr Gln Pro Glu Phe
225                 230                 235                 240

Ile Tyr Lys Asp Thr Leu Lys His Leu Pro Asp Ser His Ala Lys Ser
                245                 250                 255

Asn Ala Gly Thr Leu Gly Val Ser Trp Val Gly Asn Gln Gly Phe Leu
            260                 265                 270

Gly Ala Ser Val Ser Leu Arg Arg Asp Lys Tyr Gly Leu Pro Asn His
        275                 280                 285

Ser His Glu Tyr Glu Glu Cys Ser Val His Gly Ile Ser Gln Ser Ala
    290                 295                 300

Leu Gln Tyr Lys Pro Tyr Leu Arg Leu Tyr Pro Phe Leu Met Glu Asn
305                 310                 315                 320

Asp Asp Leu Glu Phe Asp Asn Ala Gly Leu Glu Cys His Thr His Asp
                325                 330                 335

Asp His Asp His Glu His Asp His Ala His Asp His Glu His Asp His
            340                 345                 350

Glu His Asp His Gly Lys Pro Trp Ile Asp Leu Lys Met Lys Arg Tyr
        355                 360                 365

Asp Val Gln Gly Gln Ile Asn Ala Pro Phe Ala Gly Ile Asp Lys Ile
    370                 375                 380

Arg Ala Ser Met Gly Lys Val Asp Tyr His His Asp Glu Ile Asp Gly
385                 390                 395                 400

Gly Glu Lys Thr Ser Phe Phe Asp Asn Gln Ala Asn Val Trp Arg Leu
                405                 410                 415

Glu Ala Ser His Thr Pro Ile His Thr Pro Met Gly Lys Phe Ser Gly
            420                 425                 430

Val Phe Gly Val Gly Tyr Leu Thr Ser Lys Asn Ser Gly Leu Val Pro
```

```
            435                 440                 445
Pro Arg Tyr Glu Asp Gly Asn Lys Gln Asp Thr Gln Asn Ile Leu His
450                 455                 460

Asn Asn Lys Thr Lys Thr Gly Ser Val Phe Trp Phe Glu Glu Tyr Lys
465                 470                 475                 480

Pro Asn Asp Lys Leu Thr Val Asp Ala Ala Arg Ile Glu Lys Gln
                485                 490                 495

Thr Ile Thr Met Asp Tyr Asp Lys Asp Ala Ile Tyr Gln Ser Leu Asn
                500                 505                 510

Leu Gly Leu Ala Thr Ala His Glu Pro Asp Ile Arg Phe Lys Arg Leu
                515                 520                 525

Leu Asp Ser Gly Thr Leu Asn Pro Lys Lys Gln Thr Ala Arg Ser Tyr
530                 535                 540

Ala Val Gly Thr His Leu Gln Leu Thr Pro Lys His Lys Leu Ser Leu
545                 550                 555                 560

Asn Leu Ser His Gln Glu Arg Leu Pro Asn Ala Gln Glu Leu Tyr Ala
                565                 570                 575

His Gly Met His Leu Ala Thr Asn Ser Phe Glu Ile Gly Asn Arg Phe
                580                 585                 590

Leu Asn Lys Glu Lys Ser Asn Asn Ile Asp Leu Gly Leu Thr Phe Gln
                595                 600                 605

Gly Asp Lys Trp Asp Tyr Arg Leu Gly Gly Tyr His Tyr Asp Phe Asp
610                 615                 620

Asn Tyr Val Phe Leu Gln Thr Leu Ser Gln Tyr Lys Gln Gly Leu Arg
625                 630                 635                 640

Gly Met Arg His Asp Lys Asp Leu Lys Thr Ala Arg Tyr Glu Gln Ala
                645                 650                 655

Ala Ala Lys Phe Tyr Gly Phe Asp Val Asn Ile Gly Tyr Gln Ile Asn
                660                 665                 670

Asp Val Tyr His Val Ala Leu Phe Gly Asp Tyr Ile Arg Gly Lys Leu
                675                 680                 685

Thr Asn Leu Pro Asp Lys Lys Gly Arg Thr Asp Ala Tyr Gly Asn Arg
690                 695                 700

Pro Leu Ile Lys Gln Pro Asp Ser His Thr Pro Arg Leu Pro Pro Lys
705                 710                 715                 720

Arg Leu Gly Met Lys Leu Thr Ala Asn Val Asn Ala Asn Trp Ser Gly
                725                 730                 735

Phe Leu Glu Tyr Arg His Thr Phe Lys Gln Asp Lys Leu Ala Asn Phe
                740                 745                 750

Glu Arg Pro Thr Pro Ala His Asn Leu Val Asn Leu Gly Leu Asn Tyr
                755                 760                 765

Gln His Lys Pro Ser His Gln Ala Gly Ser Val Gln Val Phe Phe Asn
                770                 775                 780

Ala Asn Asn Leu Leu Asn Asp Lys Val Phe Ala His Glu Thr Phe Phe
785                 790                 795                 800

Pro Asp Met Pro Gln Met Gly Arg Asn Phe Met Leu Gly Ala Asn Phe
                805                 810                 815

Lys Phe

<210> SEQ ID NO 31
<211> LENGTH: 766
<212> TYPE: PRT
<213> ORGANISM: Mannheimia haemolytica
```

<400> SEQUENCE: 31

```
Met Leu Lys Lys Asn Tyr Leu Thr Val Ser Ile Leu Ala Ile Ser
  1               5                  10                  15

Gly Val Gly Tyr Ala Asn Glu Ile Ser Leu Glu Thr Ile Thr Val Asp
             20                  25                  30

Gly Asn Thr Pro Ser Thr Lys Gly Lys Leu Leu Gly Gly Glu Leu Asn
             35                  40                  45

Ser Asn Glu Ser Val Val Asp Glu Lys Asn Leu Lys Gln Gly Ser Ile
 50                  55                  60

Thr Leu Gly Asn Ala Leu Ser Gly Glu Leu Gly Ile His Ser Ser Gln
 65                  70                  75                  80

Phe Gly Gly Gly Ala Ser Thr Pro Ile Ile Arg Gly Gln Glu Ser Lys
                 85                  90                  95

Arg Ala Lys Ile Leu Gln Asn Asn Gly Glu Asn Leu Asp Met Ser Gly
                100                 105                 110

Met Ser Pro Asp His Ala Val Thr Val Asp Ala Leu Leu Ala Lys Arg
            115                 120                 125

Ile Glu Ile Leu Arg Gly Pro Thr Thr Leu Leu Tyr Ser Ala Gly Asn
130                 135                 140

Thr Ala Gly Val Ile Asn Val Val Asp Asn Lys Ile Pro Thr Ala Ile
145                 150                 155                 160

Pro Glu Lys Gly Tyr Glu Gly Gln Phe Gly Val Arg Phe Gly Ser Ala
                165                 170                 175

Ser Lys Glu Arg Leu Thr Tyr Ala Gly Ser Thr Phe Ala Leu Gly Asn
            180                 185                 190

His Leu Ala Leu Arg Val Gln Gly Met Tyr Asn Lys Ala Ser Glu Tyr
        195                 200                 205

Tyr Ala Pro His Phe Thr Ile Glu Gly Lys Pro Tyr His Arg Val Pro
    210                 215                 220

Asp Ser Asp Val Gln Ser Gln Thr Gly Thr Val Ser Leu Ser Trp Ile
225                 230                 235                 240

Gly Glu Arg Gly His Leu Gly Ile Ala Tyr Thr Asp Arg Arg Asp Lys
                245                 250                 255

Tyr Gly Leu Ile Gly His Thr His Lys Tyr Asp His Tyr Thr Ile Ser
            260                 265                 270

Ile Ile Arg Gln Ala Val Met Phe Ala Lys Gly Tyr Leu Arg Phe Tyr
        275                 280                 285

Pro His Leu Ala Glu Glu Gly Asp Ile Asp Tyr Asn Asn Pro Gly Ile
    290                 295                 300

Arg Leu Leu His Thr His Ile Pro Gly Gly Ser His Tyr Gly Gln Asp
305                 310                 315                 320

Thr His Glu His Gly Lys Pro Trp Ile Asp Met His Ser Lys Arg Tyr
                325                 330                 335

Asp Ile Asp Gly Ser Leu Gln Asn Pro Leu Pro Gly Phe Glu Glu Ala
            340                 345                 350

Lys Ile Ser Ala Asn Tyr Val Asp Tyr Tyr His Asp Glu Lys Asp Gly
        355                 360                 365

Lys Arg Val Glu Asn Tyr Phe Lys Asn Lys Gly Lys Asn Leu Arg Phe
    370                 375                 380

Glu Leu Val His Lys Glu Trp Lys Gly Leu Lys Gly Ala Ile Gly Val
385                 390                 395                 400

Gln Tyr Thr Asn Gln Ser Thr Ser Ala Leu Ala Leu Glu Ala Ser Arg
                405                 410                 415
```

Ala Ala Lys Val Phe Asn Lys Gln Pro Leu Asn Asn Pro Lys Thr
            420                 425                 430

Lys Leu Trp Ser Leu Phe Ala Ile Glu Arg Leu Asn Leu Gly Asp Phe
        435                 440                 445

Thr Phe Glu Leu Ser Gly Arg Ala Glu Arg Gln Lys Ile Ala Met Asp
450                 455                 460

Tyr Asp Val Lys Leu Ile Asp Arg Trp Leu Gly Phe Asn Thr Pro Met
465                 470                 475                 480

Pro Asn Leu Asp Pro His Lys Asp Lys Gly Tyr Ser Tyr Ser Phe Ala
                485                 490                 495

Thr His Trp Tyr Phe Ala Pro Asn His Lys Leu Thr Leu Asn Ala Ala
            500                 505                 510

His Gln Glu Arg Leu Pro Asn Ala Gln Glu Leu Tyr Ala His Gly Lys
        515                 520                 525

His Ile Ala Leu Asn Ala Phe Glu Ala Gly Asn Lys Asn Leu Lys Lys
    530                 535                 540

Glu Arg Ser Asn Gln Ile Glu Leu Ser Leu Ala Tyr Val Gly Asp Lys
545                 550                 555                 560

Trp Asp Tyr Lys Leu Asn Leu Tyr His Thr Arg Tyr Gly Asn Tyr Ile
                565                 570                 575

Tyr Pro Leu Thr Leu Asn Asp Asn Arg Gly Pro Lys Ser Phe Thr Asp
            580                 585                 590

Glu Tyr Asn Leu Lys Val Asn Arg Tyr Tyr Gln Gly Glu Ala Arg Phe
        595                 600                 605

Ser Gly Ala Glu Gly Glu Ile Gly Tyr Leu Phe Thr Pro Asn Tyr Arg
    610                 615                 620

Leu Ala Val Phe Gly Asp Tyr Val Arg Gly Lys Leu Val Asn Leu Pro
625                 630                 635                 640

Asn Ile Ala Met Ser Tyr Asn Ile Trp Thr Gly Glu Val Asp Lys Trp
                645                 650                 655

Ala Ser Gln Pro Asp Ile Ser Ala Pro Arg Ile Pro Pro Leu Arg Leu
            660                 665                 670

Gly Ala Arg Phe Asn Ala Asp Phe Asn Leu Asn Trp Ser Gly Met Leu
        675                 680                 685

Glu Tyr Tyr Arg Val Phe Ala Gln Lys Lys Val Ser Lys Tyr Glu Gln
    690                 695                 700

Val Thr Pro Gly His His Gln Val Asn Leu Gly Val Thr Tyr Ser Asn
705                 710                 715                 720

His Phe Asn Gln Thr Glu Tyr Gln Val Phe Leu Lys Val Asp Asn Leu
                725                 730                 735

Leu Asn Gln Lys Met Tyr Gln His Ala Ser Tyr Leu Pro His Ile Pro
            740                 745                 750

Gln Met Gly Arg Asn Ala Met Leu Gly Met Asn Ile Ser Phe
        755                 760                 765

<210> SEQ ID NO 32
<211> LENGTH: 809
<212> TYPE: PRT
<213> ORGANISM: Pasteurella multocida

<400> SEQUENCE: 32

Met Pro Leu Leu Thr Leu Lys Ile Asn Met Phe Phe Met Arg Lys Ile
1               5                   10                  15

Ser Tyr Leu Ser Leu Cys Val Ile Ser Ala Leu Tyr Ser Gln Leu Ala

```
                   20                  25                  30
Val Ala Gln Ser Pro Leu Lys Asn Thr Ser Glu His Ile Glu Leu Glu
                35                  40                  45
Pro Ile Phe Val Asn Thr Leu Ile Glu Ser Arg Glu Gly Ala Pro Leu
             50                  55                  60
Gly Gly Arg Leu Met Ala Ser Glu Lys Ile Ile Pro Ala Tyr Ser Leu
 65                  70                  75                  80
Lys Gln Arg Gly Ser Asn Leu Gly Asp Ala Leu Ser Ser Glu Leu Gly
                 85                  90                  95
Ile His Ala Ser Gln Phe Gly Gly Ala Ser Ala Pro Val Ile Arg
                100                 105                 110
Gly Gln Glu Gly Lys Arg Ile Lys Val Leu Ser Ser Gly Asn Glu Thr
                115                 120                 125
Leu Asp Met Ser Ala Met Ser Pro Asp His Ala Val Ala Val Asp Ser
            130                 135                 140
Leu Leu Ala Lys Lys Val Glu Ile Leu Arg Gly Ala Asn Thr Leu Leu
145                 150                 155                 160
Tyr Ser Ser Gly Asn Ala Ala Gly Val Val Asn Val Val Asp Asn Lys
                165                 170                 175
Ile Pro Thr Ala Glu Val Val Gly Val Glu Gly Glu Val Gly Leu Arg
                180                 185                 190
Thr Gly Ser Ala Asp Asn Glu Arg Leu Val Asn Val Ala Leu Asp Val
            195                 200                 205
Gly Leu Ser Lys His Phe Ala Leu His Leu Glu Gly Leu His Lys Lys
        210                 215                 220
Ala Gly Asp Tyr Arg Thr Pro Ser Tyr Gln Tyr Gln Gly Ser Thr His
225                 230                 235                 240
His Lys Leu Ala Asn Ser Phe Val Asp Asn Arg Ser Gly Ser Val Gly
                245                 250                 255
Leu Ser Trp Val Gly Asp Lys Gly Tyr Leu Gly Val Ala Tyr Ser Gln
            260                 265                 270
Arg Lys Asp Lys Tyr Gly Leu Pro Ala His Ser His Leu Tyr Asp Glu
        275                 280                 285
Tyr Tyr Met His Val Leu Leu Ser Asp Ala His Trp Arg Lys Pro Tyr
        290                 295                 300
Leu Lys His Tyr Pro Phe Leu Met Glu Glu Thr Asp Ile Asp Tyr Asn
305                 310                 315                 320
Asn Pro Gly Ile Asp Cys Ile Lys Lys Glu Trp His Ser His Gly His
                325                 330                 335
Leu Cys Asn His Gly His Ala His His Gly Asn Gly Gln His Ser His
            340                 345                 350
Asp His His Ala His Ala Asp Pro His Ile Ala Leu Asn Thr Gln Arg
        355                 360                 365
Trp Asp Leu Arg Gly Glu Trp Lys Asn Pro Val Lys Gly Leu Asp Lys
        370                 375                 380
Val Arg Phe Ser Ile Ala Lys Val Gly Tyr Arg His Asp Glu Lys Ser
385                 390                 395                 400
Gly Ala Ile Ser Asp Asn Ser Phe Lys Asn Lys Gly Tyr Ser Ala Arg
                405                 410                 415
Val Glu Phe Leu His Gln Pro Ile Ala Gly Val Ser Gly Leu Ile Gly
            420                 425                 430
Leu Ser His Val Tyr Gln Asp Ser Tyr Ala Leu Asp Asn His Thr Leu
        435                 440                 445
```

Glu Tyr Arg Lys Gln Asn Leu Leu Ser Asp His Thr Thr Ala Gln Gln
    450                 455                 460

Ser Leu Phe Leu Met Glu His Val Glu Leu Gly Lys Trp Gln Phe Asp
465                 470                 475                 480

Ile Gly Gly Arg Val Glu Lys Gln Arg Ile Ala Met Lys Tyr His Phe
                485                 490                 495

Asn Val Pro Lys Asp Glu Gln Pro Glu Glu Leu Thr Arg Pro His
            500                 505                 510

Lys Ser Lys Ala Tyr Ser Tyr Ala Leu Ser Ala Asn Tyr Gln Leu Asn
    515                 520                 525

Glu Gln His Gln Phe Asn Met Ile Val Ser His Gln Glu Arg Leu Pro
            530                 535                 540

Asn Ala Gln Glu Leu Tyr Ala His Gly Lys His Leu Ala Thr Asn Ser
545                 550                 555                 560

Phe Glu Ala Gly Asn Lys Asn Leu Thr Lys Glu Arg Ser Asn Asn Val
                565                 570                 575

Glu Leu Gly Trp Gly Tyr Thr Gly Glu Lys Leu Gly Ile Lys Leu Ser
            580                 585                 590

Gly Tyr Tyr Gln Gln Phe Ser Asn Tyr Ile Tyr Ala Ala Ile Leu Asn
    595                 600                 605

Asn Lys Thr Ser Cys Pro Trp Arg Pro Asn Ser Arg Cys Leu Arg Ser
610                 615                 620

Leu Ser Asp Asp Tyr Pro Leu Arg Leu Tyr Arg Tyr Asn Gln Ala Lys
625                 630                 635                 640

Ala Lys Ile Tyr Gly Leu Glu Ala Glu Val Ser Tyr Gln Ile Ser Ser
                645                 650                 655

Thr His Ser Val Ser Ile Phe Gly Asp Tyr Val Arg Gly Lys Leu Lys
            660                 665                 670

Asp Leu Pro Ser Leu Pro Ile Gly Tyr Lys Tyr Ile Tyr Asn Glu Asn
    675                 680                 685

Tyr Asp Met Val Gly Val Gln Pro Thr Gly Trp Glu Lys Gln Pro Asp
690                 695                 700

Gly Asn Ala Pro Arg Met Ser Pro Met Arg Leu Gly Ile Lys Trp Asn
705                 710                 715                 720

Ala Tyr Phe Asp Asn Gly Ile Ser Phe Asn Thr Gln Leu Tyr Arg Val
                725                 730                 735

Phe Ala Gln Asn Lys Val Ala Arg Leu Glu Thr Pro Thr Lys Gly His
            740                 745                 750

Thr Met Leu Asn Leu Gly Met Ser Tyr Asp Gly Lys Met Gly Asn Asn
    755                 760                 765

Glu Tyr Thr Leu Phe Ala Asn Val Asn Asn Val Leu Asn Ser Arg Val
770                 775                 780

Tyr Asn His Thr Ser Phe Leu Ser Tyr Ile Pro Gln Ser Gly Leu Gly
785                 790                 795                 800

Leu Asn Val Gly Met Asn Phe Lys Phe
                805

<210> SEQ ID NO 33
<211> LENGTH: 758
<212> TYPE: PRT
<213> ORGANISM: Neisseria meningitidis

<400> SEQUENCE: 33

Met Ala Gln Thr Thr Leu Lys Pro Ile Val Leu Ser Ile Leu Leu Ile

```
                1               5               10              15
        Asn Thr Pro Leu Leu Ala Gln Ala His Glu Thr Glu Gln Ser Val Asp
                        20                  25                  30

Leu Glu Thr Val Ser Val Val Gly Lys Ser Arg Pro Arg Ala Thr Ser
                        35                  40                  45

Gly Leu Leu His Thr Ser Thr Ala Ser Asp Lys Ile Ile Ser Gly Asp
                        50                  55                  60

Thr Leu Arg Gln Lys Ala Val Asn Leu Gly Asp Ala Leu Asp Gly Val
         65                  70                  75                  80

Pro Gly Ile His Ala Ser Gln Tyr Gly Gly Ala Ser Ala Pro Val
                                85                  90                  95

Ile Arg Gly Gln Thr Gly Arg Arg Ile Lys Val Leu Asn His His Gly
                        100                 105                 110

Glu Thr Gly Asp Met Ala Asp Phe Ser Pro Asp His Ala Ile Met Val
                        115                 120                 125

Asp Thr Ala Leu Ser Gln Gln Val Glu Ile Leu Arg Gly Pro Val Thr
        130                 135                 140

Leu Leu Tyr Ser Ser Gly Asn Val Ala Gly Leu Val Asp Val Ala Asp
        145                 150                 155                 160

Gly Lys Ile Pro Glu Lys Met Pro Glu Asn Gly Val Ser Gly Glu Leu
                        165                 170                 175

Gly Leu Arg Leu Ser Ser Gly Asn Leu Glu Lys Leu Thr Ser Gly Gly
                        180                 185                 190

Ile Asn Ile Gly Leu Gly Lys Asn Phe Val Leu His Thr Glu Gly Leu
                        195                 200                 205

Tyr Arg Lys Ser Gly Asp Tyr Ala Val Pro Arg Tyr Arg Asn Leu Lys
        210                 215                 220

Arg Leu Pro Asp Ser His Ala Asp Ser Gln Thr Gly Ser Ile Gly Leu
        225                 230                 235                 240

Ser Trp Val Gly Glu Lys Gly Phe Ile Gly Val Ala Tyr Ser Asp Arg
                        245                 250                 255

Arg Asp Gln Tyr Gly Leu Pro Ala His Ser His Glu Tyr Asp Asp Cys
                        260                 265                 270

His Ala Asp Ile Ile Trp Gln Lys Ser Leu Ile Asn Lys Arg Tyr Leu
                        275                 280                 285

Gln Leu Tyr Pro His Leu Leu Thr Glu Glu Asp Ile Asp Tyr Asp Asn
                        290                 295                 300

Pro Gly Leu Ser Cys Gly Phe His Asp Asp Asn Ala His Ala His
        305                 310                 315                 320

Thr His Ser Gly Arg Pro Trp Ile Asp Leu Arg Asn Lys Arg Tyr Glu
                        325                 330                 335

Leu Arg Ala Glu Trp Lys Gln Pro Phe Pro Gly Phe Glu Ala Leu Arg
                        340                 345                 350

Val His Leu Asn Arg Asn Asp Tyr Arg His Asp Glu Lys Ala Gly Asp
                        355                 360                 365

Ala Val Glu Asn Phe Phe Asn Asn Gln Thr Gln Asn Ala Arg Ile Glu
                        370                 375                 380

Leu Arg His Gln Pro Ile Gly Arg Leu Lys Gly Ser Trp Gly Val Gln
        385                 390                 395                 400

Tyr Leu Gln Gln Lys Ser Ser Ala Leu Ser Ala Ile Ser Glu Ala Val
                        405                 410                 415

Lys Gln Pro Met Leu Leu Asp Asn Lys Val Gln His Tyr Ser Phe Phe
                        420                 425                 430
```

-continued

```
Gly Val Glu Gln Ala Asn Trp Asp Asn Phe Thr Leu Glu Gly Gly Val
        435                 440                 445

Arg Val Glu Lys Gln Lys Ala Ser Ile Gln Tyr Asp Lys Ala Leu Ile
    450                 455                 460

Asp Arg Glu Asn Tyr Tyr Asn His Pro Leu Pro Asp Leu Gly Ala His
465                 470                 475                 480

Arg Gln Thr Ala Arg Ser Phe Ala Leu Ser Gly Asn Trp Tyr Phe Thr
                485                 490                 495

Pro Gln His Lys Leu Ser Leu Thr Ala Ser His Gln Glu Arg Leu Pro
                500                 505                 510

Ser Thr Gln Glu Leu Tyr Ala His Gly Lys His Val Ala Thr Asn Thr
            515                 520                 525

Phe Glu Val Gly Asn Lys His Leu Asn Lys Glu Arg Ser Asn Asn Ile
    530                 535                 540

Glu Leu Ala Leu Gly Tyr Glu Gly Asp Arg Trp Gln Tyr Asn Leu Ala
545                 550                 555                 560

Leu Tyr Arg Asn Arg Phe Gly Asn Tyr Ile Tyr Ala Gln Thr Leu Asn
                565                 570                 575

Asp Gly Arg Gly Pro Lys Ser Ile Glu Asp Asp Ser Glu Met Lys Leu
                580                 585                 590

Val Arg Tyr Asn Gln Ser Gly Ala Asp Phe Tyr Gly Ala Glu Gly Glu
                595                 600                 605

Ile Tyr Phe Lys Pro Thr Pro Arg Tyr Arg Ile Gly Val Ser Gly Asp
            610                 615                 620

Tyr Val Arg Gly Arg Leu Lys Asn Leu Pro Ser Leu Pro Gly Arg Glu
625                 630                 635                 640

Asp Ala Tyr Gly Asn Arg Pro Phe Ile Ala Gln Asp Gln Asn Ala
                645                 650                 655

Pro Arg Val Pro Ala Ala Arg Leu Gly Phe His Leu Lys Ala Ser Leu
                660                 665                 670

Thr Asp Arg Ile Asp Ala Asn Leu Asp Tyr Tyr Arg Val Phe Ala Gln
            675                 680                 685

Asn Lys Leu Ala Arg Tyr Glu Thr Arg Thr Pro Gly His His Met Leu
    690                 695                 700

Asn Leu Gly Ala Asn Tyr Arg Arg Asn Thr Arg Tyr Gly Glu Trp Asn
705                 710                 715                 720

Trp Tyr Val Lys Ala Asp Asn Leu Leu Asn Gln Ser Val Tyr Ala His
                725                 730                 735

Ser Ser Phe Leu Ser Asp Thr Pro Gln Met Gly Arg Ser Phe Thr Gly
                740                 745                 750

Gly Val Asn Val Lys Phe
            755
```

US 9,259,461 B2

VACCINE COMPRISING PROTEIN NMB0964 FROM *NEISSERIA MENINGITIDIS*

This application is filed pursuant to 35 U.S.C. §371 as a United States National Phase Application of International Patent Application Serial No. PCT/EP2009/052689 filed Mar. 6, 2009, which claims priority to Application No. GB 0816447.7 filed Sep. 8, 2008, the contents of which are incorporated herein by reference.

FIELD OF THE INVENTION

This invention relates to immunogenic compositions for the prevention of diseases caused by *Neisseria* bacteria, in particular *Neisseria meningitidis*.

BACKGROUND OF THE INVENTION

Neisserial strains of bacteria are the causative agents for a number of human pathologies, against which there is a need for effective vaccines to be developed. In particular *Neisseria gonorrhoeae* and *Neisseria meningitidis* cause pathologies which could be treated by vaccination.

*Neisseria gonorrhoeae* is the etiologic agent of gonorrhea, one of the most frequently reported sexually transmitted diseases in the world with an estimated annual incidence of 62 million cases (Gerbase et al 1998 Lancet 351; (Suppl 3) 2-4). The clinical manifestations of gonorrhea include inflammation of the mucus membranes of the urogenital tract, throat or rectum and neonatal eye infections. Ascending gonococcal infections in women can lead to infertility, ectopic pregnancy, chronic pelvic inflammatory disease and tubo-ovarian abscess formation. Septicemia, arthritis, endocarditis and menigitis are associated with complicated gonorrhea.

The high number of gonococcal strains with resistance to antibiotics contributes to increased morbidity and complications associated with gonorrhea. An attractive alternative to treatment of gonorrhea with antibiotics would be its prevention using vaccination. No vaccine currently exists for *N. gonorrhoeae* infections.

*Neisseria meningitidis* is an important pathogen, particularly in children and young adults. Septicemia and meningitis are the most life-threatening forms of invasive meningococcal disease (IMD). This disease has become a worldwide health problem because of its high morbidity and mortality.

Thirteen *N. meningitidis* serogroups have been identified based on antigenic differences in the capsular polysaccharides, the most common being A, B and C which are responsible for 90% of disease worldwide. Serogroup B is the most common cause of meningococcal disease in Europe, USA and several countries in Latin America.

Vaccines based on the capsular polysaccharide of serogroups A, C, W and Y have been developed and have been shown to control outbreaks of meningococcal disease (Peltola et al 1985 Pediatrics 76; 91-96). However serogroup B is poorly immunogenic and induces only a transient antibody response of a predominantly IgM isotype (Ala'Aldeen D and Cartwright K 1996, J. Infect. 33; 153-157). There is therefore no broadly effective vaccine currently available against the serogroup B meningococcus which is responsible for the majority of disease in most temperate countries. This is particularly problematic since the incidence of serotype B disease is increasing in Europe, Australia and America, mostly in children under 5. The development of a vaccine against serogroup B meningococcus presents particular difficulties because the polysaccharide capsule is poorly immunogenic owing to its immunologic similarity to human neural cell adhesion molecule. Strategies for vaccine production have therefore concentrated on the surface exposed structures of the meningococcal outer membrane but have been hampered by the marked variation in these antigens among strains.

Further developments have led to the introduction of vaccines made up of outer membrane vesicles which will contain a number of proteins that make up the normal content of the bacterial membrane. One of these is the VA-MENGOC-BC Cuban vaccine against *N. meningitidis* serogroups B and C (Rodriguez et al 1999 Mem Inst. Oswaldo Cruz, Rio de Janeiro 94; 433-440). This vaccine was designed to combat an invasive meningococcal disease outbreak in Cuba which had not been eliminated by a vaccination programme using a capsular polysaccharide AC vaccine. The prevailing serogroups were B and C and the VA-MENGOC-BC vaccine was successful at controlling the outbreak with an estimated vaccine efficiency of 83% against serogroup B strains of *N. meningitidis* (Sierra et al 1990 In *Neisseria*, Walter Gruyter, Berlin, M. Achtman et al (eds) p 129-134, Sierra et al 1991, NIPH Ann 14; 195-210). This vaccine was effective against a specific outbreak, however the immune response elicited would not protect against other strains of *N. meningitidis*.

Subsequent efficacy studies conducted in Latin America during epidemics caused by homologous and heterologous serogroup B meningococcal strains have shown some efficacy in older children and adults but its effectiveness was significantly lower in younger children who are at greatest risk of infection (Milagres et al 1994, Infect. Immun. 62; 4419-4424). It is questionable how effective such a vaccine would be in countries with multistrain endemic disease such as the UK. Studies of immunogenicity against heterologous strains have demonstrated only limited cross-reactive serum bactericidal activity, especially in infants (Tappero et al 1999, JAMA 281; 1520-1527).

A second outer membrane vesicle vaccine was developed in Norway using a serotype B isolate typical of those prevalent in Scandinavia (Fredriksen et al 1991, NIPH Ann, 14; 67-80). This vaccine was tested in clinical trials and found to have a protective efficacy after 29 months of 57% (Bjune et al 1991, Lancet, 338; 1093-1096).

There are diverse problems with the anti-meningococcal vaccines currently available. The protein based outer membrane vaccines tend to be specific and effective against only a few strains. The polysaccharide vaccines are also suboptimal since they tend to elicit poor and short immune responses, particularly against serogroup B (Lepow et al 1986; Peltola 1998, Pediatrics 76; 91-96).

*Neisseria* infections represent a considerable health care problem for which no vaccines are available in the case of *N. gonorrhoeae* or vaccines with limitations on their efficacy and ability to protect against heterologous strains are available in the case of *N. meningitidis*. Clearly there is a need to develop superior vaccines against Neisserial infections that will improve on the efficacy of currently available vaccines and allow for protection against a wider range of strains.

SUMMARY OF THE INVENTION

The present inventors have found that the Neisserial antigen NMB0964 (NMB numbers refer to *Neisseria meningitidis* group B genome sequences available from www.neisseria.org) [known as NMA1161 in the *Neisseria meningitidis* group A genome of strain Z2491, and as BASB082 in WO 00/55327, and as ZnuD] is a conserved antigen throughout neisseria and can induce bactericidal antibodies against a range of neisserial strains. The inventors have found this antigen functions as a $Zn^{2+}$ receptor in the bacterium, and its expression is regulated by the level of $Zn^{2+}$ in the medium.

The present invention generally provides methods and compositions for eliciting an immune response against *Neisseria* spp. bacteria in a subject, particularly against a *Neisseria meningitidis* serogroup B strain.

In one aspect the present invention provides an immunogenic composition comprising: isolated outer membrane vesicles prepared from a *Neisseria* species bacterium, wherein the *Neisseria* species bacterium produces a level of a NMB0964 polypeptide sufficient to provide for production of a vesicle that, when administered to a subject, elicits anti-NMB0964 antibodies; and a pharmaceutically acceptable excipient.

This may be achieved due to the *Neisseria* species bacterium being genetically modified in NMB0964 polypeptide production by for instance: disrupting the functional expression of the Zur repressor (NMB1266)—a protein which switches off expression of NMB0964 in the presence of $Zn^{2+}$ in the medium; replacing the NMB0964 promoter with one that does not bind Zur, in particular with a stronger promoter than the endogenous NMB0964 promoter such as a lac promoter; or through using a medium low in $Zn^{2+}$ concentration—i.e. under 5, 4, 3, 2, 1, 0.9, 0.8, 0.7, 0.6, 0.5, 0.4, 0.3, 0.2, 0.1, 0.05 or 0.01 μM free $Zn^{2+}$—(such as Roswell Park Memorial Institute medium 1640 (RPMI) which has around 1.69 μM $Zn^{2+}$ by ICP-MS), or removing $Zn^{2+}$ in the medium, for instance using a known zinc chelator such as TPEN (N,N, N',N'-Tetrakis(2-pyridylmethyl)ethylenediamine)—enough should be added to the medium such that the expression of the NMB0964 is maximised.

The *Neisseria* species bacterium may be deficient in capsular polysaccharide, for instance through disruption of functional expression of the siaD gene. It may be disrupted in the functional expression of the msbB and/or htrB genes to detoxify the LOS in the outer membrane vesicle. It may be disrupted in the expression of one or more following genes: PorA, PorB, OpA, OpC, PilC, or FrpB. It may be disrupted in the functional expression of the lgtB gene. Such disruption methods are described in WO 01/09350 and WO2004/014417. The *Neisseria* species bacterium may be of immunotype L2 or L3.

Methods for the preparation or isolation of outer membrane vesicles (also known as microvesicles or blebs) from Neisserial strains are well known in the art, and are described in WO 01/09350 and WO2004/014417. Typically outer membrane vesicles are isolated by extracting either without a detergent, or with 0-0.5, 0.02-0.4, 0.04-0.3, 0.06-0.2, or 0.08-0.15% detergent, for instance deoxycholate, e.g. with around or exactly 0.1% deoxycholate.

BRIEF DESCRIPTION OF DRAWINGS

FIG. 3. Topology model of TdfI. The plug domain is colored dark grey, the beta strands light gray and the extracellular loops white. The histidine/aspartic acid stretches are boxed.

FIG. 8. Amino acid sequence alignment of TdfI of *N. meningitidis* strains MC58 with those of 053422, FAM18 and Z2491, the carrier strains α14, α153 and α275 The TonB box (Tb), the plug domain, the loops and the transmembrane domains (Tm) are marked above the sequence and the His- and Asp-rich stretches are underlined.

FIG. 9. Amino acid sequence alignment of the TdfI homologues. The histidine aspartic acid rich stretches are highlighted in grey.

DETAILED DESCRIPTION OF THE INVENTION

Figure 1:
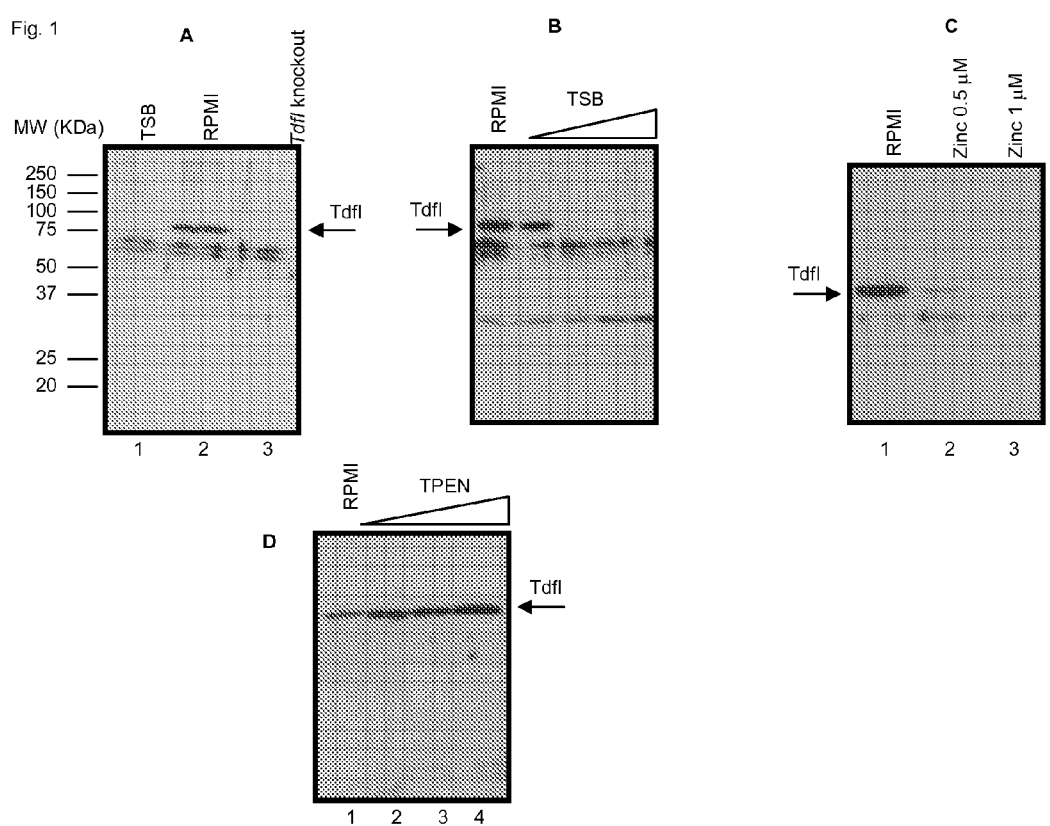
FIG. 1. Detection of TdfI on Western blot. (A) HB-1 grown in TSB (lane 1), RPMI (lane 2) and the tdfI knockout strain grown in RPMI (lane 3). (B) HB-1 grown in RPMI with increasing amounts of TSB added. (C) HB-1 grown in RPMI (lane 1), supplemented with 0.5 μM zinc (lane 2) or 1 μM zinc (lane 4). (D) HB-1 grown in RPMI (lane 1), with increasing concentrations of TPEN (0.1, 0.5 and 1 μM in lanes 2-4, respectively)

The present invention is based on the discovery that an OMV vaccine prepared either in specific culture conditions low in Zn2+, or from a mutant *N. meningitidis* strain engineered to either over-express NMB0964 or to remove the Zinc repression mechanism mediated through Zur, is enriched in NMB0964, and such OMVs may elicit good bactericidal antibody responses compared to OMVs which have not been prepared with these methods.

By the term NMB0964 polypeptide herein it includes the neisserial TdfI polypeptide (encoded by the tdfI gene) in general from any neisserial strain (the protein is so well conserved amongst neisserial strains its identity in any particular neisserial strain is readily ascertainable by persons skilled in the art). The term therefore includes the NMA1161 sequence, and the BASB082 polypeptide sequence (and all the Polypeptides of the Invention concerning the BASB082 polypeptide) of WO 00/55327. For instance the NMB0964 polypeptide of the invention will cover SEQ ID NO: 2 of WO00/55327 or polypeptides with more than 70, 80, 90 or 95% sequence identity with said SEQ ID NO:2, or polypeptides comprising immunogenic fragments of 7, 10, 12, 15 or 20 (or more) contiguous amino acids from said SEQ ID NO: 2 (in particular said immunogenic fragments being capable of eliciting—if necessary when coupled to a protein carrier—an immune response which can recognise said SEQ ID NO: 2). Particularly preferred NMB0964 immunogenic fragment embodiments are those extracellular loop sequences shown in the topology diagram of FIG. 3 as applied to any given NMB0964 sequence. In particular the third extracellular loop is provided (wherein the 2 Cys residues are optionally disulphide linked or not). Said NMB0964 immunogenic fragment polypeptide sequences may have more than 70, 80, 90 or 95% sequence identity with said extracellular loop sequences (as defined in FIG. 3) from SEQ ID NO:2 of WO 00/55327, or may be polypeptides comprising immunogenic fragments of 7, 10, 12, 15 or 20 (or more) contiguous amino acids from said extracellular loop sequences (as defined in FIG. 3) from SEQ ID NO: 2 (in particular said immunogenic fragments being capable of eliciting—if necessary when coupled to a protein carrier—an immune response which can recognise said SEQ ID NO: 2) and are provided as NMB0964 polypeptides of the invention. Said NMB0964 immunogenic fragment polypeptide sequences may have more than 70, 80, 90, 95, 99 or 100% sequence identity with the sequence from the third extracellular loop sequence given in FIG. 3 (wherein optionally the 2 Cys residues should be conserved, and may or may not be disulphide linked), or may be polypeptides comprising immunogenic fragments of 7, 10, 12, 15 or 20 (or more) contiguous amino acids from said extracellular loop sequence (in particular said immunogenic fragments being capable of eliciting—if necessary when coupled to a protein carrier—an immune response which can recognise SEQ ID NO: 2 of WO00/55327) and are provided as NMB0964 polypeptides of the invention. In one embodiment the NMB0964 immunogenic fragment polypeptides are not full-length NMB0964 (mature sequence or with signal sequence) polypeptides. Thus a further aspect of the invention is a immunogenic composition comprising such NMB0964 immunogenic fragment polypeptide sequences of the invention and a pharmaceutically acceptable excipient.

The term "a level of a NMB0964 polypeptide sufficient to provide for production of a vesicle that, when administered to a subject, elicits anti-NMB0964 antibodies" in one embodiment indicates that the level is sufficient to induce detectable bactericidal antibodies, for instance SBA titres of 100 or more, for instance it indicates that 5 g total protein content outer membrane vesicles of the invention when intramuscularly injected into mice at days 0, 21 and 28 produces serum on day 42 which generates an SBA titre of over 100 (for instance greater than 150, 200, 250, 300, 350, 400, 500, 700, 900 or 1000) using the SBA assay in the "Serum Bactericidal Assay" section of Example 2.

The heterologous promoter associated with the polypeptide of the invention being "stronger" than the non-repressed endogenous promoter of the polypeptide of the invention means that its use results in the expression of more polypeptide of the invention than when a non-repressed endogenous promoter of the polypeptide of the invention is utilised.

The term "protective immunity" means that a vaccine or immunization schedule that is administered to a mammal induces an immune response that prevents, retards the development of, or reduces the severity of a disease that is caused by *Neisseria meningitidis*, or diminishes or altogether eliminates the symptoms of the disease.

The phrase "a disease caused by a strain of serogroup B of *Neisseria meningitidis*" encompasses any clinical symptom or combination of clinical symptoms that are present in an infection with a member of serogroup B of *Neisseria meningitidis*. These symptoms include but are not limited to: colonization of the upper respiratory tract (e.g. mucosa of the nasopharynx and tonsils) by a pathogenic strain of serogroup B of *Neisseria meningitidis*, penetration of the bacteria into the mucosa and the submucosal vascular bed, septicemia, septic shock, inflammation, haemmorrhagic skin lesions, activation of fibrinolysis and of blood coagulation, organ dysfunction such as kidney, lung, and cardiac failure, adrenal hemorrhaging and muscular infarction, capillary leakage, edema, peripheral limb ischaernia, respiratory distress syndrome, pericarditis and meningitis.

"Serogroup" as used herein refers to classification of *Neisseria meningitides* by virtue of immunologically detectable variations in the capsular polysaccharide. About 12 serogroups are known: A, B, C, X, Y, Z, 29-E, W-135, H, I, K and L. Any one serogroup can encompass multiple serotypes and multiple serosubtypes.

"Enriched" means that an antigen in an antigen composition is manipulated by an experimentalist or a clinician so that it is present in at least a three-fold greater concentration by total weight, usually at least 5-fold greater concentration, more preferably at least 10-fold greater concentration, or at least 100-fold greater concentration than the concentration of that antigen in the strain from which the antigen composition was obtained. Thus, if the concentration of a particular antigen is 1 microgram per gram of total bacterial preparation (or of total bacterial protein), an enriched preparation would contain at least 3 micrograms per gram of total bacterial preparation (or of total bacterial protein).

The NMB0964 polypeptide of the invention may be enriched in the outer membrane vesicles of the invention through the methods discussed herein (for instance the culture conditions, or the overexpression of the polypeptide through recombinant means).

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Another example is where a Neisserial sequence is heterologous to a Neisserial host of a different strain. "Heterologous" as used herein in the context of proteins expressed in two different bacterial strains, indicates that the proteins in question differ in amino acid sequence.

The production strain can be a capsule deficient strain. Capsule deficient strains can provide vesicle-based vaccines that provide for a reduced risk of eliciting a significant autoantibody response in a subject to whom the vaccine is administered (e. g., due to production of antibodies that cross-react with sialic acid on host cell surfaces). "Capsule deficient" or "deficient in capsular polysaccharide" as used herein refers to a level of capsular polysaccharide on the bacterial surface that is lower than that of a naturally-occurring strain or, where the strain is genetically modified, is lower than that of a parental strain from which the capsule deficient strain is derived. A capsule deficient strain includes strains that are decreased in surface capsular polysaccharide production by at least 10%, 20%, 25%, 30%, 40%, 50%, 60%, 75%, 80%, 85%, 90% or more, and includes strains in which capsular polysaccharide is not detectable on the bacterial surface (e.g., by whole cell ELISA using an anti-capsular polysaccharide antibody).

Capsule deficient strains include those that are capsule deficient due to a naturally-occurring or recombinantly-generated genetic modification. Naturally-occurring capsule deficient strains (see, e.g., Dolan-Livengood et al. J. Infect. Dis. (2003) 187(10): 1616-28), as well as methods of identifying and/or generating capsule-deficient strains (see, e.g., Fisseha et al. (2005) Infect. Immun. 73(7):4070-4080; Stephens et al. (1991) Infect Immun 59(11):4097-102; Frosch et al. (1990) Mol Microbiol. 1990 4(7):1215-1218) are known in the art.

Modification of a Neisserial host cell to provide for decreased production of capsular polysaccharide may include modification of one or more genes involved in capsule synthesis, where the modification provides for, for example, decreased levels of capsular polysaccharide relative to a parent cell prior to modification. Such genetic modifications can include changes in nucleotide and/or amino acid sequences in one or more capsule biosynthesis genes rendering the strain capsule deficient (e.g., due to one or more insertions, deletions, substitutions, and the like in one or more capsule biosynthesis genes). Capsule deficient strains can lack or be non-functional for one or more capsule genes. Of particular interest are strains that are deficient in sialic acid biosynthesis.

Such strains can provide for production of vesicles that have reduced risk of eliciting anti-sialic acid antibodies that cross-react with human sialic acid antigens, and can further provide for improved manufacturing safety. Strains having a defect in sialic acid biosynthesis (due to either a naturally occurring modification or an engineered modification) can be defective in any of a number of different genes in the sialic acid biosynthetic pathway. Of particular interest are strains that are defective in a gene product encoded by the N-acetyl-glucosamine-6-phosphate 2-epimerase gene (known as synX AAF40537.1 or siaA AAA20475), with strains having this gene inactivated being of especial interest. For example, in one embodiment, a capsule deficient strain is generated by disrupting production of a functional synX gene product (see, e.g., Swartley et al. (1994) J Bacteriol. 176(5):1530-4).

Capsular deficient strains can also be generated from naturally-occurring strains using non-recombinant techniques, e.g., by use of bactericidal anti-capsular antibodies to select for strains that reduced in capsular polysaccharide.

In general as noted above, vesicles can be produced according to the invention using a naturally-occurring or modified non-naturally-occurring Neisserial strain that produces vesicles with sufficient NMB0964 protein that, when administered to a subject, provide for production of anti-NMB0964 antibodies.

In one embodiment, the Neisserial strain used to produce vesicles according to the invention can be naturally occurring strains that express a higher level of NMB0964 relative to strains that express no detectable or a low level of NMB0964.

In another embodiment, the Neisserial strain is modified by recombinant or non-recombinant techniques to provide for a sufficiently high level of NMB0964 production.

Such modified strains generally are produced so as to provide for an increase in NMB0964 production that is 1.5, 2, 2.5 3, 3.5, 4, 4.5, 5, 5.5, 6, 6.5, 7, 7.5, 8, 8.5, 9, 9.5, or 10-fold or greater over NMB0964 production in the unmodified parental cell or over NMB0964 production of the strain RM1O9O or H44/76. Any suitable strain can be used in this embodiment, including strains that produce low or undetectable levels of NMB0964 prior to modification and strains that naturally produce high levels of NMB0964 relative to strains that express no detectable or a low level of NMB0964.

Modified strains may be produced using recombinant techniques, usually by introduction of nucleic acid encoding a NMB0964 polypeptide or manipulation of an endogenous NMB0964 gene to provide for increased expression of endogenous NMB0964.

As noted above, this may be done by introduction of nucleic acid encoding a NMB0964 polypeptide or manipulation of an endogenous NMB0964 gene to provide for increased expression of endogenous NMB0964.

Endogenous NMB0964 expression can be increased by altering in situ the regulatory region controlling the expression of NMB0964. Methods for providing for increased expression of an endogenous Neisserial gene are known in the art (see, e. g., WO 02/09746).

Modification of a Neisserial host cell to provide for increased production of endogenous NMB0964 may include partial or total replacement of all of a portion of the endogenous gene controlling NMB0964 expression, where the modification provides for, for example, enhanced transcriptional activity relative to the unmodified parental strain.

Increased transcriptional activity may be conferred by variants (point mutations, deletions and/or insertions) of the endogenous control regions, by naturally occurring or modified heterologous promoters or by a combination of both. In general the genetic modification confers a transcriptional activity greater than that of the unmodified endogenous transcriptional activity (e.g., by introduction of a strong promoter), resulting in an enhanced expression of NMB0964.

Typical strong promoters that may be useful in increasing NMB0964 transcription production can include, for example, the promoters of porA, porB, lbpB, tbpB, p110, hpuAB, lgtF, Opa, p110, lst, and hpuAB. PorA, RmpM and PorB are of particular interest as constitutive, strong promoters. PorB promoter activity is contained in a fragment corresponding to nucleotides −1 to −250 upstream of the initation codon of porB.

Methods are available in the art to accomplish introduction of a promoter into a host cell genome so as to operably link the promoter to an endogenous NMB0964-encoding nucleic acid. For example, double cross-over homologous recombination technology to introduce a promoter in a region upstream of the coding sequence, e.g., about 1000 bp, from about 30-970 bp, about 200-600 bp, about 300-500 bp, or about 400 bp upstream (5') of the initiation ATG codon of the NMB0964-encoding nucleic acid sequence to provide for up-regulation. Optimal placement of the promoter can be determined through routine use of methods available in the art.

For example, a highly active promoter (e.g., PorA, PorB or RmpM promoters) upstream of the targeted gene. As an example, the PorA promoter can be optimized for expression as described by van der Ende et al. Infect Immun 2000; 68:6685-90. Insertion of the promoter can be accomplished by, for example, PCR amplification of the upstream segment of the targeted NMB0964 gene, cloning the upstream segment in a vector, and either inserting appropriate restriction sites during PCR amplification, or using naturally occurring restriction sites to insert the PorA promoter segment. For example, an about 700 bp upstream segment of the NMB0964 gene can be cloned. Using naturally occurring restriction enzyme sites located at an appropriate distance (e.g., about 400 bp) upstream of the NMB0964 promoter within this cloned segment a PorA promoter segment is inserted. An antibiotic (e.g., erythromycin) resistance cassette can be inserted within the segment further upstream of the PorA promoter and the construct may be used to replace the wild-type upstream NMB0964 segment by homologous recombination.

Another approach involves introducing a NMB0964 polypeptide-encoding sequence downstream of an endogenous promoter that exhibits strong transcriptional activity in the host cell genome. For example, the coding region of the RmpM gene can be replaced with a coding sequence for a NMB0964 polypeptide. This approach takes advantage of the highly active constitutive RmpM promoter to drive expression.

Neisserial strains can be genetically modified to over-express NMB0964 by introduction of a construct encoding a NMB0964 polypeptide into a Neisserial host cell. The NMB0964 introduced for expression is referred to herein as an "exogenous" NMB0964. The host cell produces an endogenous NMB0964, the exogenous NMB0964 may have the same or different amino acid sequence compared to the endogenous NMB0964.

The NMB0964 polypeptides useful in the invention also include fusion proteins, where the fusion protein comprises a NMB0964 polypeptide having a fusion partner at its N-terminus or C-terminus. Fusion partners of interest include, for example, glutathione S transferase (GST), maltose binding protein (MBP), His-tag, and the like, as well as leader peptides from other proteins.

Sequence identity can be determined using methods for alignment and comparison of nucleic acid or amino acid sequences, which methods are well known in the art. Comparison of longer sequences may require more sophisticated methods to achieve optimal alignment of two sequences. Optimal alignment of sequences for aligning a comparison window may be conducted by the local homology algorithm of Smith and Waterman (1981) Adv. Appl. Math. 2:482, by the homology alignment algorithm of Needleman and Wunsch (1970) J Mol. Biol. 48:443, by the search for similarity method of Pearson and Lipman (1988) Proc. Nati. Acad. Sci. (USA) 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e. resulting in the highest percentage of sequence similarity over the comparison window) generated by the various methods is selected.

Optimal alignment of sequences for comparison can be conducted, e. g., by the local homology algorithm of Smith & Waterman, Adv. Appi. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BBSTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschuel et al. (1977) Nucleic Acids Res. 25: 33 89-3402, respectively. Software for performing BLAST analyses is publicly available through the National Center for Biotechnology Information (www.ncbi.nlm.nih.govl). This algorithm involves first identifying high scoring sequence pairs (HSPs) by identifying short words of length.W in the query sequence, which either match or satisfy some positive-valued threshold score T when aligned with a word of the same length in a database sequence. T is referred to as the neighborhood word score threshold (Altschul et al, supra).

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences), uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Nati. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides share sequence identity is that the polypeptide encoded by the first nucleic acid is immunologically cross reactive with the polypeptide encoded by the second nucleic acid, as described below.

Thus, a polypeptide typically share sequence identity with a second polypeptide, for example, where the two polypeptides differ only by conservative substitutions. Another indication that two nucleic acid sequences share sequence identity is that the two molecules hybridize to each other under stringent conditions. The selection of a particular set of hybridization conditions is selected following standard methods in the art (see, for example, Sambrook, et al., Molecular Cloning: A Laboratory Manual, Second Edition, (1989) Cold Spring Harbor, N.Y.). An example of stringent hybridization conditions is hybridization at 50° C. or higher and 0.1×SSC (15 mM sodium chloride/i.5 mM sodium citrate). Another example of stringent hybridization conditions is overnight incubation at 42° C. in a solution: % formamide, 5×SSC (150 mM NaCl, 15 nIM trisodium citrate), 50 mM sodium phosphate (pH7.6), 5×Denhardt's solution, 10% dextran sulfate, and 20 mg/ml denatured, sheared salmon sperm DNA, followed by washing the filters in 0.1×SSC at about 65° C.

Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Methods and compositions which can be readily adapted to provide for genetic modification of a Neisserial host cell to express an exogenous NMB0964 polypeptide are known in the art. Exemplary vectors and methods are provided in WO 02/09746 and O'Dwyer et al. Infect Immun 2004; 72:651 1-80.

Figure 7:
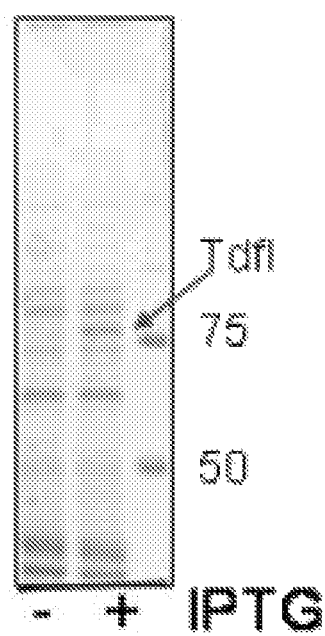
FIG. 7. Impact of IPTG on expression of TdfI on cells used in SBA. See Example 1.

Methods for transfer of genetic material into a Neisserial host include, for example, conjugation, transformation, electroporation, calcium phosphate methods and the like. The method for transfer should provide for stable expression of the introduced NMB0964-encoding nucleic acid. The NMB0964-encoding nucleic acid can be provided as a inheritable episomal element (e.g., plasmid) or can be genomically integrated.

Suitable vectors will vary in composition depending what type of recombination event is to be performed. Integrative vectors can be conditionally replicative or suicide plasmids, bacteriophages, transposons or linear DNA fragments obtained by restriction hydrolysis or PCR amplification. Selection of the recombination event can be accomplished by means of selectable genetic marker such as genes conferring resistance to antibiotics (for instance kanamycin, erythromycin, chloramphenicol, or gentamycin), genes conferring resistance to heavy metals and/or toxic compounds or genes complementing auxotrophic mutations (for instance pur, leu, met, aro).

In one embodiment, the vector is an expression vector based on episornal plasmids containing selectable drug resistance markers that autonomously replicate in both *E. coli* and *N. meningitidis*. One example of such a "shuttle vector" is the plasmid pFP1O (Pagotto et al. Gene 2000 244:13-19).

Immunization

In general, the methods of the invention provide for administration of one or more antigenic compositions of the invention to a mammalian subject (e.g., a human) so as to elicit a protective immune response against more than one strain of *Neisseria* species bacteria, and thus protection against disease caused by such bacteria. In particular, the methods of the invention can provide for an immunoprotective immune response against a 1, 2, 3, 4, or more strains of *Neisseria meningitidis* species, where the strains differ in at least one of serogroup, serotype, serosubtype, or NMB0964 polypeptide. Of particular interest is induction of a protective immune response against multiple strains of *Neisseria meningitidis* of serogroup B, particularly where the strains differ in serosubtype (e.g., have heterologous PorAs). Also of particular interest is induction of a protective immune response against strains that are heterologous to one other in terms of PorA and/or NMB0964.

The antigenic compositions of the invention can be administered orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remingtonts Pharmaceutical Science, 15th ed., Mack Publishing Company, Easton, Pa. (1980).

It is recognized that oral administration can require protection of the compositions from digestion. This is typically accomplished either by association of the composition with an agent that renders it resistant to acidic and enzymatic hydrolysis or by packaging the composition in an appropriately resistant carrier. Means of protecting from digestion are well known in the art.

The compositions are administered to an animal that is at risk from acquiring a Neisserial disease to prevent or at least partially arrest the development of disease and its complications. An amount adequate to accomplish this is defined as a "therapeutically effective dose." Amounts effective for therapeutic use will depend on, e. g., the antigenic composition, the manner of administration, the weight and general state of health of the patient, and the judgment of the prescribing physician. Single or multiple doses of the antigenic compositions may be administered depending on the dosage and frequency required and tolerated by the patient, and route of administration.

The antigenic compositions (herein also known as immunogenic compositions) described herein can comprise a mixture of vesicles which vesicles can be from the same or different strains. In another embodiment, the antigenic compositions can comprise a mixture of vesicles from 2, 3, 4, 5 or more strains.

The antigenic compositions are administered in an amount effective to elicit an immune response, particularly a humoral inmiune response, in the host. Amounts for the immunization of the mixture generally range from about 0.001 mg to about 1.0 mg per 70 kilogram patient, more commonly from about 0.001 mg to about 0.2 mg per 70 kilogram patient. Dosages from 0.001 up to about 10 mg per patient per day may be used, particularly when the antigen is administered to a secluded site and not into the blood stream, such as into a body cavity or into a lumen of an organ. Substantially higher dosages (e.g. 10 to 100 mg or more) are possible in oral, nasal, or topical administration. The initial administration of the mixture can be followed by booster immunization of the same of different mixture, with at least one booster, more usually two boosters, being preferred.

The antigen compositions are typically administered to a mammal that is immunologically naïve with respect to *Neisseria*, particularly with respect to *Neisseria meningitidis*. In a particular embodiment, the mammal is a human child about five years or younger, and preferably about two years old or younger, and the antigen compositions are administered at any one or more of the following times: two weeks, one month, 2, 3, 4, 5, 6, 7, 8, 9, 10, or 11 months, or one year or 15, 18, or 21 months after birth, or at 2, 3, 4, or 5 years of age.

In general, administration to any mammal is preferably initiated prior to the first sign of disease symptoms, or at the first sign of possible or actual exposure to *Neisseria*.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1

Immunogenicity of OMVs with Up-Regulation of TdfI

TdfI is a gene which is thought to be expressed when *N. meningitidis* is within the blood. It is therefore not normally expressed when strains are grown in conventional culture media, but wild-type strain H44/76, for example, can be made to express the protein in special culture conditions (RPMI culture media supplemented with hemin) The following experiment details the use of an H44/76 strain where TdfI expression has been recombinantly made inducible (through the use of IPTG). This allows the over-expression of TdfI on the surface of OMV vaccines made from the strain, and provides an easy way of culturing a strain expressing the antigen to establish whether antibodies generated against TdfI are capable of killing such a modified strain which expresses TdfI under normal culture conditions (+IPTG). The impact of IPTG on expression of TdfI on cells used in the SBA is shown in FIG. 7.

Groups of 10 mice were immunized three times with OMV by the intramuscular route on day 0, 21 and 28. Each inoculation was made up of 5 μg (protein content) of OMVs formulated on AlPO4 with MPL. The OMVs were derived from *Neisseria meningitidis* strain H44/76, engineered so that capsular polysaccharides and PorA were down regulated and LOS immunotype was galE type. A comparison was made of OMVs in which TdfI was or was not up-regulated (up-regulation under the control of IPTG inducible promoter). On day 42, blood samples were taken for analysis by serum bactericidal assay using either the homologous strain H44/76 (B:15:P1.7,16) expressing or not TdfI (after addition or not of IPTG in the culture media).

*N. meningitidis* strains were cultivated overnight on GC-agar with 10 μg/ml chloramphenicol Petri Dishes at 37° C.+5% $CO_2$. They were sub-cultured for 3 hours in a liquid TSB medium supplemented or not with IPTG 1000 μM. Individual sera were inactivated for 30 min at 56° C. Serum samples were diluted in HBSS-BSA 0.5% and then twofold diluted (8 dilutions) in a volume of 25 μl in flat bottom microplates. Bacteria were diluted in HBSS-BSA 0.5% to yield $8.10^3$ CFU/ml and 12.5 μl of this dilution was added to the serum dilution. Rabbit complement (12.5 μl) was also added to each well. After 75 min of incubation at 37° C. under shaking, 15 ul of the mixture was spread onto pre-warmed GC-agar plates incubated overnight at 37° C.+$CO_2$.

The CFU's were counted and the percentage of killing was calculated. The SBA titer is the dilution giving 50% of killing.

SBA titers: impact of expression of TdfI by target cells

| | SBA titers |
|---|---|
| H44/76 without IPTG | <50 |
| H44/76 with IPTG | 400; 400; 800 |

Without IPTG, TdfI is not expressed on target cells which are not killed by sera from mice immunized with up-regulated TdfI OMVs. When the expression of TdfI is specifically induced by IPTG the target cells express TdfI and are killed by anti-TdfI-OMVs mice sera.

Example 2

A Novel Zinc-Regulated Outer Membrane Protein in *Neisseria meningitidis* with Vaccine Potential Since the concentration of free iron in the human host is low, efficient iron-acquisition mechanisms constitute important virulence factors for pathogenic bacteria. In the Gram-negative bacteria, TonB-dependent outer membrane receptors are implicated in iron acquisition. However, transport across the bacterial outer membrane of other metals that are also scarce in the human host is far less clear. In this study we characterized a novel TonB-dependent receptor in *Neisseria meningitidis*. We show that the bacteria produce this protein under zinc limitation and that it is involved in zinc uptake. Furthermore, since the protein is highly conserved among isolates and is capable of inducing bactericidal antibodies, it constitutes a novel candidate for the development of a vaccine against *N. meningitidis* for which no effective universal vaccine is available so far. Homologues of the protein, designated TfdI, are found in many other pathogens residing in the respiratory tract, suggesting that receptor-mediated zinc uptake is particularly important for survival in this niche.

Introduction

The cell envelope of Gram-negative bacteria consists of two membranes, the inner and the outer membrane, which are separated by the periplasm containing the peptidoglycan layer. The outer membrane forms a barrier for harmful compounds from the environment. Most nutrients can pass the outer membrane by passive diffusion via abundant channel-forming outer membrane proteins, collectively called porins. However, diffusion is not an option when the extracellular concentration of a nutrient is low. This is the case, for example, for iron. Pathogens are confronted with low concentrations of free iron within the human host, where iron is bound by iron-transport and -storage proteins, such as lactoferrin and transferrin. Hence, efficient iron acquisition mechanisms constitute important virulence factors and have been studied extensively in many pathogens (1, 2).

When grown under iron-limiting conditions, Gram-negative bacteria induce the synthesis of outer membrane proteins that function as receptors for the iron-binding proteins of the host, for heme, or for siderophores, which are small iron-chelating compounds produced and secreted by the bacteria under iron limitation. The resolved crystal structures of such receptors revealed 22-stranded β-barrels, which do not form open channels but are closed by an N-terminal plug domain (3). After binding of the ligand to the receptor, the subsequent uptake is an active process that requires the energy of the proton gradient across the inner membrane, which is coupled to the receptors in the outer membrane via a complex of three proteins, the TonB complex (4, 5).

While iron-acquisition mechanisms have been studied extensively in many Gram-negative bacteria, little is known yet about the transport of other essential heavy metals, such as zinc and manganese, across the bacterial outer membrane. The concentration of these trace elements also is low in the human host, which, for example, responds to infections by the production of metallothioneins and calprotectin thereby reducing the availability of metals to the invading pathogens (6, 7). Therefore, Gram-negative pathogens likely possess effective acquisition mechanisms for these metals, which may or may not resemble the iron-acquisition systems.

*Neisseria meningitidis* is an obligate human pathogen that can colonize the nasopharyngeal mucosa asymptomatically. Occasionally the bacterium enters the bloodstream and can cause meningitis and sepsis with a high mortality rate (8). While vaccines are available for most pathogenic serogroups of *N. meningitidis* based on the capsular polysaccharides, a vaccine against serogroup B meningococci is lacking. The polysaccharide capsule of the serogroup B strains is poorly immunogenic due to its resemblance to human glycoproteins (9). Thus, subcapsular antigens are being studied as alternative vaccine components; however, these studies are frustrated by the high antigenic variability of the major outer membrane proteins. Therefore, attention has shifted to minor antigens, including the TonB-dependent receptors.

When grown under iron limitation, *N. meningitidis* produces TonB-dependent receptors for lactoferrin (10), transferrin (11), hemoglobin (12, 13) and enterobactin (14), all involved in the uptake of iron. Based on homology searches, Turner et al (15) identified seven additional genes for putative TonB-dependent family (Tdf) members in the available genome sequences of three Neisserial strains. Interestingly, the expression of some of these tdf genes appeared unaffected by iron availability in various microarray studies (16, 17), indicating that their products might be implicated in the transport of metals other than iron. Here we studied the regulation of the synthesis, the function and the vaccine potential of one of these receptors and show that this receptor is involved in the uptake of zinc.

Results

TdfI is not a Heme Receptor

TdfI (locus tags NMA1161 and NMB0964 in the sequenced genomes of *N. meningitidis* serogroup A strain Z2491 and serogroup B strain MC58, respectively) was previously identified as one of seven novel putative TonB-dependent receptors present in the Neisserial genomes (15) and was found to be up-regulated in the presence of naïve human serum (18). Since almost all TonB-dependent receptors studied to date are involved in iron acquisition we assumed that TdfI transports an iron complex. This idea was strengthened by the fact that blast searches (19) with the amino-acid sequence of NMA1161 revealed high sequence similarity to outer membrane receptors for the uptake of heme, such as HumA of *Moraxella catarrhalis* (20) with 41% identity and 58% similarity.

To assess the function of TdfI, we constructed a tdfI deletion mutant of a non-encapsulated derivative of serogroup B strain H44/76 called HB-1. We found similar binding of heme to HB-1 and the tdfI mutant as assessed by dot blot analysis and the tdfI mutant strain could still grow on plates with heme as the sole iron source. We could also not find increased heme binding by *Escherichia coli* cells expressing TdfI. Also we were unable to complement an *E. coli* heme auxotroph (data not shown). Therefore, we hypothesized that TdfI, although homologous to heme receptors, does not function as a heme receptor.

Regulation of tdfI by Zinc

Since TdfI is not a heme receptor and is not found to be regulated by iron, we sought conditions where we could detect tdfI is expression in the capsule deficient H44/76 *Neisseia meningitidis* HB-1. We could never detect TdfI on Western blots when the bacteria were grown in tryptic soy broth (TSB), a complex rich medium (FIG. 1 A, lane 1). However, when the bacteria were grown in the chemically defined RPMI medium, TdfI was detectable in bacterial lysates (FIG. 1 A, lane 2). The specificity of the signal detected was demonstrated by its absence in the tdfI knockout strain grown in RPMI (FIG. 1 A, lane 3). We noted that the presence of even small amounts of TSB added to RPMI negatively affected TdfI synthesis (FIG. 1 B); apparently TSB contains a compound that represses the transcription of tdfI. Since we noticed that RPMI does not contain a source of trace metals, we decided to test whether addition of a cocktail of trace metals, containing cobalt, molybdenum, manganese, copper and zinc, would repress tdfI expression, which indeed appeared to be the case. We then tested all these metals separately and found that specifically zinc, even at sub-µM concentrations, caused repression of tdfI expression (FIG. 1 C). Since standard RPMI is not supplemented with a specific zinc source, the available zinc required for bacterial growth presumably comes from the water and/or traces in the salts used to make the medium. We measured the zinc concentration in RPMI medium by inductively coupled plasma mass spectrometry (ICP-MS) and found it to be ~110 parts per billion (~1.69 µM). The zinc regulation of tdfI became even more evident when we supplemented the RPMI medium with the specific zinc chelator N,N,N',N'-Tetrakis-(2-pyridylmethyl)-Ethylenediamine (TPEN). Addition of TPEN to the medium resulted in a dose-dependent increase in TdfI synthesis (FIG. 1 D). However, concentrations above 1 µM TPEN totally inhibited cell growth presumably due to total zinc depletion from the medium. Growth could be restored by the addition of zinc (data not shown). The zinc regulation of tdfI was confirmed by real-time quantitative PCR (RT-qPCR) using total RNA obtained from cultures grown in RPMI supplemented or not with 500 nM zinc or 0.5 µM TPEN. The data showed a 13.8-fold repression in the presence of zinc and a 3.8-fold up regulation in the presence of TPEN. The fold difference between added TPEN and zinc was 52.6-fold.

Role of the Transcriptional Regulator Zur in tdfI Expression

In *E. coli*, the zinc uptake regulator (Zur) has been shown to regulate the expression of the znuACB genes, which encode the periplasmic binding protein, the ATPase and the integral inner membrane component required for zinc transport from the periplasm to the cytoplasm (23). In the presence of zinc, Zur binds a Zur-binding element (consensus GAAATGTTATANTATAACATTTC) (SEQ NO:1) in the promoter of the znuACB operon and thereby blocks transcription.

Figure 2:
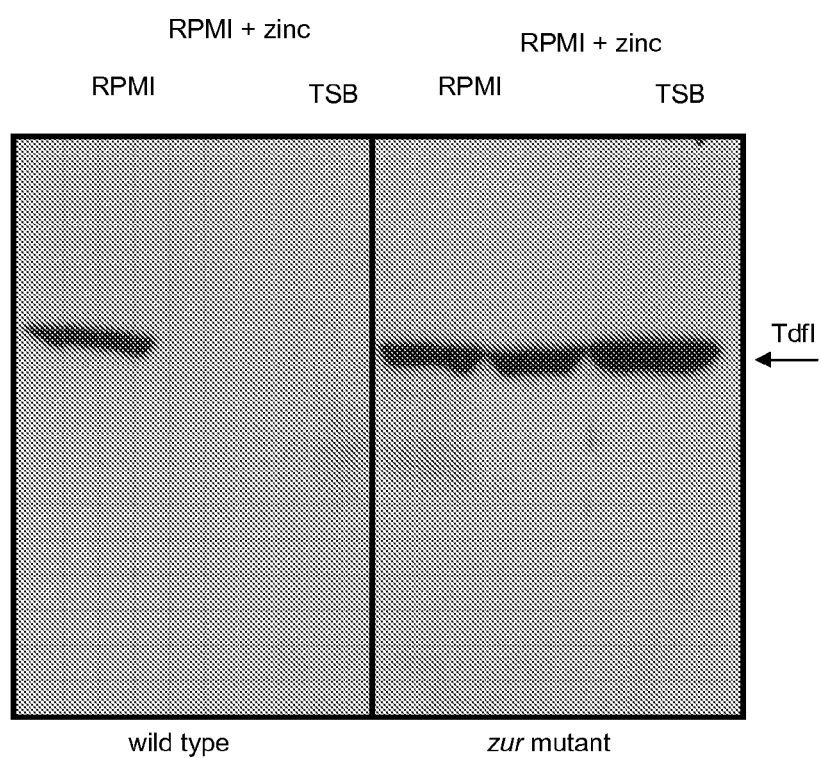
FIG. 2. TdfI expression in wild type and zur mutant strains. The presence of TdfI in cell lysates of HB-1 and the zur mutant grown in RPMI, RPMI with 600 nM zinc or TSB was assessed by Western blot analysis.

In the genome sequence of *N. meningitidis* strain MC58, we identified homologues of the *E. coli* zur gene, i.e. NMB1266, and of znuCBA, i.e.NMB0588, NMB0587, and NMB0586. In addition, we found sequences resembling the *E. coli* Zur binding consensus in the regions upstream of the neisserial tdfI (GtAATGTTATATaATAACAaact) (SEQ NO:2) and znuC (cAAAcGTTATACagTAtCATaTC) (SEQ NO:3) (identical nucleotides to the *E. coli* consensus are in capital case). To confirm the involvement of Zur in the regulation of tdfI expression, we generated a zur mutant of strain HB-1, which, indeed, produced TdfI constitutively (FIG. 2). Also, RT-qPCR demonstrated the involvement of Zur in the expression of znuA and tdfI as znuA and tdfI expression levels increased 5- and 34-fold, respectively, in the zur mutant compared to its parent strain both grown in the presence of zinc.

TdfI Facilitates Zinc Acquisition

Figure 4:
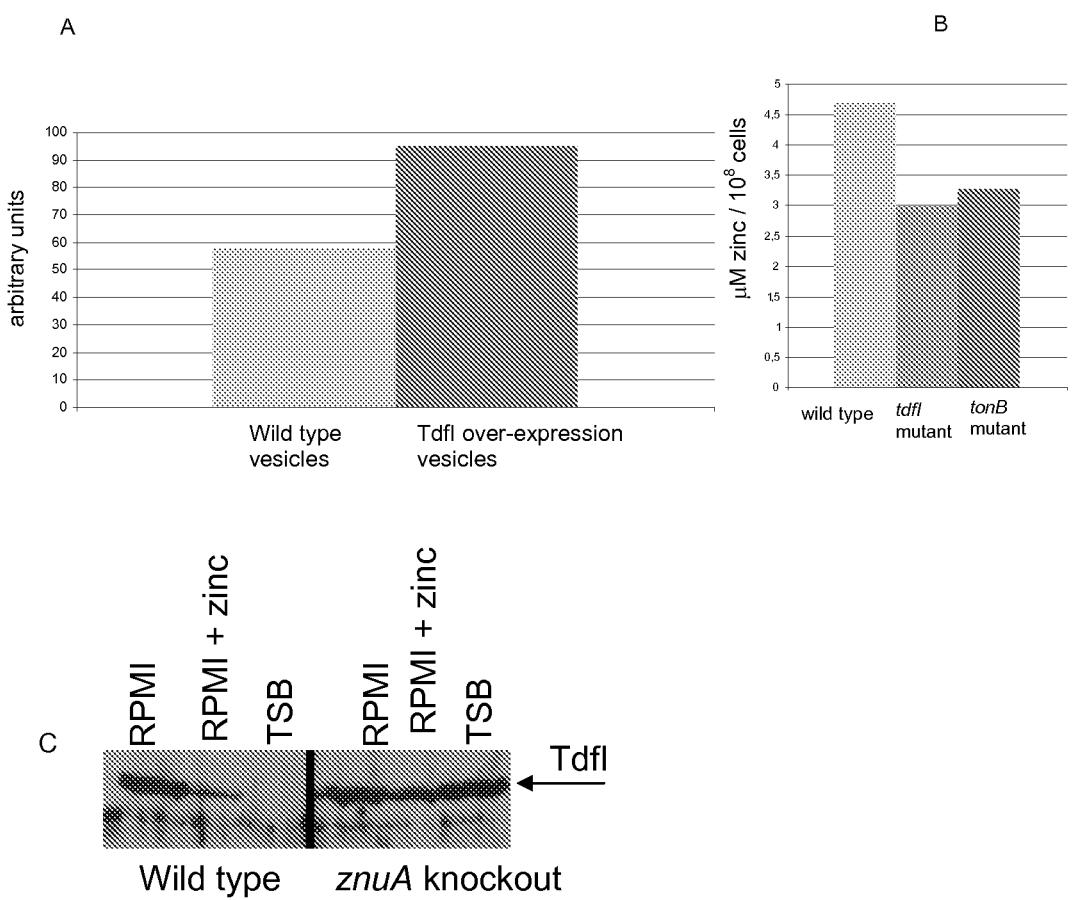
FIG. 4. Zinc binding and transport by TdfI. (A) Zinc binding to outer membrane vesicles either containing or not TdfI was measured by a PAR competition assay (B) Intracellular zinc concentrations as measured by ICP-MS of the wild-type strain, the tdfI mutant and the tonB mutant.

Since the expression of tdfI is regulated by the availability of zinc, it is likely that TdfI acts as a receptor for zinc or a zinc-containing complex. We first analyzed the amino acid sequence and constructed a topology model of TdfI using the PROFtmb program at www.rostlab.org, (FIG. 3). TdfI contains two cysteine residues in the putative extracellular loop L3. If these cysteines form a disulfide bond (supported by our analysis of the membrane fraction of bacteria by SDS-PAGE with and without DTT where incubation of the sample with the reducing agent resulted in a shift in electrophoretic mobility, presumably due to the disruption of the disulfide bond), they bring two stretches of amino acid residues, both rich in histidine and aspartic acid residues, in close proximity (FIG. 3), which could be of functional importance, since also in the periplasmic ZnuA protein of *E. coli*, a stretch of His and Asp residues is involved in binding zinc (25). Thus, we considered the possibility that TdfI binds free zinc and transports it to the periplasm. To test this hypothesis we first determined whether TdfI could bind zinc. We compared outer membrane vesicles with and without TdfI for their ability to compete with 4-(2-pyridylazo)resorcinol (PAR) for zinc. The outer membrane vesicles containing TdfI showed ~40% increased binding of zinc compared to the vesicles without TdfI (FIG. 4A). To test transport of zinc we compared the tdfI knockout, a tonB knockout and their parent strain for the accumulation of intracellular zinc using ICP-MS. HB-1 accumulated ~33% more zinc than the tdfI mutant or the tonB mutant, indicating that TdfI transports free zinc and that this transport needs the TonB system (FIG. 4B).

If indeed TdfI is involved in the uptake of free zinc, than one would expect derepression of znu gene expression to occur at higher external zinc concentrations in the tdfI mutant as compared with the wild-type strain. To test this idea, we grew the tdfI mutant and the parent strain in RPMI medium with 500 nM additional zinc, which largely, but not completely represses tdfI expression in the wild-type strain (FIG. 1C). We subsequently measured the relative levels of tdfI and znuA mRNA by RT-qPCR. The tdfI mutant still contains the first 437 nucleotides of the tdfI gene that were used for the detection of gene expression. In the tdfI mutant, there was 18.6-fold more tdfI and 7.4-fold more znuA expressed, showing that indeed the intracellular zinc concentration in the tdfI mutant is lower than that in the parent strain under the applied growth conditions. Also a znuA knockout strain expressed high levels of TdfI in the presence of zinc, confirming that ZnuA is required to sustain sufficient zinc levels in the cell (FIG. 4C). Thus, both TdfI and ZnuA are involved in the transport of zinc.

Conservation of TdfI

Figure 5:
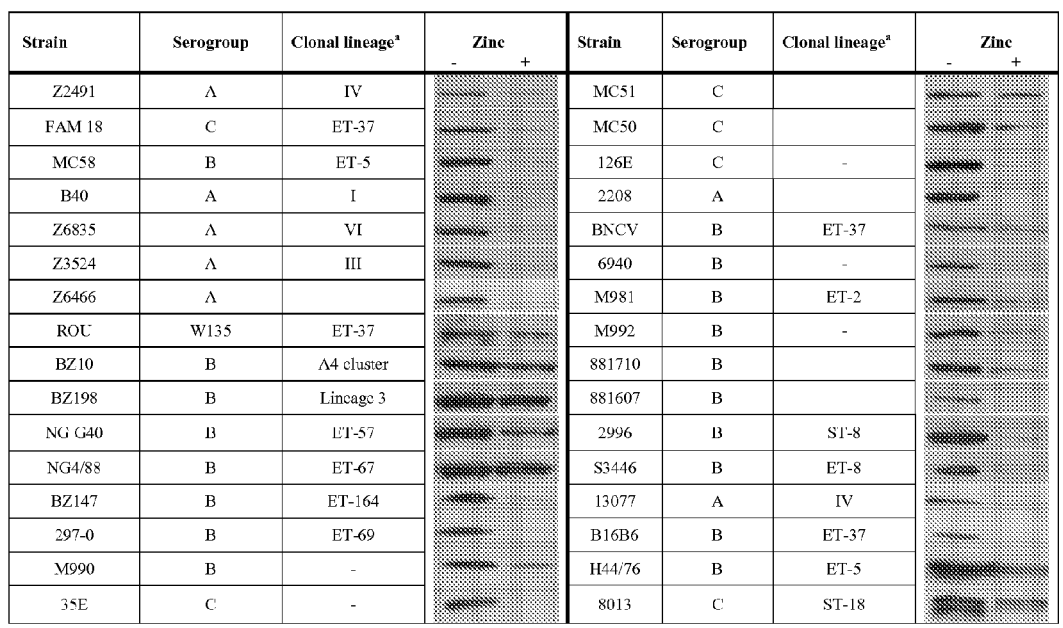
FIG. 5. Zinc regulation of TdfI is highly conserved in meningococci. Western blot of cell lysates of the indicated strains grown in RPMI with or without added zinc. [a] Clonal group designations taken from (36);—indicates that the strain was typed by Multi-Locus Enzyme Electrophoresis but could not be assigned to a specific clone.

Besides the function f TdfI we also want to investigate whether TdfI is a vaccine candidate for a universal *N. meningitidis* vaccine. One of the criteria is that the antigen has to be conserved. We first looked at the available *N. meningitidis* genomes and found that TdfI has a striking 97-99% amino acid identity of the mature protein (FIG. 8). The sequence differences are scattered throughout the protein and are not clustered in predicted extracellular loop regions, which are often antigenically variable in *Neisseria* outer membrane proteins (FIG. 8). We subsequently analyzed the presence of TdfI in a panel of 32 different *N. meningitidis* isolates from different serogroups and different clonal lineages. Each strain was grown in RPMI medium supplemented or not with 500 nM zinc and analyzed by Western blotting with the antiserum raised against TdfI of H44/76. All strains showed a repression of TdfI in the presence of zinc (FIG. 5).

We then wanted to know the homology of TdfI to other pathogenic bacteria. We first compared TdfI with *N. gonorrhea* and found a 96% identity and a 97% similarity between these two *Neisseria* strains. Next, we used the blast program at NCBI with a cutoff of 40% identity at the amino acid level to search for homologs of TdfI in other pathogenic bacteria. We identified homologs in other pathogenic bacteria, including *M. catarrhalis, Haemophilus parasuis, Mannheimia haemolytica, Acinetobacter baumannii, Pasteurella multocida, Bordetella pertussis* and *Actinobacillus pleuropneumoniae*, averaging a 41% identity and 59% similarity at the amino acid level and all TdfI homologs have the His/Asp region (FIG. 9). Interestingly, in *B. pertussis* the tdfI homologue is located adjacent to homologues of the znuABC and zur genes, again indicating a functional relationship between these genes. Furthermore, all these TdfI homologs contain His- and Asp-rich stretches (FIG. 9).

TdfI Induces Bactericidal Antibodies

Figure 6:
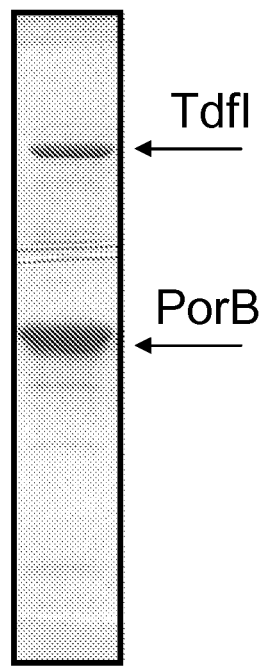
FIG. 6. Protein profile of the TdfI vaccine. Outer membrane vesicles used to immunize mice for antiserum production were separated by SDS-PAGE and stained with Coomassie brilliant blue.

To investigate the vaccine potential of TdfI, we immunized mice with Neisserial outer membrane vesicles containing overexpression levels of this protein (FIG. 6A) and tested the resultant sera for the presence of bactericidal antibodies. Routinely, we perform serum bactericidal assays on bacteria grown in TSB medium; however, under these conditions tdfI is not expressed. Therefore, we tested the sera for bactericidal activity on a strain that expressed TdfI from an isopropyl β-D-1-thiogalactopyranoside (IPTG)-inducible promoter and compared cultures grown with and without IPTG. The bactericidal titers of the sera were <1:100 when IPTG was absent, but 1:1042 when IPTG was present during growth of the bacteria. Titers in pre-immune sera were also <1:100. These data clearly show that TdfI is able to elicit bactericidal antibodies. We also wanted to investigate whether normal chromosome-encoded tdfI expression levels are sufficient to mediate complement-mediated killing. For this we employed the zur knockout strain that produces TdfI constitutively in the TSB medium and grows comparable to the wild-type strain in this medium.

Discussion

The high-affinity ZnuABC uptake system for zinc has previously been identified in *N. gonorrhoeae* (30). Homologues can be found in the meningococcal genome, as described above, and in the genomes of many other bacteria. In *Salmonella enterica* this ABC transporter has been associated with virulence (31). In no case, an outer membrane receptor involved in zinc acquisition has been identified and it is thought that zinc diffuses through the porins.

In the human host, however, the free zinc levels are most likely too low to sustain bacterial growth by passive diffusion. The total amount of zinc in human serum is approximately 19 μM, but the vast majority is bound by serum proteins such as albumin (32). Here we have identified an outer membrane receptor, TdfI that is regulated by zinc. The addition of 700 nM zinc to the growth medium completely repressed TdfI expression. The function of TdfI is to bind and transport of unbound (free) zinc. We predict that the zinc is bound initially by the His/Asp stretch in the external loop and then internalized via two histidines that are on top of the plug domain (FIG. 3b). A possible role for the TonB system in zinc uptake is that it pulls the plug out of the barrel and with this movement the zinc bound to the two His residues is transported into the periplasm where it is picked up by the periplasmic binding protein ZnuA.

Interestingly, similar regulation of tdfI and znuA expression was reported in a microarray study using *N. gonorrhoeae* (33). The tdfI homolog NGO1205 and the znuA homolog NGO0168 were upregulated in a mutant lacking the NGO0542 gene. This gene was annotated in that study as perR because of its homology to a manganese-dependent peroxide-responsive regulator found in gram-positive organisms (34). However, this is the same gene we have annotated as zur. The zur annotation is clearly more accurate, because we show an identical regulation by the absence of zur or the absence of zinc. More evidence for the annotation zur rather than perR comes from the same study in *N. gonorrhoeae*. Microarrays performed with the gonococcal perR mutant showed upregulation also of the ribosomal proteins L31 and L36. The Neisserial genomes contain two copies for each of the genes encoding these proteins with one form of each protein containing a zinc ribbon motif. Zinc availability was found to be the key factor controlling the type of L31/L36 protein expressed in *B subtilis* (34). In the gonococcal perR mutant, expression specifically of L31 and L36 paralogs lacking the zinc ribbons is induced, highly indicative of a disturbed zinc regulation in a perR mutant. Moreover in another study (17) a microarray was performed to identify the response to oxidative stress and neither perR nor any of the genes identified in the PerR study (33) were de-repressed and we do not see any regulatory effect of manganese on the expression of tdfI and znuA.

Previously, tdfI expression was reported to be induced in the presence of active complement (18). In this microarray study expression profiles were compared of *N. meningitidis* grown in the presence of serum and heat-inactivated serum, and TdfI was found 23-fold de-repressed in the presence of the untreated serum. The relationship between zinc and complement regulation may not be obvious at first sight. A possible explanation for finding similar regulatory circuits may be that the bacteria in the array study were pre-grown in RMPI with BSA. Albumin is known to chelate zinc, and therefore, pre-growth conditions may have been severely zinc-limited. Heat-treatment of human serum will release zinc from albumin, thereby repressing tdfI expression. This explanation is strengthened by the fact that TdfI expression is induced when BSA is added to TSB medium during bacterial growth (data not shown).

A study by Hagen and Cornelissen (35) investigated whether any of the Tdf proteins is essential for intracellular survival of N. gonorrhoeae in human epithelial cells. The authors also tested a TdfI homologue knockout (NG1205), but this mutant was not affected in the intracellular survival.

The conservation of TdfI is striking; with an identity of 98.6% among the sequenced N. meningitidis strains and a 99.2% similarity at the amino acid level of the mature protein. The TdfI protein was found in all meningococci tested and all strains showed zinc-regulated expression of tdfI. Between the TdfI proteins of the sequenced meningococcal and gonococcal strains there is 96.1% identity and 97.3% similarity at the amino acid level. The differences between the sequences of TdfI are scattered throughout the protein and do not cluster in a specific loop. We find an average 41% amino acid identity of TdfI with homologs in other bacteria and in all cases the His/Asp stretch is conserved. Intriguingly, TdfI homologs were particularly found in bacterial species residing in the respiratory tract of humans and animals. Possibly in the mucosal layers of the respiratory tract the unbound zinc concentration is too low to allow sufficient passive diffusion through the porins and therefore TdfI becomes essential for bacterial growth and survival. While TdfI is not essential for intracellular survival (35) it could be essential in the bodily fluids like serum and liquor where the free zinc concentration could also be very low. Also, we cannot rule out that TdfI additionally recognizes a complexed form of zinc which may available in the respiratory tract, serum and or cerebral fluid.

We have further shown that TdfI can induce bactericidal antibodies in mice and that these antibodies are specifically directed at TdfI. Also when we used bacteria expressing TdfI from the chromosomal locus we could detect bactericidal activity, showing that during infection the antigen concentration is high enough to allow clearing of N. meningitidis.

The high level of conservation and the possibility to raise TdfI-specific bactericidal antibodies make TdfI an excellent vaccine candidate.

Materials and Methods

Abbreviations used: IPTG, isopropyl β-D-1-thiogalactopyranoside; PAR, 4-(2-pyridylazo)resorcinol; RPMI, Roswell Park Memorial Institute medium 1640; Tdf, TonB-dependent family; TPEN, N,N,N',N'-Tetrakis(2-pyridylmethyl)ethylenediamine; TSB, tryptic soy broth; ICP-MS, Inductively coupled plasma mass spectrometry.

Bacterial Strains and Growth Conditions.

Neisserial strains, listed in FIG. 5 are from the laboratory collection. Except when indicated otherwise, experiments were performed with strain HB-1 and mutants thereof. HB-1 is a non-encapsulated derivative of serogroup B strain H44/76 (Bos & Tommassen, 2005). N. meningitidis was grown on GC agar (Oxoid) plates containing Vitox (Oxoid) and antibiotics when appropriate (kanamycin, 100 µg/ml; chloramphenicol, 10 µg/ml) in candle jars at 37° C. Liquid cultures were grown in TSB (Difco) or in RPMI (Sigma) in plastic flasks at 37° C. with shaking. IPTG, zinc, and TPEN were added in the concentrations indicated s. Metals were added as a cocktail (340 nM $ZnSO_4$, 160 nM $Na_2MoO_4$, 800 nM $MnCl_2$, 80 nM $CoCl_2$ and 80 nM $CuSO_4$ final concentrations) or as single compounds in the same concentrations as in the cocktail unless indicated otherwise. Ferric chloride was added as a final concentration of 8 µM. E. coli strains DH5α and TOP10F' (Invitrogen) were used for routine cloning and BL21(DE3) (Invitrogen) for expression. An E. coli hemA mutant was used to assess the heme transport of TdfI ((22). E. coli was propagated on Luria-Bertani medium supplemented when appropriate with 100 µg/ml ampicillin, 50 µg/ml kanamycin, or 25 µg/ml chloramphenicol. For the E. coli heme-auxotroph C600 hemA::kan (22) the medium was supplemented with 5-aminolevulinic acid.

Construction of Plasmids and Mutants.

All primers were designed on the MC58 genome sequence, using NMB0964 (tdfI), NMB1730 (tonB), NMN0586 (znuA), NMB1266 (zur).

For high-level protein production in E. coli the tdfI gene without the signal sequence-encoding part was amplified from chromosomal DNA of strain H44/76 by PCR using the primers 0964-F-GATCATATGCATGAAACTGAG-CAATCGGTG- (SEQ NO:4) and 0964-R-GATGGATCCT-TAAATCTTCACGTTCACGCCGCC- (SEQ NO:5) that carry the restriction sites NdeI and BamHI, respectively (bold). The resulting product was cloned into pCRII-TOPO according to the manufacturer's recommendation (Invitrogen), yielding pCRII-tdfI, and subcloned into pET11a (Novagen) using NdeI/BamHI restriction, resulting in plasmid pET11a-tdfI.

To obtain a tdfI deletion construct, a kanamycin-resistance gene cassette (36) was amplified by PCR with the primers Kan-R-TGACGCGTCTCGACGCTGAGGTCTGC- (SEQ NO:6) and Kan-F-TGTGTACAGTCGACTTCAGACGGC-CACG- (SEQ NO:7) and cloned after MluI and BsrGI digestion into pCRII-tdfI digested with the same enzymes. In the resulting construct, pCRII-tdfI::kan, the kanamycin-resistance cassette substitutes for the region between by 437 and 1344 of tdfI. pCRII-tdfI::kan was used in a PCR with the 0964-R and 0964-F primers and the resulting product was used to transform HB-1 (37). Kanamycin-resistant colonies were tested for correct gene replacement by PCR.

The entire tdfI gene from H44/76 was amplified with primers TdfI-F-GCATCATATGGCACAAACTACACT-CAAACCC- (SEQ NO:8) and TdfI-R-ATGACGTCT-TAAAACTTCACGTTCACGCCGCC- (SEQ NO:9) that contain recognition sites for NdeI and AatII (bold), respectively. The resulting PCR product was cloned into pCRII-TOPO and subcloned into pEN11-pldA (36) using NdeI and AatII restriction sites. The resulting plasmid, pEN11-tdfI, constitutes a Neisserial replicative plasmid, containing a lacI$^Q$ gene and a tandem lac/tac promoter for controlled expression of tdfI.

The construct to generate a tonB knockout was made by amplifying DNA fragments upstream and downstream of the tonB gene using primers tonB-1 (GTACGATGATTGTGC-CGACC) (SEQ NO:10), tonB-2 (ACTTTAAACTCCGTC-GACGCAAGTCGACTGCGGGGGTTAA) (SEQ NO:11) with AccI restriction sites (bold) for one fragment, and, tonB-3 (TTAACCCCCGCAGTCGACTTGCGTC-GACGGAGTTTAAAGT) (SEQ NO:12) with restriction site AccI (bold) and tonB-4 (GCCATACTGTTGCGGATTTGA) (SEQ NO:13) for the other fragment. The two fragments were each cloned into pCRII-TOPO and then ligated to each other using the introduced restriction site AccI and the SpeI site in the pCRII-TOPO vector. The AccI site was subsequently used to clone the chloramphenicol transacetylase gene from pKD3 (38) previously cloned into pCRII-TOPO by PCR amplification with primers containing an AccI site. The resulting construct was amplified by PCR using primers tonB-1 and tonB-4 and this linear fragment was used to transform *N. meningitidis* HB-1.

The zur gene was knocked out following the same strategy. Upstream and downstream fragments were amplified in this case with primers: zur-1 (TTCGCCGATGGCGGAATACA) (SEQ NO:14), zur-2 (CTTTCAGCGCAAAGTCGACTC-CGTCGACGCGTGCCTGTTC) (SEQ NO:15) with the restriction site AccI in bold, zur-3 (GAACAG-GCACGCGTCGACGGAGTCGACTTTGCGCTGAAAG) (SEQ NO:16) with the restriction site AccI in bold and zur-4 (TCCTATTGCGCAATACCCCC) (SEQ NO:17).

A porA derivative of *N. meningiditis* strain H44/76, called CE2001 (39) was transformed with pMF121, resulting in deletion of the entire capsule locus and production of lipopolysaccharide with a truncated outer core (36). A pLAFR-derived plasmid containing the tonB, exbB and exbD genes of *N. meningitidis* ((13) was described previously.

SDS-PAGE and Western Blot Analysis.

Cell lysates were prepared from bacteria grown for 6 hours. The cells were diluted to $OD_{600nm}$ 1, pelleted, and boiled in 100 µl SDS-PAGE sample buffer containing 2% SDS and 5% 2-mercaptoethanol. Proteins were separated by standard SDS-PAGE. Gels were either stained with Coomassie brilliant blue or the proteins were transferred to nitrocellulose membranes (Protran) using a wet transfer system (Biorad) in 25 mM Tris-HCl, 192 mM glycine, 20% methanol. Membranes were blocked for 1 h in PBS containing 0.1% TWEEN® 20 and 0.5% PROTIFAR® (Nutricia). Blots were incubated with antibodies in blocking buffer. Antibody binding was detected by using goat anti-rabbit IgG peroxidase-conjugated secondary antibodies (Biosource) and enhanced chemiluminescence detection (Pierce).

Immunizations.

BL21(DE3) cells containing pET11a-tdfI were grown in LB to an $OD A_{600}$ of 0.6 after which 1 mM IPTG was added and growth was continued for 2 h. The TdfI protein accumulated in inclusion bodies, which were isolated as described (40), and the purified protein was used to immunize rabbits at Eurogentec. The resulting antiserum, SN1042, was used in a ⅕₀₀₀ dilution.

Outer membrane vesicles of strain CE1523/pEN11-tdfI grown in the presence or absence of 1 mM IPTG, were prepared by deoxycholate extraction (41) and used to immunize mice as described (32). Sera from ten mice per group were collected after 42 days and pooled. The experiments complied with the relevant national guidelines of Belgium and institutional policies of GlaxoSmithKline Biologicals.

RT-qPCR.

RT-qPCR was performed using an Applied Biosystems 7900HT Fast Real-Time PCR System and SYBR® green master mix (Applied Biosystems) according to the manufacturer's recommendations. Total RNA was isolated by resuspending approximately $4 \times 10^9$ *Neisseria* cells in 3 ml TRI-ZOL® (Invitrogen). After the addition of 600 µl chloroform and centrifugation, the upper phase was mixed 1:1 with 75% ethanol. This was loaded on a NUCLEOSPIN® RNA II column (Macherey-Nagel), which was subsequently washed with buffer R3 from the NUCLEOSPIN® RNA II kit and eluted with 100 µl water. The RNA was then treated with TURBO DNA-FREE™ (Ambion) to yield DNA-free RNA. To generate the cDNA, 1 µg of total RNA was reverse transcribed from random hexamers using transcriptor High fidelity cDNA synthesis kit (Roche) according to the manufacturer's recommendations. As a control, parallel samples were prepared in which the reverse transcriptase was omitted from the reaction mixture. PCRs were performed in triplicate in a 25-µl volume in a 96-well plate (Applied Biosystems) with the following cycle parameters: 95° C. for 10 min for enzyme activation followed by 40 cycles of 95° C. for 15 s and 60° C. for 1 min. A melting plot was performed to ensure that the signal originated from the specific amplicon. Data analysis was performed using the comparative cycle threshold method (Applied Biosystems) to determine relative expression levels. The rmpM transcript was used to normalize all data.

ICP-MS.

Total zinc concentrations were measured by ICP-MS at the integrated laboratory of the department of Geochemistry at the Utrecht University. *N. meningitidis* strains were grown in RPMI medium from a 0.1 starting $OD A_{550}$ for 6 h; at this time point a sample was taken and the remaining culture was grown for an additional hour in the presence of 1 µM zinc. After this hour, a second sample was taken. Both samples (7 ml) were washed in phosphate-buffered saline and resuspended in water, killed for 1 h at 56° C. and frozen at −80° C. The samples were then thawed, sonicated and filtered through 0.22-µm filters (Millipore).

PAR Competition Assay.

The PAR competition assay is a colorimetric reaction where the orange color of the PAR-zinc complex changes towards yellow in the presence of a protein or chemical that is able to release zinc from PAR. The assay was performed as described (42) with the following modifications: Instead of 50 µM we added 30 µM zinc and we first measured the PAR-zinc solution and then added the outer membrane vesicles to the cuvette and re-measured the solution. In this way we avoided the potential color change induced in time by UV. The data was then first normalized to the PAR-zinc measurement and then to the PAR alone sample to obtain the binding values for the outer membrane vesicles. The results shown are the normalized data of the absorption at 500 nm.

Serum Bactericidal Assay.

Wild-type H44/76 was transformed with pEN11-tdfI and inoculated from overnight grown plates in TSB with 125 µM $FeCl_3$ with or without 1 mM IPTG in shaking flasks for 3 h at 37° C. until an $OD A_{550}$ of 0.5 was reached. Serum to be tested was diluted 1:100 in Hank's balanced salt solution (HBSS) (GIBCO), 0.3% BSA and then serially diluted (two-fold dilution steps, eight dilutions) in a 50-µl volume in sterile U-bottom 96-well microtiter plates (NUNC). Bacteria were diluted in HBSS, 0.3% BSA to yield ~13,000 CFU per ml and 37.5 µl samples of the suspension were added to the serum dilutions. The microtiter plates were incubated at 37° C. for 15 min while shaking. Subsequently, 12.5 µl of baby-rabbit complement (Pelfreez) or, as control for toxicity of the sera, heat-inactivated (56° C. for 45 min) complement was added to the wells. After 1 h incubation at 37° C. while shaking, the microtiter plates were placed on ice to stop the killing. Of each well, 20 µl was spotted on GC plates while plates were tilted to allow the drop to "run" down the plate. After overnight incubation, colonies were counted and the percentage of killing was calculated. The bactericidal titer was defined as the highest serum dilution yielding >50% killing.

REFERENCES

1. Ratledge, C. 2007. Iron metabolism and infection. *Food. Nutr. Bull.* 28:S515-523.
2. Wandersman, C., and P. Delepelaire. 2004. Bacterial iron sources: from siderophores to hemophores. *Annu. Rev. Microbiol.* 58:611-647.
3. Wiener, M. C. 2005. TonB-dependent outer membrane transport: going for Baroque? *Curr. Opin. Struct. Biol.* 15:394-400.
4. Postle, K. 1993. TonB protein and energy transduction between membranes. *J. Bioenerg. Biomembr.* 25:591-601.
5. Braun, V. 2006. Energy transfer between biological membranes. *ACS Chem. Biol.* 1:352-354.

6. De, S. K., M. T. McMaster, and G. K. Andrews. 1990. Endotoxin induction of murine metallothionein gene expression. *J. Biol. Chem.* 265:15267-15274.
7. Corbin, B. D., E. H. Seeley, A. Raab, J. Feldmann, M. R. Miller, V. J. Torres, K. L. Anderson, B. M. Dattilo, P. M. Dunman, R. Gerads, R. M. Caprioli, W. Nacken, W. J. Chazin, and E. P. Skaar. 2008. Metal chelation and inhibition of bacterial growth in tissue abscesses. *Science.* 319:962-965.
8. Stephens, D. S., and S. M. Zimmer. 2002. Pathogenesis, therapy, and prevention of meningococcal sepsis. *Curr. Infect. Dis. Rep.* 4:377-386.
9. Finne, J., M. Leinonen, and P. H. Mäkelä. 1983. Antigenic similarities between brain components and bacteria causing meningitis. Implications for vaccine development and pathogenesis. *Lancet.* 2:355-357.
10. Pettersson, A., A. Maas, and J. Tommassen. 1994. Identification of the iroA gene product of *Neisseria meningitidis* as a lactoferrin receptor. *J. Bacteriol.* 176:1764-1766.
11. Legrain, M., V. Mazarin, S. W. Irwin, B. Bouchon, M. J. Quentin-Millet, E. Jacobs, and A. B. Schryvers. 1993. Cloning and characterization of *Neisseria meningitidis* genes encoding the transferrin-binding proteins Tbp1 and Tbp2. *Gene.* 130:73-80.
12. Lewis, L. A., E. Gray, Y. P. Wang, B. A. Roe, and D. W. Dyer. 1997. Molecular characterization of hpuAB, the haemoglobin-haptoglobin-utilization operon of *Neisseria meningitidis*. *Mol. Microbiol.* 23:737-749.
13. Stojiljkovic, I., V. Hwa, L. de Saint Martin, P. O'Gaora, X. Nassif, F. Heffron, and M. So. 1995. The *Neisseria meningitidis* haemoglobin receptor: its role in iron utilization and virulence. *Mol. Microbiol.* 15:531-541.
14. Carson, S. D., P. E. Klebba, S. M. Newton, and P. F. Sparling. 1999. Ferric enterobactin binding and utilization by *Neisseria gonorrhoeae*. *J. Bacteriol.* 181:2895-2901.
15. Turner, P. C., C. E. Thomas, I. Stojiljkovic, C. Elkins, G. Kizel, D. A. Ala'Aldeen, and P. F. Sparling. 2001. Neisserial TonB-dependent outer-membrane proteins: detection, regulation and distribution of three putative candidates identified from the genome sequences. *Microbiology.* 147:1277-1290.
16. Ducey, T. F., M. B. Carson, J. Orvis, A. P. Stintzi, and D. W. Dyer. 2005. Identification of the iron-responsive genes of *Neisseria gonorrhoeae* by microarray analysis in defined medium. *J. Bacteriol.* 187:4865-4874.
17. Grifantini, R., E. Frigimelica, I. Delany, E. Bartolini, S. Giovinazzi, S. Balloni, S. Agarwal, G. Galli, C. Genco, and G. Grandi. 2004. Characterization of a novel *Neisseria meningitidis* Fur and iron-regulated operon required for protection from oxidative stress: utility of DNA microarray in the assignment of the biological role of hypothetical genes. *Mol. Microbiol.* 54:962-979.
18. Dove, J. E., K. Yasukawa, C. R. Tinsley, and X. Nassif. 2003. Production of the signalling molecule, autoinducer-2, by *Neisseria meningitidis*: lack of evidence for a concerted transcriptional response. *Microbiology.* 149:1859-1869.
19. Altschul, S. F., T. L. Madden, A. A. Schaffer, J. Zhang, Z. Zhang, W. Miller, and D. J. Lipman. 1997. Gapped BLAST and PSI-BLAST: a new generation of protein database search programs. *Nucleic Acids Res.* 25:3389-3402.
20. Furano, K., and A. A. Campagnari. 2004. Identification of a hemin utilization protein of *Moraxella catarrhalis* (HumA) *Infect. Immun.* 72:6426-6432.
21. Mazoy, R., and M. L. Lemos. 1996. Identification of heme-binding proteins in the cell membranes of *Vibrio anguillarum*. *FEMS Microbiol. Lett.* 135:265-270.
22. Ghigo, J. M., S. Létoffé, and C. Wandersman. 1997. A new type of hemophore-dependent heme acquisition system of *Serratia marcescens* reconstituted in *Escherichia coli*. *J. Bacteriol.* 179:3572-3579.
23. Patzer, S. I., and K. Hantke. 1998. The ZnuABC high-affinity zinc uptake system and its regulator Zur in *Escherichia coli*. *Mol. Microbiol.* 28:1199-1210.
24. Ferguson, A. D., E. Hofmann, J. W. Coulton, K. Diederichs, and W. Welte. 1998. Siderophore-mediated iron transport: crystal structure of FhuA with bound lipopolysaccharide. *Science.* 282:2215-2220.
25. Yatsunyk, L. A., J. A. Easton, L. R. Kim, S. A. Sugarbaker, B. Bennett, R. M. Breece, Vorontsov, II, D. L. Tierney, M. W. Crowder, and A. C. Rosenzweig. 2008. Structure and metal binding properties of ZnuA, a periplasmic zinc transporter from *Escherichia coli*. *J. Biol. Inorg. Chem.* 13:271-288.
26. Bentley, S. D., G. S. Vernikos, L. A. Snyder, C. Churcher, C. Arrowsmith, T. Chillingworth, A. Cronin, P. H. Davis, N. E. Holroyd, K. Jagels, M. Maddison, S. Moule, E. Rabbinowitsch, S. Sharp, L. Unwin, S. Whitehead, M. A. Quail, M. Achtman, B. Barrell, N. J. Saunders, and J. Parkhill. 2007. Meningococcal genetic variation mechanisms viewed through comparative analysis of serogroup C strain FAM18. *PLoS Genet.* 3:e23.
27. Dempsey, J. A., W. Litaker, A. Madhure, T. L. Snodgrass, and J. G. Cannon. 1991. Physical map of the chromosome of *Neisseria gonorrhoeae* FA1090 with locations of genetic markers, including opa and pil genes. *J. Bacteriol.* 173:5476-5486.
28. Parkhill, J., M. Achtman, K. D. James, S. D. Bentley, C. Churcher, S. R. Klee, G. Morelli, D. Basham, D. Brown, T. Chillingworth, R. M. Davies, P. Davis, K. Devlin, T. Feltwell, N. Hamlin, S. Holroyd, K. Jagels, S. Leather, S. Moule, K. Mungall, M. A. Quail, M. A. Rajandream, K. M. Rutherford, M. Simmonds, J. Skelton, S. Whitehead, B. G. Spratt, and B. G. Barrell. 2000. Complete DNA sequence of a serogroup A strain of *Neisseria meningitidis* Z2491. *Nature.* 404:502-506.
29. Tettelin, H., N. J. Saunders, J. Heidelberg, A. C. Jeffries, K. E. Nelson, J. A. Eisen, K. A. Ketchum, D. W. Hood, J. F. Peden, R. J. Dodson, W. C. Nelson, M. L. Gwinn, R. DeBoy, J. D. Peterson, E. K. Hickey, D. H. Haft, S. L. Salzberg, O. White, R. D. Fleischmann, B. A. Dougherty, T. Mason, A. Ciecko, D. S. Parksey, E. Blair, H. Cittone, E. B. Clark, M. D. Cotton, T. R. Utterback, H. Khouri, H. Qin, J. Vamathevan, J. Gill, V. Scarlato, V. Masignani, M. Pizza, G. Grandi, L. Sun, H. O. Smith, C. M. Fraser, E. R. Moxon, R. Rappuoli, and J. C. Venter. 2000. Complete genome sequence of *Neisseria meningitidis* serogroup B strain MC58. *Science.* 287:1809-1815.
30. Chen, C. Y., and S. A. Morse. 2001. Identification and characterization of a high-affinity zinc uptake system in *Neisseria gonorrhoeae*. *FEMS Microbiol. Lett.* 202:67-71.
31. Ammendola, S., P. Pasquali, C. Pistoia, P. Petrucci, P. Petrarca, G. Rotilio, and A. Battistoni. 2007. The high affinity $Zn^{2+}$ uptake system ZnuABC is required for bacterial zinc homeostasis in intracellular environments and contributes to virulence of *Salmonella enterica*. *Infect. Immun.* 75:5867-5876.
32. Stewart, A. J., C. A. Blindauer, S. Berezenko, D. Sleep, and P. J. Sadler. 2003. Interdomain zinc site on human albumin. *Proc. Natl. Acad. Sci. USA.* 100:3701-3706.
33. Wu, H. J., K. L. Seib, Y. N. Srikhanta, S. P. Kidd, J. L. Edwards, T. L. Maguire, S. M. Grimmond, M. A. Apicella, A. G. McEwan, and M. P. Jennings. 2006. PerR controls Mn-dependent resistance to oxidative stress in *Neisseria gonorrhoeae*. *Mol. Microbiol.* 60:401-416.
34. Nanamiya, H., G. Akanuma, Y. Natori, R. Murayama, S. Kosono, T. Kudo, K. Kobayashi, N. Ogasawara, S. M. Park, K. Ochi, and F. Kawamura. 2004. Zinc is a key factor in controlling alternation of two types of L31 protein in the *Bacillus subtilis* ribosome. *Mol. Microbiol.* 52:273-283.

35. Hagen, T. A., and C. N. Cornelissen. 2006. *Neisseria gonorrhoeae* requires expression of TonB and the putative transporter TdfF to replicate within cervical epithelial cells. *Mol. Microbiol.* 62:1144-1157.
36. Bos, M. P., B. Tefsen, P. Voet, V. Weynants, J. P. M. van Putten, and J. Tommassen. 2005. Function of neisserial outer membrane phospholipase A in autolysis and assessment of its vaccine potential. *Infect. Immun.* 73:2222-2231.
37. Voulhoux, R., M. P. Bos, J. Geurtsen, M. Mols, and J. Tommassen. 2003. Role of a highly conserved bacterial protein in outer membrane protein assembly. *Science.* 299:262-265.
38. Datsenko, K. A., and B. L. Wanner. 2000. One-step inactivation of chromosomal genes in *Escherichia coli* K-12 using PCR products. *Proc. Natl. Acad. Sci. USA.* 97:6640-6645.
39. Tommassen, J., P. Vermeij, M. Struyvé, R. Benz, and J. T. Poolman. 1990. Isolation of *Neisseria meningitidis* mutants deficient in class 1 (PorA) and class 3 (PorB) outer membrane proteins. *Infect. Immun.* 58:1355-1359.
40. Dekker, N., K. Merck, J. Tommassen, and H. M. Verheij. 1995. In vitro folding of *Escherichia coli* outer-membrane phospholipase A. *Eur. J. Biochem.* 232:214-219.
41. Weynants, V. E., C. M. Feron, K. K. Goraj, M. P. Bos, P. A. Denoel, V. G. Verlant, J. Tommassen, I. R. Peak, R. C. Judd, M. P. Jennings, and J. T. Poolman. 2007. Additive and synergistic bactericidal activity of antibodies directed against minor outer membrane proteins of *Neisseria meningitidis. Infect. Immun.* 75:5434-5442.
42. Lim, K. H., C. E. Jones, R. N. vanden Hoven, J. L. Edwards, M. L. Falsetta, M. A. Apicella, M. P. Jennings, and A. G. McEwan. 2008. Metal binding specificity of the MntABC permease of *Neisseria gonorrhoeae* and its influence on bacterial growth and interaction with cervical epithelial cells. *Infect. Immun.* 76:3569-3576.

TABLE 1

Conservation of the mature TdfI protein sequence in the sequenced *Neisseria* strains.

| Similarity (%) | Strain | Identity (%) | | | | | | |
|---|---|---|---|---|---|---|---|---|
| | | MC58 | Fam18 | Z2491 | 053442 | FA1090 | NCCP 11945 | ST-640 |
| | *N. meningitidis* MC58 | | 730/734 (99.5) | 720/734 (98.1) | 720/734 (98.1) | 706/734 (96.2) | 707/734 (96.3) | 712/734 (97.0) |
| | *N. meningitidis* Fam18 | 733/734 (99.9) | | 722/734 (98.4) | 718/734 (97.8) | 705/734 (96.0) | 706/734 (96.2) | 712/734 (97.0) |
| | *N. meningitidis* Z2491 | 725/734 (98.8) | 726/734 (98.9) | | 716/734 (97.5) | 707/734 (96.3) | 706/734 (96.2) | 710/734 (96.7) |
| | *N. meningitidis* 053442 | 726/734 (98.9) | 727/734 (99.0) | 723/734 (98.5) | | 706/734 (96.2) | 707/734 (96.3) | 707/734 (96.3) |
| | *N. gonorrhoeae* FA1090 | 715/734 (97.4) | 714/734 (97.3) | 714/734 (97.3) | 715/734 (97.4) | | 733/734 (99.9) | 702/734 (95.6) |
| | *N. gonorrhoeae* NCCP11945 | 716/734 (97.5) | 715/734 (97.4) | 713/734 (97.1) | 716/734 (97.5) | 733/734 (99.9) | | 701/734 (95.5) |
| | *N. lactamica* ST-640 | 717/734 (97.7) | 718/734 (97.8) | 718/734 (97.8) | 715/734 (97.4) | 711/734 (96.9) | 710/734 (96.7) | |

What is claimed is:

1. An immunogenic composition comprising:
   (a) a pharmaceutically acceptable excipient and
   (b) isolated outer membrane vesicles enriched in the zinc-regulated NMB0964 polypeptide of *Neisseria meningitidis*, wherein the isolated outer membrane vesicles are from a *Neisseria meningitidis* that is genetically modified through the disruption of functional expression of its Zur repressor protein, NMB1266, wherein the genetically modified *Neisseria meningitidis* produces an upregulated level of the NMB0964 polypeptide in the outer membrane vesicles, wherein said immunogenic composition when administered to a mammal in an immunologically effective amount, elicits antibodies specific to the NMB0964 polypeptide in the mammal.

2. The immunogenic composition of claim 1, wherein the *Neisseria meningitidis* is serogroup B *Neisseria meningitidis*.

3. The immunogenic composition of claim 1, wherein the *Neisseria meningitidis* is of immunotype L2 or L3.

4. The immunogenic composition of claim 1, wherein the outer membrane vesicles are isolated by extracting with 0.02 to 0.5% detergent.

5. A method of eliciting an immune response against *Neisseria meningitidis*, said method comprising administering to a mammal an immunologically effective amount of the immunogenic composition of claim 1.

6. A method of producing the immunogenic composition of claim 1, the method comprising:
- (a) culturing the genetically modified *Neisseria meningitidis* in a culture medium comprising the zinc chelator, TPEN (N,N,N',N'-Tetrakis(2-pyridylmethyl)ethylenediamine);
- (b) isolating the outer membrane vesicles from the cultured genetically modified *Neisseria meningitidis* and
- (c) combining the isolated outer membrane vesicles with the pharmaceutically acceptable excipient, thereby producing the immunogenic composition.

\* \* \* \* \*